(12) United States Patent
Bader et al.

(10) Patent No.: US 7,560,575 B2
(45) Date of Patent: Jul. 14, 2009

(54) PROCESS FOR PREPARATION OF RACEMIC NEBIVOLOL

(75) Inventors: Thomas Bader, Zurich (CH); Alfred Stutz, Zurich (CH); Harald Hofmeier, Zurich (CH); Hans-Ulrich Bichsel, Horhausen (CH)

(73) Assignee: Acino Pharma AG, Liesberg (CH)

( * ) Notice: Subject to any disclaimer, the term of this patent is extended or adjusted under 35 U.S.C. 154(b) by 687 days.

(21) Appl. No.: 11/319,287

(22) Filed: Dec. 28, 2005

(65) Prior Publication Data

US 2007/0149612 A1 Jun. 28, 2007

(51) Int. Cl.
*C07D 311/58* (2006.01)
*C07D 407/06* (2006.01)

(52) U.S. Cl. .................. 549/407; 549/274; 549/405

(58) Field of Classification Search ................. 549/274, 549/405, 407

See application file for complete search history.

(56) References Cited

U.S. PATENT DOCUMENTS

| 4,654,362 | A | 3/1987 | Van Lommen et al. |
| 4,985,574 | A | 1/1991 | Kurono et al. |
| 5,759,580 | A | 6/1998 | Jans et al. |
| 6,282,865 | B1 | 9/2001 | Bergstrom et al. |
| 6,545,040 | B1 | 4/2003 | Xhonneu et al. |

FOREIGN PATENT DOCUMENTS

| EP | 0145067 A2 | 6/1985 |
| EP | 0264586 B1 | 4/1988 |
| EP | 0331078 A3 | 9/1989 |
| EP | 0334429 A1 | 9/1989 |
| EP | 0334429 B1 | 9/1989 |
| EP | 0744946 B1 | 4/1996 |
| WO | 99/32476 | 7/1999 |
| WO | 2004/041805 A1 | 5/2004 |

OTHER PUBLICATIONS

CAS Online-compound of Registry No. 620176-90-1 which entered STN Nov. 24, 2003, source CAS Client Services.*
Johannes, et al., Zr-Catalyzed Kinetic Resolution of Allylic Ethers and Mo-Catalyzed Chromene Formation in Synthesis. Enantioselective Total Synthesis of the Antihypertensive Agent (S,R,R,R)-Nebivol, J.Am. Chem. Soc. 1998, 120, 8340-8347.
Oikawa, et al., Meldrum's Acid in Organic Synthesis. 2. A General and Versitile Synthesis of β-Keto Esters, J. Org. Chem., vol. 43, No. 10, 1978, 2087-2088.
Zhang, et al., Stereocontrol between Remote Atom Centers in Acyclic Substrates. Anti Addition of Hydride to 1,5-,1,6-, and 1,7-Hydroxy Ketones, J. Org. Chem., 1998, 63, 7964-7981.
Hase, et al., A Non-Organometallic Method for the Synthesis of Methyl Ketones From Acyl Chlorides, Synthetic Communications, 1980, 10(3), 221-224.
Concellón, et al., Diastereoselective Reducation of (S)-1-Chloro-3-silyloxybutan-2-one. Synthesis of Enantiopure (2S,3R) and (2S,3S) O-tert-Butyldimethylsily1-3,4-epoxybutan-2-ol., Tetrahedron Letters 40 (1999) 2863-2864.
Lawson, et al., Remote Stereocontrol in Acyclic Systems. Hydride Addition to 1,5-and 1,6-Hydroxy Ketones Mediated by Metal Chelation, Tetrahedron Letters 40 (1999) 593-596.
Zhang, et al. Remote Acyclic Diasterocontrol Involving a Bicyclic Metal Chelate. High 1, 5 Symmetric Induction in the Hydride Reduction of o-Hydroxy Ketones, Tetrahedron Letters, 1994, vol. 35. No. 28, 4891-4894.
Chandrasekhar, et al., Enantioselective Total Snythesis of the Antihypertensive Agent (S,R,R,R)-Nebivolol, Tetrahedron 56 (2000) 6339-6344.

\* cited by examiner

*Primary Examiner*—Bernard Dentz
(74) *Attorney, Agent, or Firm*—Caesar, Rivise, Bernstein, Cohen & Pokotilow, Ltd.

(57) ABSTRACT

A process of making racemic [2S*[R*[R*[R*]]]] and [2R*[S*[S*[S*]]]]-(±)α,α'-[iminobis(methylene)]bis[6-fluoro-3,4-dihydro-2H-1-benzopyran-2-methanol] of the compound of the formula (I)

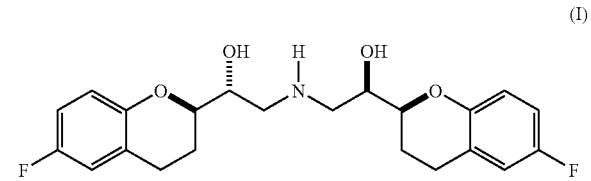

(I)

and its pure [2S*[R*[R*[R*]]]]- and [2R*[S*[S*[S*]]]]-enantiomer compounds and pharmaceutically acceptable salts thereof.

89 Claims, 7 Drawing Sheets

PROCESS FOR PREPARATION OF RACEMIC NEBIVOLOL

BACKGROUND OF THE INVENTION

1. Field of Invention

This invention relates to a novel process for preparation of racemic Nebivolol, its enantiomeric compounds and to novel compounds made by the process.

2. Description of Related Art

Nebivolol (see FIG. 1A, showing d-Nebivolol, chemical name: [2R*[R*[R*(S*)]]]-α,α'-[iminobis(methylene)]bis[6-fluoro-3,4-dihydro-2H-1-benzopyran-2-methanol] or alternatively [2R*[R*[R*(S*)]]]-α,α'-[iminobis(methylene)]bis[6-fluoro-chroman-2-methanol] and FIG. 1B showing a racemic Nebivolol, which is a mixture of l- and d- Nebivolol) is known as an adrenergic beta-antagonist, an antihypertensive agent, a platelet aggregation inhibitor and a vasodilating agent.

Nebivolol is administered as tablets (e.g., a dosage of 5.45 mg Nebivolol hydrochloride is equivalent to 5 mg Nebivolol) which contain Nebivolol as a racemic mixture of enantiomers SRRR-Nebivolol (dextro d-Nebivolol) and RSSS-Nebivolol (levo l-Nebivolol).

Nebivolol contains four asymmetric centers, and therefore 16 stereoisomers are theoretically possible. However, because of the particular constitution of the structures and configurations of the stereoisomers (e.g., axial symmetry), only 10 stereoisomers (6 diastereomers: 4 dl forms and 2 meso forms) can be formed (Table 1).

A non-stereoselective preparation of these stereoisomers is generally described in U.S. Pat. No. 4,654,362 to Van Lommen et al. (Janssen Pharmaceutica N. V.) (and its counter-part EP 0145067). A stereoselective synthesis of the isomer [2R, αS, 2'S, α'S]-α,α'-[iminobis(methylene)]bis[6-fluoro-3,4-dihydro-2H-1-benzopyran-2-methanol] has been described in U.S. Pat. No. 6,545,040 (Janssen Pharmaceutica N. V.) (and its counter-part EP 0334429).

A PCT patent application publication WO 2004/041805 (Egis Gyogyszergyar R T.) describes a new process for the preparation of racemic [2S[2R*[R[R*]]]] and [2R[2S*[S[S*]]]]-(±)α,α'-[iminobis(methylene)]bis[6-fluoro-3,4-dihydro-2H-1-benzopyran-2-methanol] and its pure [2S[2R*[R[R*]]]]-, and [2R[2S*[S[S*]]]] enantiomers.

Alternative and enantioselective syntheses of d-Nebivolol were described in J. Am. Chem. Soc. 1998, 120, 8340-8347 and Tetrahedron 56, 2000, 6339-6344.

TABLE 1

Stereoisomers of Nebivolol $R_1$ \_\_\_ N(H) \_\_\_ $R_2$ a general formula for Nebivolol isomers

| $R_1$ = | $R_2$ = (SRRS column) | SRRR | SRSR | SRSS |
|---|---|---|---|---|
| SRRS | SRRS stereoisomer 1 | SRRR stereoisomer 2 d-Nebivolol | SRSR stereoisomer 3 meso form 1 | SRSS stereoisomer 4 |
| RRRS | RRRS stereoisomer 2 d-Nebivolol | RRRR stereoisomer 5 | RRSR stereoisomer 6 | RRSS stereoisomer 7 meso form 2 |
| RSRS | RSRS stereoisomer 3 meso form 1 | RSRR stereoisomer 6 | RSSR stereoisomer 8 | RSSS stereoisomer 9 l-Nebivolol |
| SSRS | SSRS stereoisomer 4 | SSRR stereoisomer 7 meso form 2 | SSSR stereoisomer 9 l-Nebivolol | SSSS stereoisomer 10 |

Methods of preparation of Nebivolol as described in the above mentioned references are summarized below.

a. U.S. Pat. No. 4,654,362 (and its counter part EP 0145067 U.S) (Janssen Pharmaceutica N. V.)

The synthetic route for the non-stereoselective preparation of Nebivolol is described, starting from 6-fluoro-4-oxo-4H-1-benzopyran-2-carboxylic acid a1 (Scheme 1a):

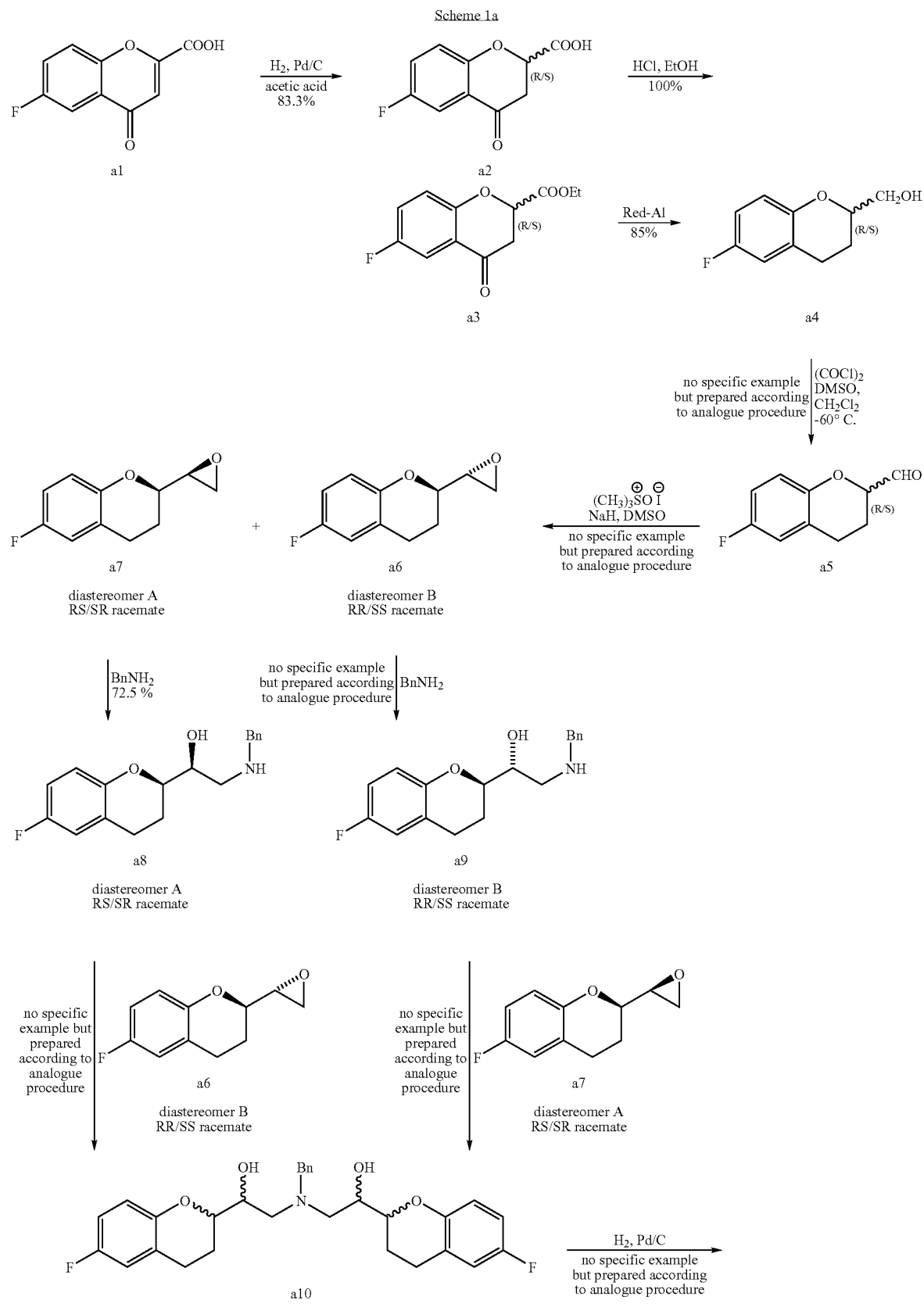

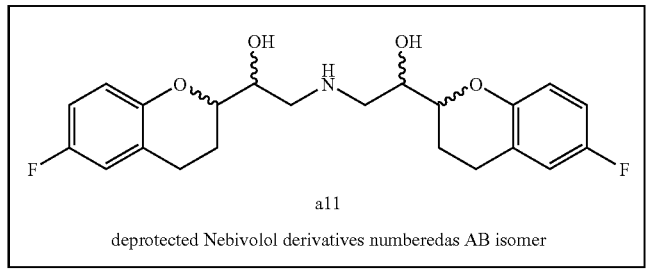

a11 deprotected Nebivolol derivatives numbered as AB isomer

For the preparation of Nebivolol according to the Scheme 1a, U.S. Pat. No. 4,654,362 and its counter-part EP 0145067 contain detailed examples for the synthesis of components a1, a2, a3, a4 and a8 only. All other examples are analogue procedures that describe the preparation of related derivatives (e.g., derivatives without the aromatic fluoro substituent). The general strategy for the preparation of Nebivolol or its corresponding derivatives is based on the synthesis of the 2-oxiranyl-chromans (a6 and a7) as key intermediates for the final coupling steps. Because they possess two asymmetric carbon atoms, these compounds may be formed from the racemic aldehydes a5 as two diastereomeric racemates ("an A form" a7=RS/SR and "a B form" a6=SS/RR) which may be separated by chromatography. This reference does not provide descriptions of a workup procedure, crystallization and purification or separation of stereoisomers, yields etc. for the desired intermediates.

The racemates a6 or a7 can be transformed by reacting with benzylamine to the corresponding benzylated aminoalkohols a8 and a9. A benzyl protected Nebivolol AB mixture a10 may be prepared by reacting of the racemate a8 (RS/SR) with the epoxide racemate a6 (RR/SS) or by reacting of racemate a9 (RR/SS) with the epoxide racemate a7 (RS/SR). The protecting group may be removed in the final step by catalytic hydrogenation to give a Nebivolol AB mixture a11.

Scheme 1b shows further methods for the synthesis of the analogous 2-chromanyl-aldehydes (a14) and 2-oxiranyl-chromanes (a16) as key intermediates for the synthesis of Nebivolol derivatives having different substituents at the aromatic moiety.

Scheme 1b

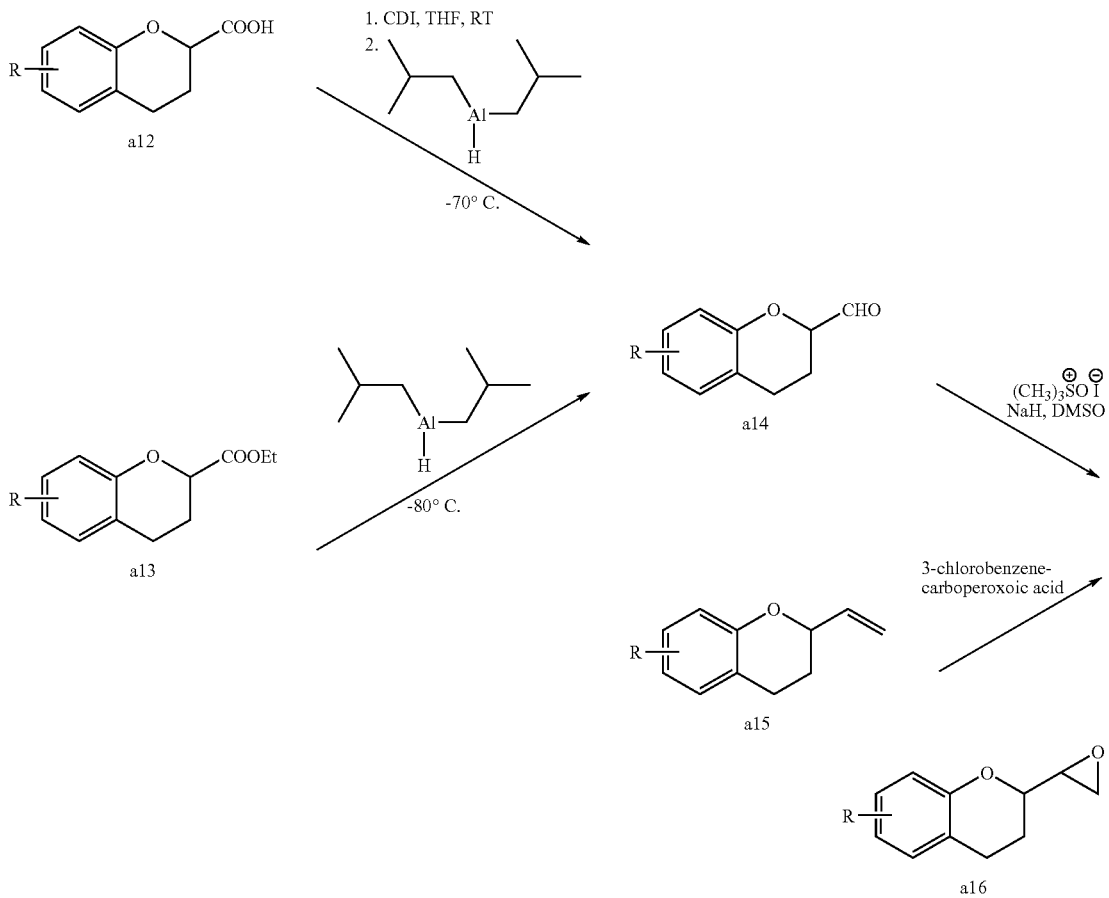

The aldehyde a14 can be obtained by low temperature reduction of the imidazolide of a12 or by the same reduction of the ester a13. The aldehyde a14 is then converted into the 2-oxiranyl-chromans a16 by reaction with sodium hydride and trimethyl sulfoxonium iodide in dimethyl sulfoxide in an analogous reaction as described above. Another possibility for the synthesis of 2-oxiranyl-chromans a16 is the oxidation of 2-vinylchroman a15 with 3-chlorobenzenecarboperoxide (the source of 2-vinylchroman a15 is not described in these patents but according to EP 0334429 (see also below), compound a14 can be converted into compound a15 by a Wittig reaction).

Scheme 1c demonstrates that diastereomeric mixtures consisting of desired and undesired diastereomers (i.e., RSSS/SRRR and RSRR/SRSS) can be produced by the method shown in Scheme 1a.

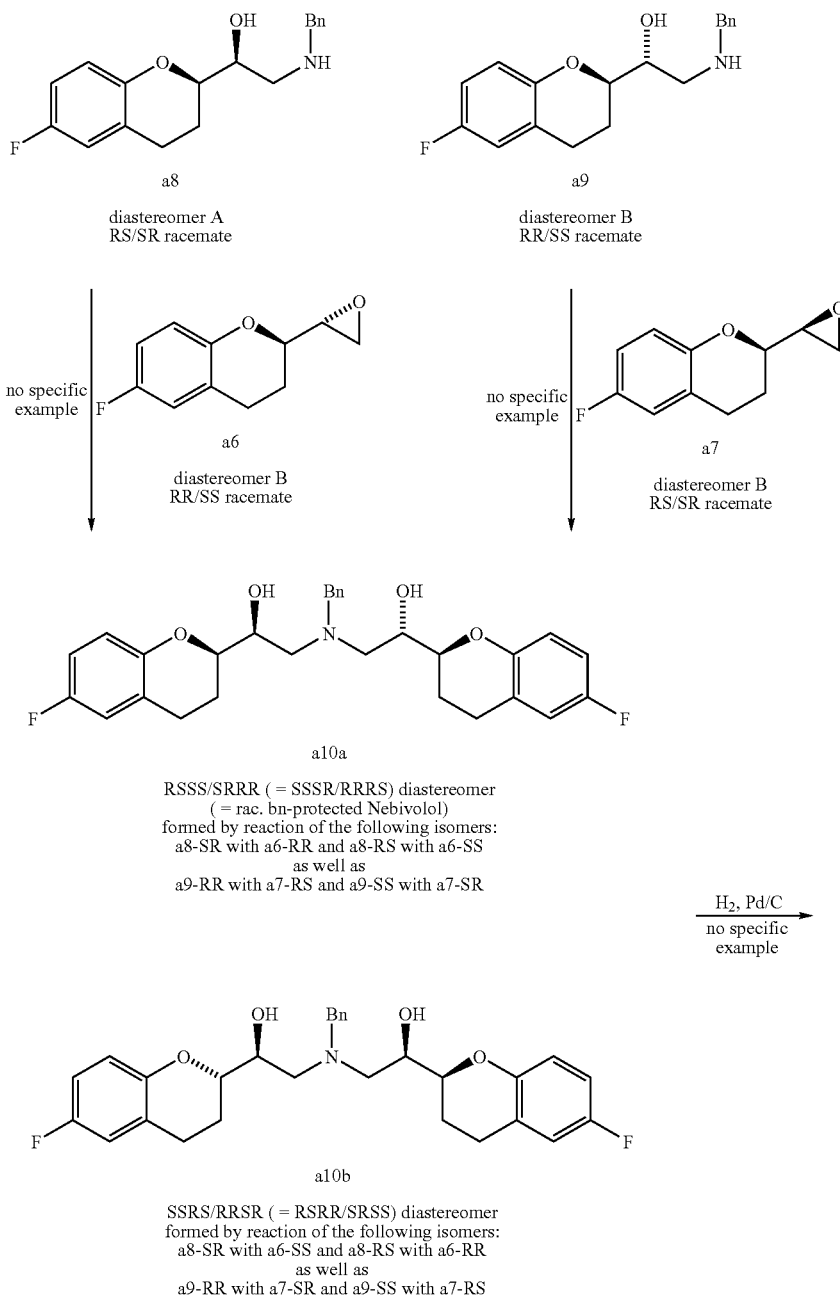

-continued

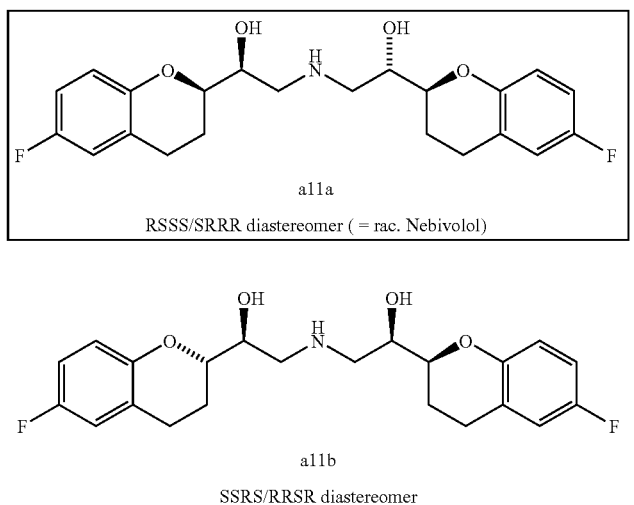

a11a
RSSS/SRRR diastereomer ( = rac. Nebivolol)

a11b
SSRS/RRSR diastereomer

The strategy described in U.S. Pat. No. 4,654,362 and its counter-part EP 0145067 has the following disadvantages:

1. The synthesis of the aldehydes a6 and a14 requires very low temperatures and therefore requires special equipment, which makes the process more complicated and expensive;

2. The aldehyde a5 is very unstable as stated in a PCT publication WO 2004/041805;

3. The synthesis of a6/a7 from a5 may be hazardous because it is known that the use of sodium hydride in solvents like DMSO, DMF, DMA and DMI can cause an exotherm and therefore, cause a runaway reaction (see UK Chemical Reaction Hazards Forum: "Sodium 15 Hydride/DMF process stopped");

4. Compounds a6 and a7 have been characterized as oily substances (see PCT publication WO 2004/041805). Since the preparation according to the described procedure is likely to form a diastereomeric mixture of a6 and a7, chromatographic purification may be required, which is not commercially viable;

5. Compounds a10 and a11 may be prepared by reaction of the racemic intermediate a8 ("isomer A") with the racemate a6 ("isomer B") or alternatively by reaction of the racemic intermediate a9 ("isomer B") with the racemate a7 ("isomer A") followed by deprotection. U.S. Pat. No. 4,654,362 and its counter-part EP 0145067 do not provide an explicit description as to whether the compounds a10 and a11 (characterized only as being the "AB" isomeric form) are single isomers or a mixture of isomers. No teaching for separation of such mixtures has been provided. It is obvious that such procedures may form diastereomeric mixtures consisting of the desired RSSS/SRRR diastereomer and the undesired RSRR/SRSS diastereomer (Scheme 1c; also compare Table 1 demonstrating combination of the different fragments to give all possible diastereomers). Moreover, it is known in prior art (see WO 2004/041805) that racemic Nebivolol prepared according to the process disclosed in U.S. Pat. No. 4,654,362 (and its counter-part EP 0145067) (Schemes 1a and 1c) and obtained as the diastereomeric racemate having the SRSS/RSRR configuration could not be successfully separated by fractional crystallization; and 6. The loss of expensive material via the formation of undesired Nebivolol isomers, especially during late process steps.

b. EP Patent Application Publication EP 0334429 and U.S. Pat. No. 6,545,040 to Xhonneux et al. (Janssen Pharmaceutica N. V.)

Similar strategy for the synthesis of Nebivolol is described in EP 0334429 and U.S. Pat. No. 6,545,040 but with the difference that l-Nebivolol is prepared by an enantioselective synthesis using the enantiopure fragments b6 and b11 (Scheme 2) as key intermediates.

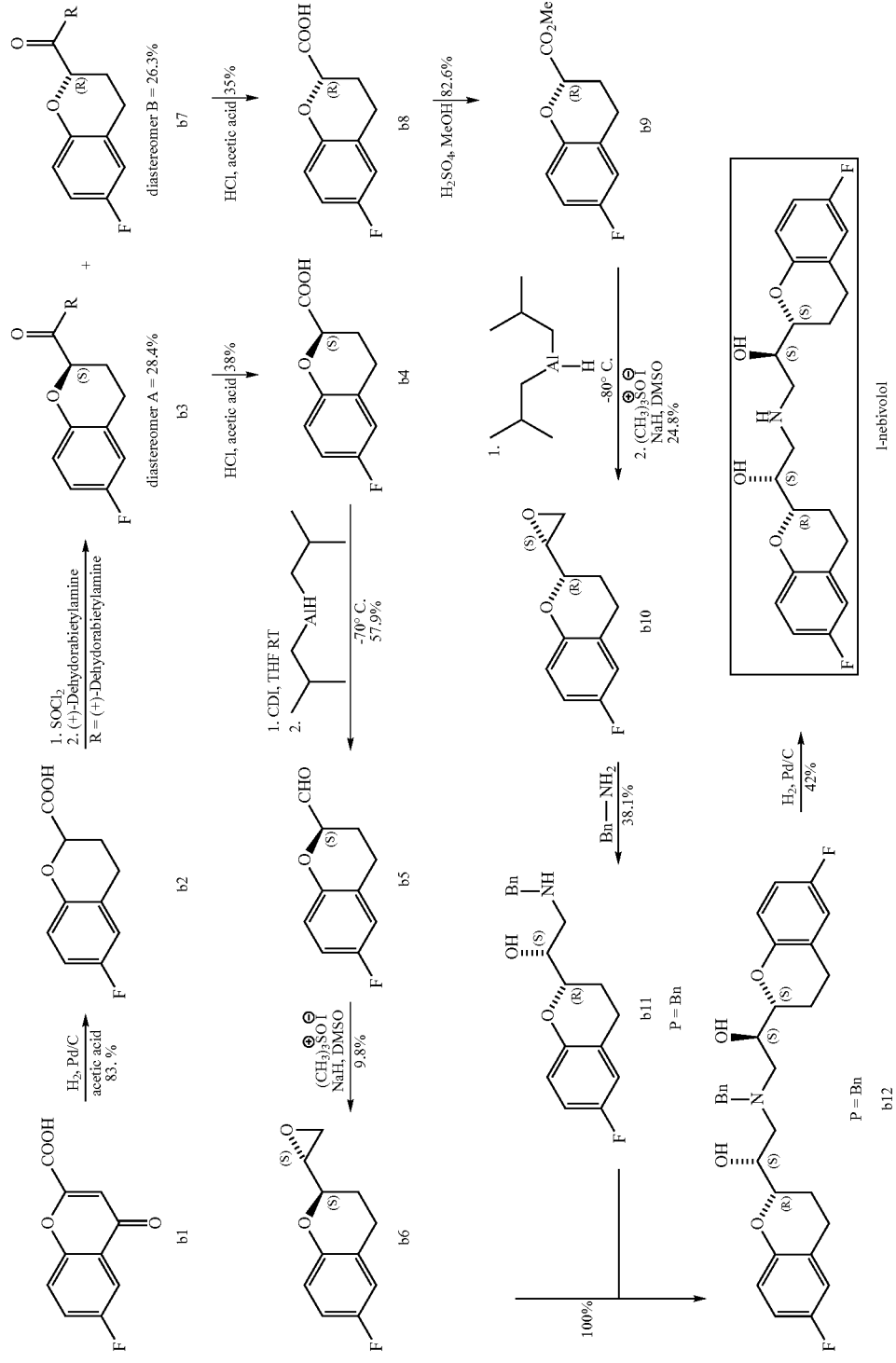

For this procedure, it was necessary to separate the racemic 6-fluoro-chroman-2-yl-carboxylic acid b2 by formation of a diastereomeric amide b3 with (+)-dehydroabietylamine followed by fractional crystallization of the diastereomers and hydrolysis of the amides. The next steps for the synthesis of the fragments b6 and b11 were done in convergent pathways using the (S)-form and (R)-form of the 6-fluoro-chroman-2-yl-carboxylic acids b4 and b8. The (S)-6-fluoro-chroman-2-yl-carboxylic acid b4 was first converted to the aldehyde b5 according to the procedure, already mentioned in scheme 1b. The epoxide b6 could be then obtained by reacting of b5 with sodium hydride and trimethyl sulfoxonium iodide in dimethyl sulfoxide. On the second pathway the (R)-6-fluoro-chroman-2-yl-carboxylic acid b8 was first esterified to b9. Epoxide b10 was synthesized in a one-pot procedure by reduction of b9 to the corresponding aldehyde followed by reaction with sodium hydride and trimethyl sulfoxonium iodide in dimethyl sulfoxide. The epoxide ring of b10 was opened by substitution with benzylamine to give the second key fragment b11, which was then reacted with the epoxide b6 to obtain benzyl-protected 1-Nebivolol b12. Final deprotection by catalytical hydrogenation of b12 gave 1-Nebivolol.

The strategy described in EP 0334429 and U.S. Pat. No. 6,545,040 has the following disadvantages:

1. The steps of preparing compounds b5 from b4 and b10 from b9 require very low temperatures for the diisobutylaluminum hydride (DIBAH) reduction, making the process more complicated and expensive due to the need for special refrigerating equipment;

2. The steps of preparing compounds b6 from b5 and b10 from b9 may have safety hazards because it is known that the use of sodium hydride-in solvents like DMSO, DMF, DMA and DMI can lead to an exotherm and could cause a runaway reaction (see UK Chemical Reaction Hazards Forum: "Sodium Hydride/DMF process stopped");

3. Compounds b5, b6, b9 and b10 are oily substances and therefore difficult to purify; in the likely case that compounds b6 and b10 are contaminated with undesired diastereomers, separation by column chromatography may be required, which is not a commercially viable procedure;

4. The low yields, especially those of steps of preparing compounds b2-b3-b4, b2-b7-b8 and b5-b6, b9-b10, result in a very low overall yield ($\leq 0.5\%$) for the synthesis of l-Nebivolol making this procedure uneconomical;

5. Since only l-Nebivolol is prepared and a racemic mixture is required for preparation of Nebivolol, additional steps are necessary to synthesize the corresponding d-form (i.e., d-Nebivolol); and 6. Upon reacting the intermediate b2, diastereomers b3 and b7 were formed which then had to be separated and treated separately to yield b6 and b11, later combined to yield b12, thus requiring multiple additional steps in the process.

c. PCT Patent Application Publication WO 2004/041805 to Trinka et al., (EGIS GYOGYSZERGYAR RT)

WO 2004/041805 describes the enantioselective synthesis of d- and l-Nebivolol (see Schemes 3a-c).

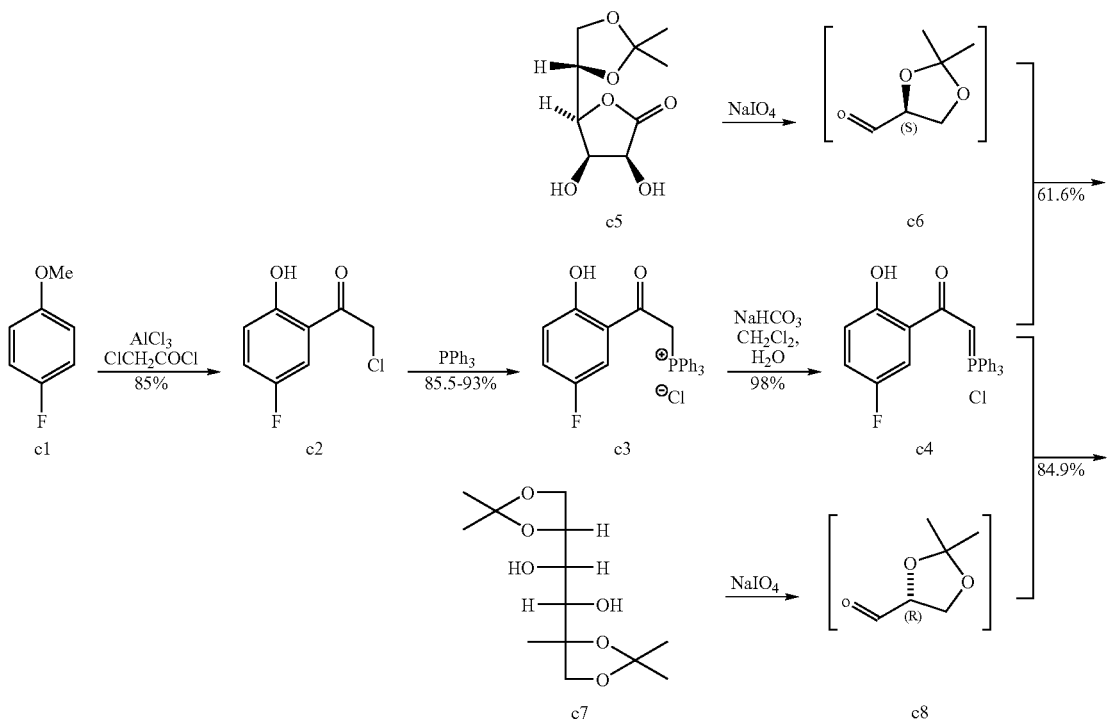

Scheme 3a

-continued

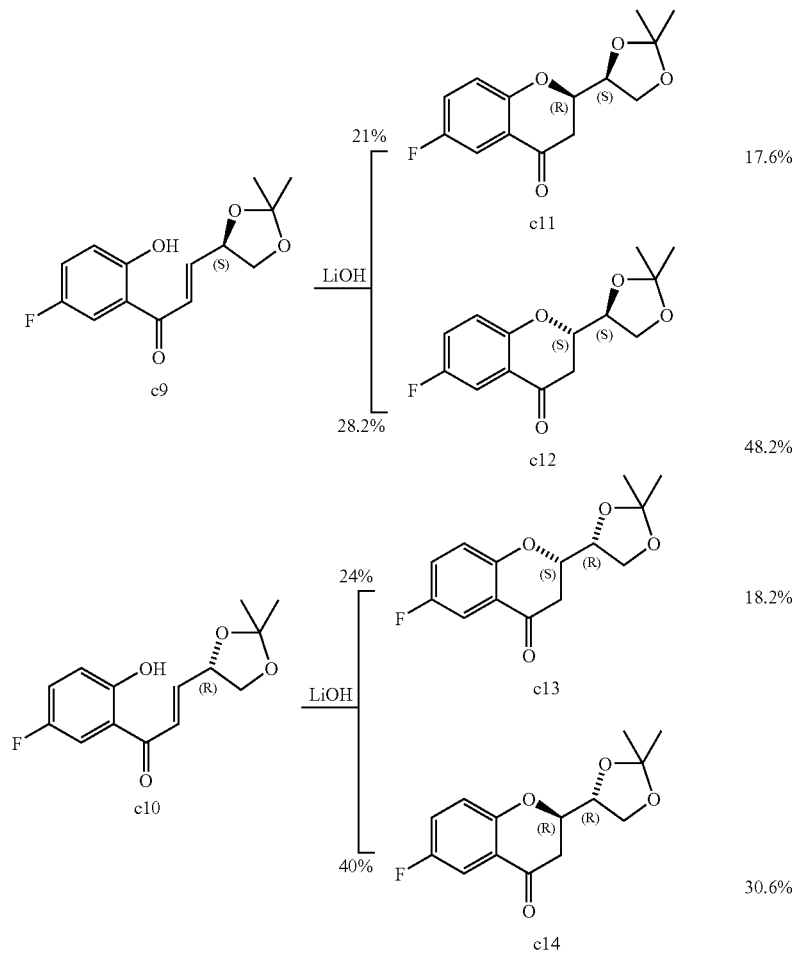

The strategy of this route is based on the synthesis and separation of isopropylidene protected (1',2'-dihydroxy-ethyl)-6-fluoro-chroman-4-one isomers c11, c12, c13, c14 (Scheme 3a). These compounds were synthesized by starting with the Friedel-Crafts acylation of 4-fluoroanisole c1 using chloroacetyl chloride to give the chloroacetyl compound c2, which was further transformed with triphenylphosphine followed by treatment with a weak base to form the stable phosphanylidene compound c4. The compound c4 was then reacted separately with protected glycerinealdehydes c6 (obtained from vitamin C) to give c11 and c12 or with c8 (obtained from D-mannitol) to give c13 and c14 after the cycling.

Each of these isomers was further transformed in four pathways and in the same manner (Schemes 3b and 3c), whereby according to pathways 1 and 2, l-Nebivolol was prepared using c11 and c12 as starting compounds (Scheme 3b).

The enantiomeric d-Nebivolol was prepared in the analogous fashion, wherein the starting compounds were the S,R-isomer c13 and R,R-isomer c14 of isopropylidene protected (1',2'-dihydroxy-ethyl)-6-fluoro-chroman-4-one (pathways 3 and 4, Scheme 3c).

The typical reaction sequence for each pathway started with the deprotection of c11 (pathway 1, Scheme 3b), c12 (pathway 2, Scheme 3b), c13 (pathway 3, Scheme 3c), c14 (pathway 4, Scheme 3c) to obtain the respective diols c15, c19, c25, c29. Selective tosylation of the primary alcohol group gave the compounds c16, c20, c26, c30 which could be transformed to the epoxides c17, c21, c27, c31 by treatment with a base. After the conversion of these epoxides with benzylamine to c18, c22, c28, c32 and substitution with the desired epoxides (c18+c21, c22+c17, c28+c31, c32+c27), the benzyl protected diketo compounds c23 and c33 were formed. Deprotection and reduction of the carbonyl groups could be carried out in a one pot reaction by catalytic hydrogenation to give either l-Nebivolol or d-Nebivolol.

Racemic Nebivolol was obtained by preparing a 1:1 mixture of the intermediates c23 and c33 before performing the last hydrogenation step (yield 52%).

Scheme 3b:
pathway 1:
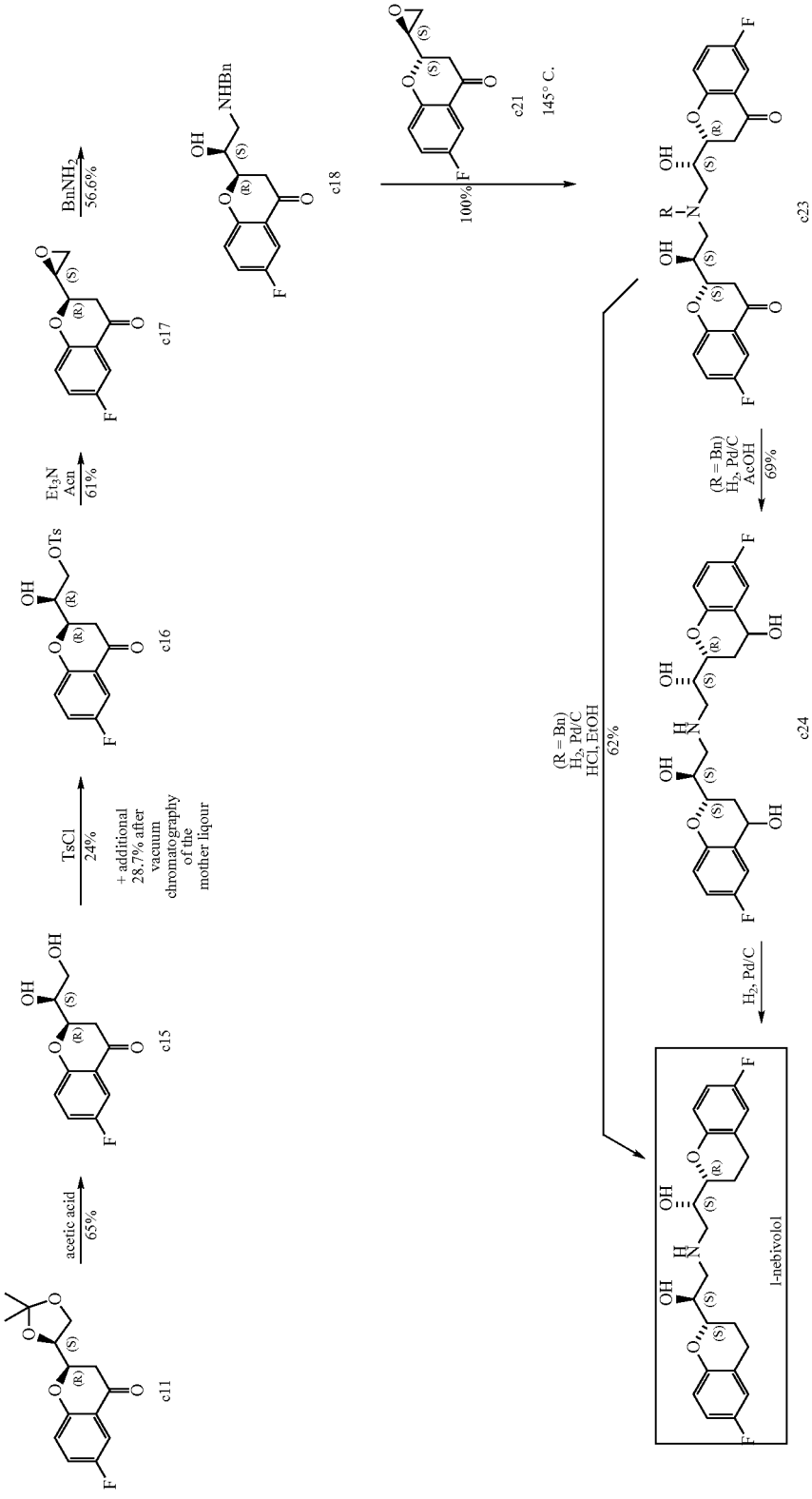

pathway 2:
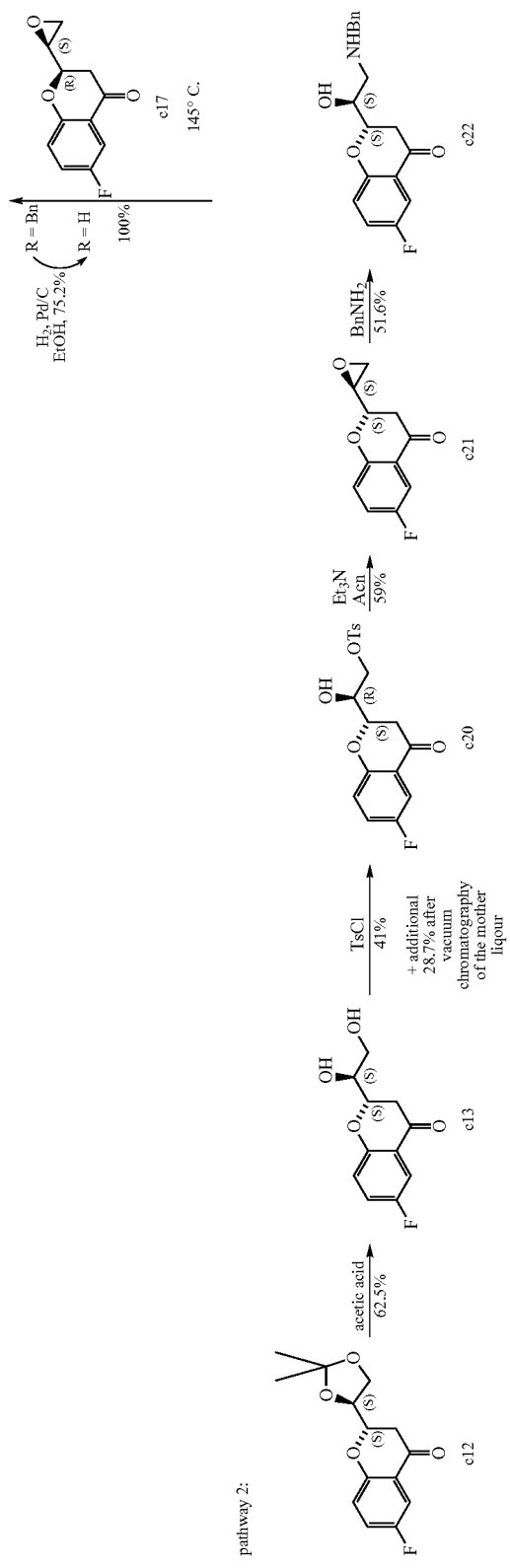

Scheme 3c:
pathway 3:
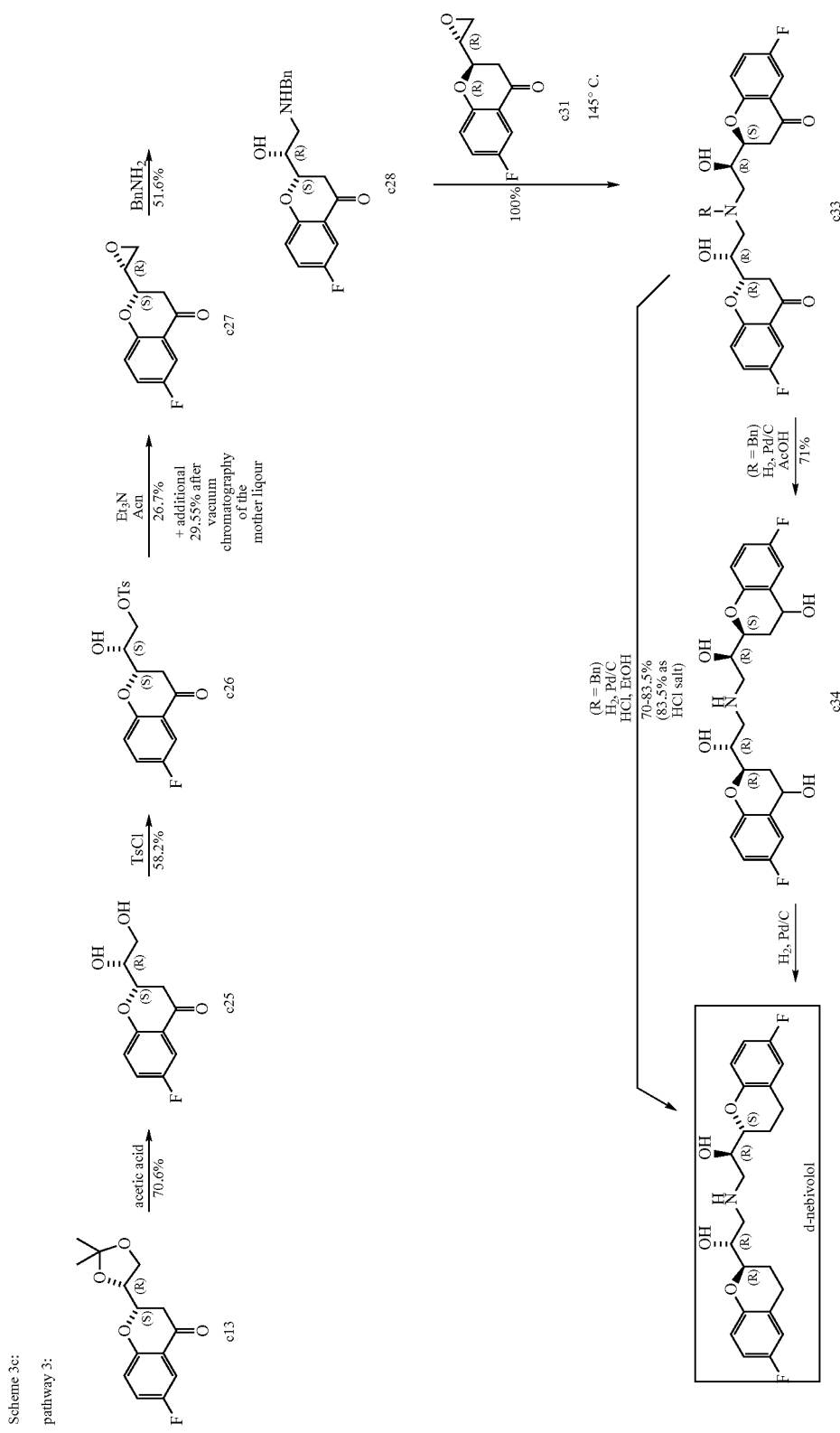

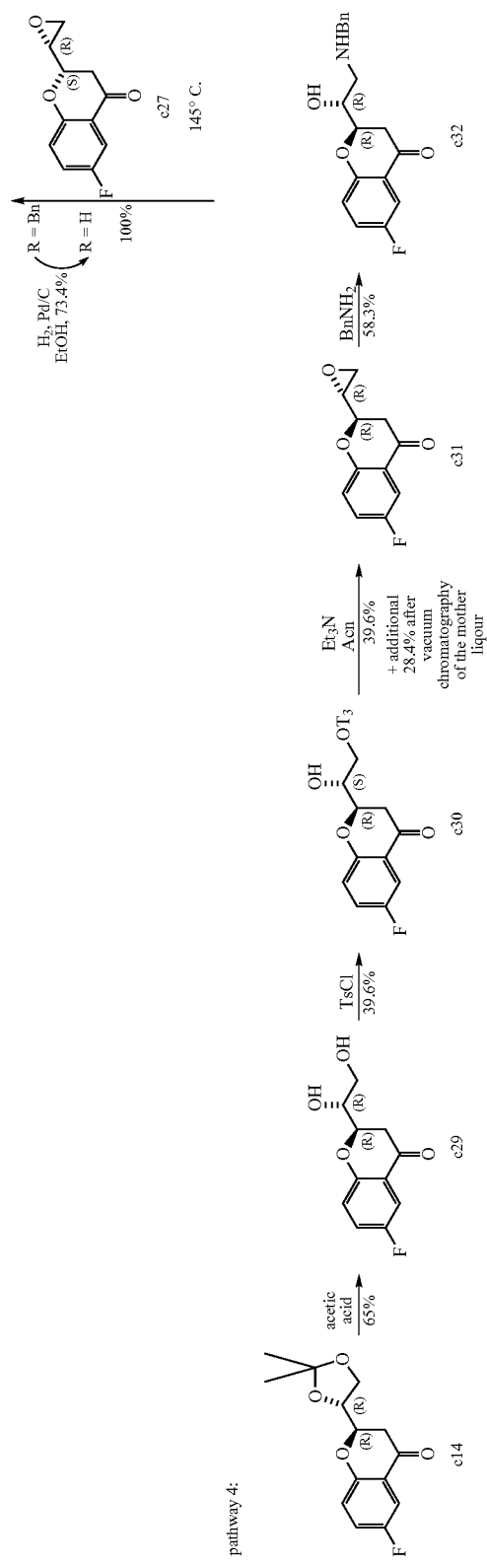

The strategy described in WO 2004/041805 has the following disadvantages:

1. Although the strategy is based on the use of all stereoisomers to synthesize either l-Nebivolol or d-Nebivolol, the main disadvantage is that up to 30 steps are necessary to get the racemic mixture by using all intermediates, which makes the production protracted and uneconomic; and 2. The steps of making compounds c23 from c18, c23 from c22, c33 from c28 and c33 from c32 are carried out without the use of a solvent at 145° C. (presumably after melting of the reactant). Such a procedure is not feasible on large scale.

d. Johannes et al., *J Am. Chem. Soc*. (1998), 120, 8340-8347

The Johannes et al. article describes an enantioselective preparation of d-Nebivolol (Scheme 4).

Scheme 4
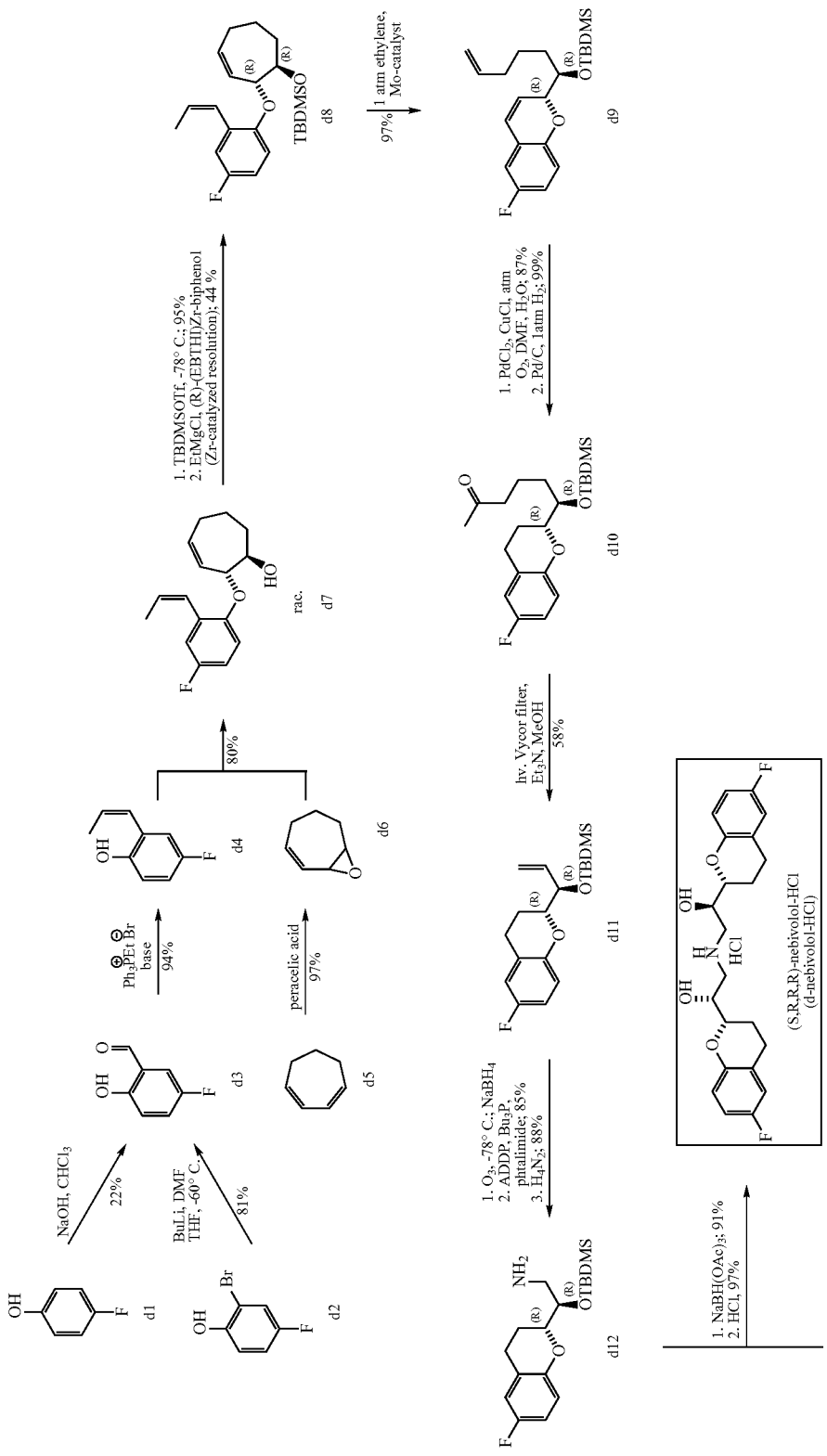

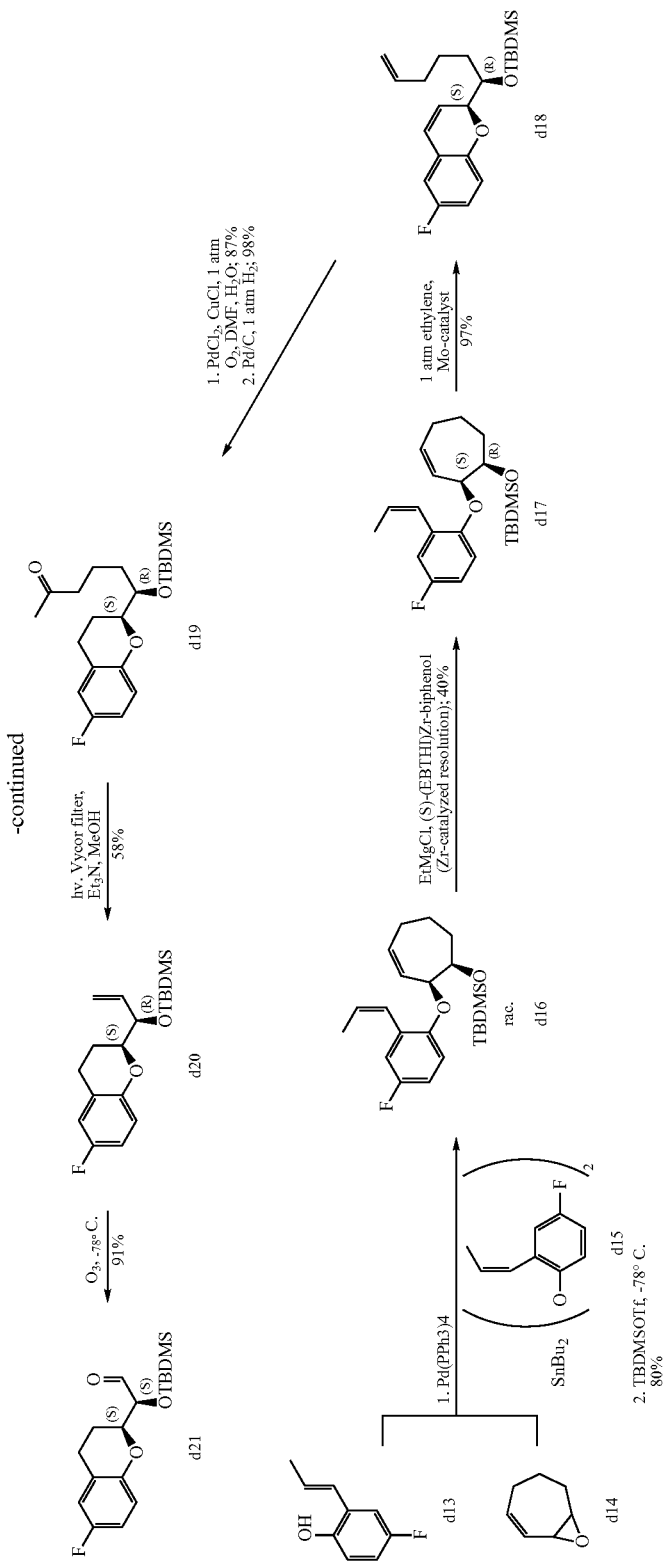

The strategy is based on the syntheses of the chiral chroman fragments d12 (R, R-configuration) and d21 (S, S-configuration) as key intermediates in convergent pathways which are finally coupled to give, after deprotection, d-Nebivolol. The essential step for the syntheses of these chiral chromans is the Zr-catalyzed kinetic resolution of the racemic intermediates d7 and d16.

According to the first pathway, the starting material for the preparation of chromane fragment d12 was the salicylic aldehyde d3, which was synthesized either by formylation of compound d1 or by reaction of the lithiated compound d2 at −60° C. with DMF. The allylic cycloheptene epoxide which could be obtained by epoxidation of cycloheptadiene was then reacted with aldehyde d4 to give the racemic compound d7 by a regioselective and stereoselective nucleophilic opening of epoxide d8. Protection of the hydroxyl group of d7 using TBSOT followed by treatment with 5 equiv EtMgCl and 10 mol % (R)-(EBTHI)Zr-binol delivered d8 in 44% yield and >98% ee. The Mo-catalyzed metathesis reaction under an ethylene atmosphere, followed by Wacker oxidation of the terminal double bond and subsequent catalytic hydrogenation, gave d10 in 83% overall yield. To synthesize d11 from d10, a photochemical Norrish type II cleavage was necessary. The following three-step sequence of ozonolytic cleavage, Mitsunobu reaction using tributylphosphine and phthalide followed by hydrazinolysis to remove the phthalimidyl group gave intermediate d12. The second pathway started with the synthesis of cis configured racemate d16, which was then resolved in the presence of the Zirconium catalyst (S)-(EBTHI)Zr-biphenol. The compound d17 was converted into compound d18 by Mo-catalyzed metathesis reaction. Wacker oxidation of the terminal double bond and subsequent catalytic hydrogenation delivered intermediate d19, which was further converted by a photochemical Norrish type II cleavage and ozonolysis into the aldehyde d21. D-Nebivolol was then obtained by reductive amination of compounds d12 and d21 followed by removal of the silyl ether protection groups.

The strategy described in the Johannes et al. article has the following disadvantages:

1. Preparation of aldehyde d3 occurs either in a low yield by formylation of d1 using chloroform in the presence of a base or requires low temperature by lithiation and formylation of compound d2. Furthermore, handling of n-Buli during a scale-up process requires special precautions;

2. The steps of preparing compounds d8 from d7 and d16 and d17 from d13/d14 also require low temperature (−78° C.) for the silylation. Furthermore, a difficult resolution step using a special commercially unavailable Zr-catalyst is necessary;

3. The steps of preparing compounds d10 to d11 and d19 to d20 require special equipment for the photochemical reaction (Norrish type 2 cleavage);

4. The step of preparing compound d12 from d11 requires low temperature (−78° C.) and special equipment for the ozonolysis; and 5. 16-20 steps are necessary for the synthesis of one Nebivolol enantiomer (d-form), but the racemic mixture is required; thus, additional steps are necessary to synthesize the corresponding 1-form (i.e., l-Nebivolol).

e. Chandrasekhar et al., *Tetrahedron* (2000), 56, 6339-6344

The Chandrasekhar et al. article describes another procedure for the enantioselective synthesis of d-Nebivolol (see Scheme 5).

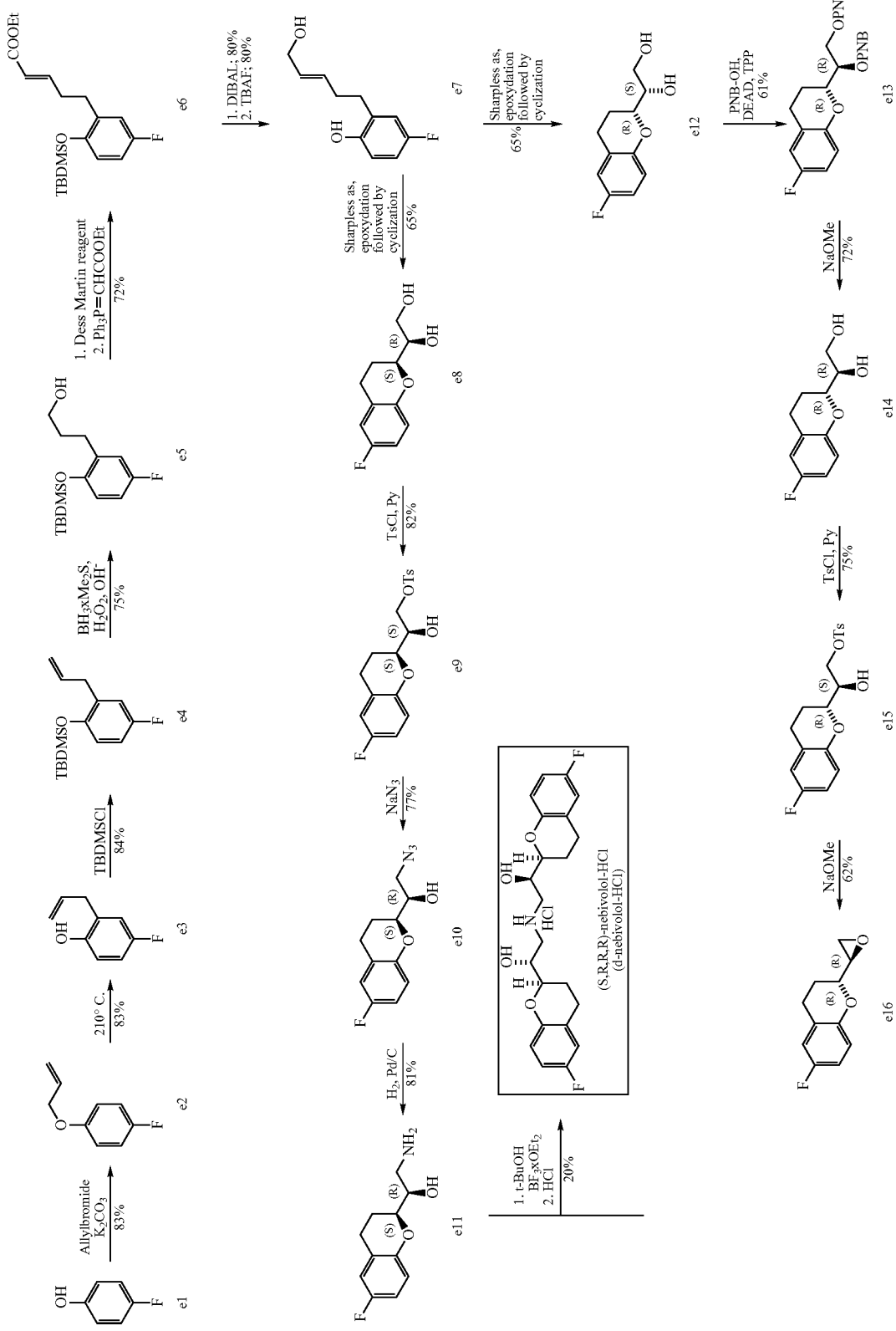
Scheme 5

The basis for the enantioselective strategy is the asymmetric one-pot Sharpless epoxidation of allyl alcohol e7 using (−)-DET and (+)-DET to provide both enantiomeric diols e8 and e12 after a cyclization step.

The starting compound was 4-fluoro-phenol e1, which was first converted into the allylether e2. Claisen rearrangement at 210° C. followed by protection of the phenol group (e3) with TBDMS-Cl gave the intermediate e4. The primary alcohol e5 was obtained by hydroboration and subsequent oxidative treatment using $H_2O_2$. This product was converted into the α,β-unsaturated ester e6 by one pot oxidation with Dess-Martin periodane and Wittig olefination. Afterwards, the compound e6 was reduced with DIBAL-H to the allyl alcohol e7. At this stage, the route was divided into two pathways each starting with the asymmetric Sharpless epoxidation and cyclization in one pot. On the first pathway, the diol e8 could be obtained in 65% yield by using (−)-DET. Selective tosylation of the primary alcohol e8 and substitution of e9 with azide followed by catalytical reduction of e10 gave the aminoalcohol e11. On the second pathway, the diol e12 was synthesized in an almost similar manner as diol e8 but with the exception that (+)-DET was used for the Sharples epoxidation to give the corresponding enantiomeric compound. Inversion at the $C_2$ carbon under Mitsunobu conditions with p-Nitrobenzoic acid gave the di-PNB protected compound e13. After removal of the protection groups, the diastereomeric diol e14 could be obtained. Selective tosylation of e14 and treatment of resulting e15 with a base yielded epoxide e16. The synthesis of d-Nebivolol hydrochloride could be completed by coupling of aminoalcohol e11 with epoxide e16 followed by transformation to the hydrochloride salt.

The strategy described in the Chandrasekhar et al. article has the following disadvantages:

1. Step of making compound e3 from e2 requires high temperature for the Claisen rearrangement, which is not practicable a in scale-up procedure;

2. Up to 16 steps are necessary to synthesize only one Nebivolol enantiomer, but the racemic mixture is required;

3. The last coupling step yields d-Nebivolol in a low yield (20%);

4. The Asymmetric Sharpless epoxidation is known to give non-enantiopure products. Therefore contaminations with other stereoisomers are likely. As already mentioned in WO 2004/041805, the described method for the measurement of the optical purity is not sufficient to determine such possible contaminations.

5. Almost all intermediates were purified by column chromatography because most intermediates are oily compounds.

In summary, multiple steps (>13 steps), the low yield, the usage of unusual catalyst, reaction conditions, special equipment and column chromatography for purification of the predominantly oily intermediates makes the available strategies and most of the steps too laborious and economically unsuitable for a commercial process.

Despite the above described efforts, there is a need for a new, efficient and commercially feasible process for the preparation of racemic Nebivolol having an improved overall yield.

All references cited herein are incorporated herein by reference in their entireties.

BRIEF SUMMARY OF THE INVENTION

The present invention provides new compounds and intermediates as well as processes that can be used directly for the selective synthesis of Nebivolol or racemic ([2S*[R*[R*]]]]- and ([2R*[S*[S[S*]]]]-(±)-alpha,alpha' -[imino-bis(methylene)]bis[6-fluoro-chroman-2-methanol] of the formula (I)

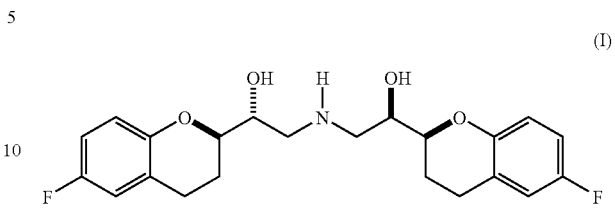

and its pure ([2S[2R*[R[R*]]]]- and ([2R*[S*[S[S*]]]]-enantiomeric compounds and pharmaceutically acceptable salts thereof Accordingly, a process for preparing racemic [2S*[R*[R*]]]] and [2R*[S*[S*[S*]]]]-(±)α,α'-[iminobis(methylene)]bis[6-fluoro-3,4-dihydro-2H-1-benzopyran-2-methanol] and pharmaceutically acceptable salts thereof includes (a) providing a compound of formula (VIII)

as a diastereomerically pure compound comprising at least 95% of RS/SR configuration or RR/SS configuration, wherein PG is hydrogen or an amine protecting group, wherein the amine protecting group is at least one of an allyl group or an aryl-$C_1$ alkyl group;

(b) providing a racemic compound of formula (V)

wherein LG is a member selected from the group consisting of chloro, bromo, iodo, alkylsulfonyloxy and arylsufonyloxy;

(c) N-alkylating the compound of formula (Vifi) with the compound of formula (V), wherein said N-alkylating is carried out in an inert organic solvent in a presence of a base and optionally in the presence of a catalyst to give a compound of formula (IX)

a compound of formula (IX') which is a cyclic semi-ketal form of the compound of formula (IX)

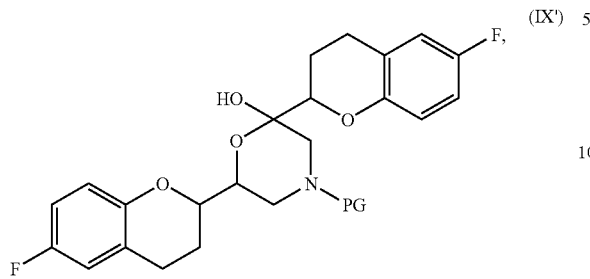

or a mixture thereof, wherein the compound of formula (IX) and the compound of formula (IX') are mixtures of diastereomers;

(d) separating diastereomers of the compound of formula (IX) or the compound of formula (IX') by fractional crystallization after salt formation or after derivatization to obtain PG is H then omitting said deprotecting, to obtain a compound of formula (I) substantially pure diastereomers of formula (IX) or formula (IX') having at least 50% of a RSS/SRR or RRS/SSR configuration;

(e) reducing substantially pure diastereomers of formula (IX) or formula (IX') having a RSS/SRR or RRS/SSR configuration to give a compound of formula (X)

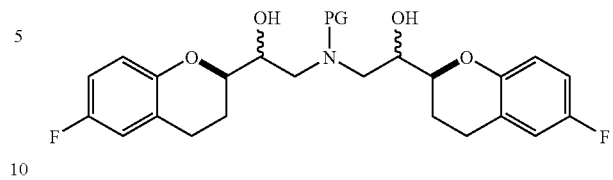

as a RSSS/SRRR diastereomeric mixture having a ratio of a RSSS/SRRR diastereomeric configuration to a SRSR or RRSS diastereomeric configuration, wherein said ratio is at least 1;

(f) deprotecting the compound of formula (X), provided that PG is not H and if PG is H then omitting said deprotecting, to obtain a compound of formula (I) or pharmaceutically acceptable salts thereof; and (g) removing a RSRS or RRSS diastereomeric configuration of the compound of formula (I) or pharmaceutically acceptable salts thereof if present by recrystallization or by a slurry to give racemic [2S*[R*[R*[R*]]]] and [2R*[S*[S*[S*]]]]-(±)α,α'-[iminobis(methylene)]bis[6-fluoro-3,4-dihydro-2H-1-benzopyran-2-methanol] or pharmaceutically acceptable salts thereof.

Further provided is a racemic ([2S*[R*[R*[R*]]]]- and ([2R*[S*[S*[S*]]]]-(±)-alpha,alpha'-[imino-bis(methylene)]bis[6-fluoro-chroman-2-methanol] of the compound of the formula (I) prepared by the process described above.

The preferred embodiment of the process is shown in Scheme 6a.

Scheme 6a:

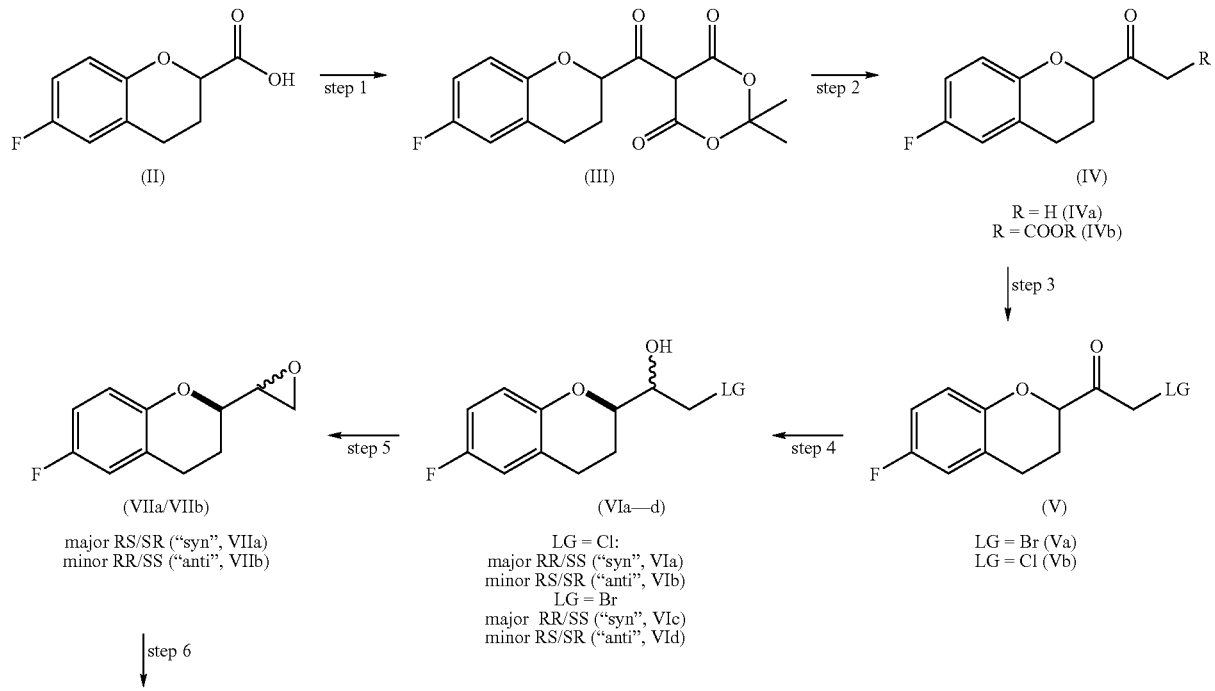

-continued

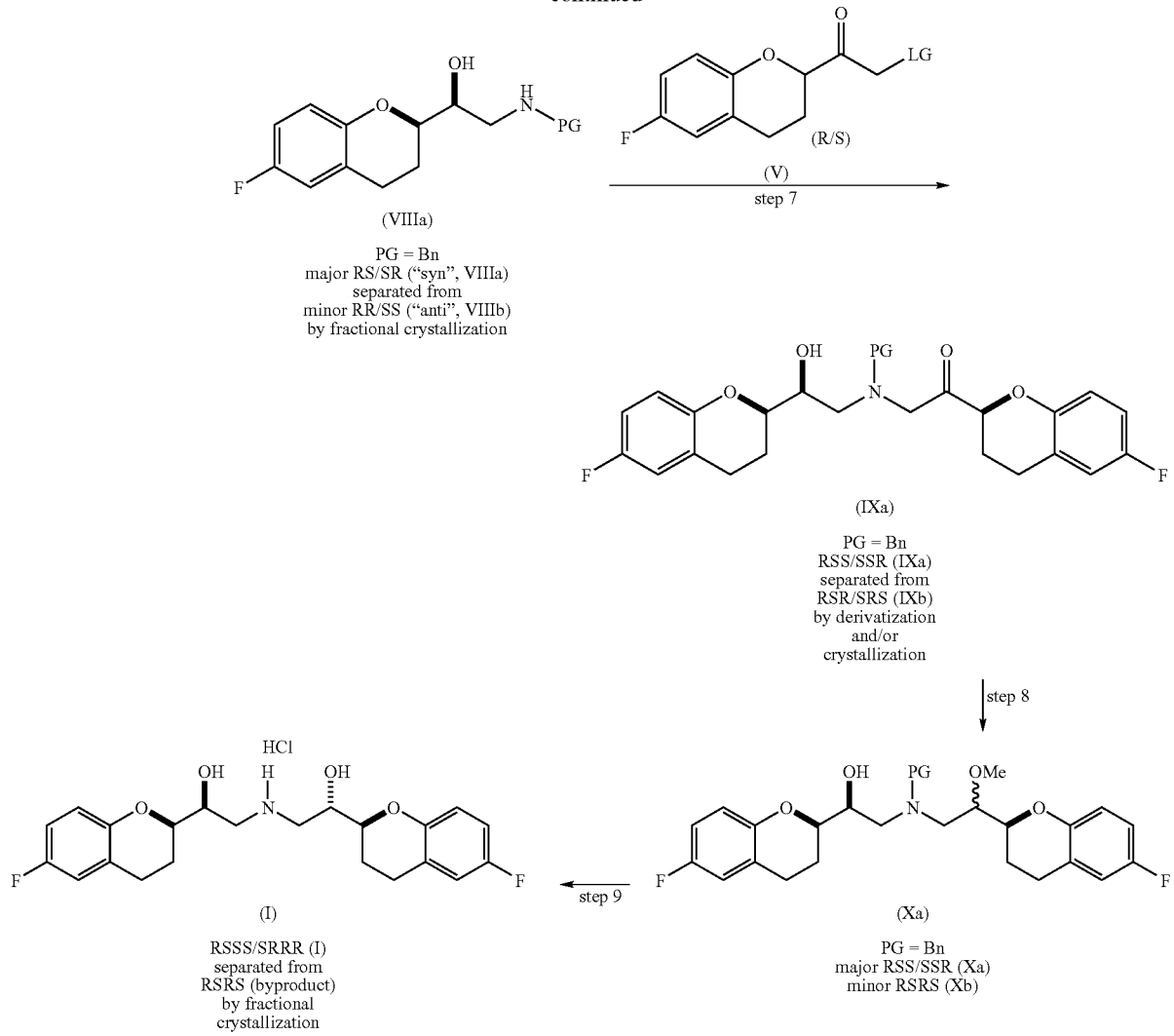

The starting compound is the 6-fluoro-chroman-2-carboxylic acid II, which is converted by appropriate transformations (steps 1, 2, and 3) into compound V bearing a suitable leaving group (LG). A selective reduction of compound V, followed by epoxide formation and substitution with a protected amine, gives compound VIIIa after fractional crystallization. In this case, the order of the transformations may be changed without the need for epoxide formation. Coupling of compound VIIIa with compound V gives a diastereomeric mixture of compounds IXa and Xb, whereupon compound IXa is selectively isolated and almost selectively reduced to a mixture of compounds Xa (major) and Xb (minor). This mixture is then deprotected, and after salt formation using HCl, racemic Nebivolol hydrochloride I is selectively crystallized. The overall yield is 8%; however, additional amounts of compound V used for step 7 were not taken into account.

In a preferred embodiment, the protecting group is a benzyl group. In certain embodiments, the leaving group is a chloro or bromo group.

In certain embodiments of the process, in step (b) the compound of formula (V) is provided in the amount of about 1.0 to about 1.5 equivalents.

In certain embodiments of the process, in step (c) the organic solvent is a polar aprotic solvent selected from the group consisting of DMF, DMA and NMP.

In certain embodiments of the process, in step (c) the base is at least one of tertiary amines, alkali metal carbonate or alkali metal hydrogen carbonate. Preferably, the base is sodium hydrogen carbonate. Preferably, about 1.5 to about 2.5 equivalents of the base are used.

In certain embodiments of the process, in step (c) catalyst is at least one of alkali metal bromides, alkali metal iodides, tetraalkylammonium bromides or tetraalkylammonium iodides. Preferably, the catalyst is sodium bromide. Preferably, about 0.1 to about 0.25 equivalents of the catalyst are used and most preferably, 0.15 equivalents of the catalysts are used.

In certain embodiments, in step (c) said N-alkylation is carried out at a temperature between about room temperature and about 80° C.

In certain embodiments, in step (d) the fractional crystallization is carried out in a solvent. Preferably, the solvent is acetonitrile. Preferably, a free amine is used for the fractional crystallization. In certain embodiments, about 0.4/n to about 0.6/n equivalents of the silylating reagent are used and n is an amount of transferred silyl groups per the silylating reagent. Preferably, the silylating reagent is at least one of trimethylsilyl chloride (TMSCl), HMDS or BSU.

In certain embodiments, in step (d) a silylation reagent is used for derivatization prior to the fractional crystallization from the solvent. Preferably, the derivatization is carried out in the presence of about 1.0 to about 2.0 equivalents of a base. Preferably, the base is imidazole.

In certain embodiments, in step (d) said separating the diastereomers of the compound of formula (IX) or the compound of formula (IX') is carried out in acetonitrile, MTBE, cyclohexane or mixtures thereof.

In certain embodiments, in step (e), said reducing is carried out for the RSS/SRR configuration the compound of formula (IX) or the compound of formula in a solvent with alkali borohydride, tetrabutylammonium borohydride, alkali-SELECTRIDE or zinc borohydride, optionally in a presence of a Lewis acid. In certain embodiments, the Lewis acid is at least one of Ti(OAlkyl)$_4$, ZnCl$_2$ alkali halide or alkaline earth halide. Preferably, the solvent is at least one of an ether, an alcohol or a halogenated hydrocarbon. In certain embodiments, said reducing is carried out at temperatures between about −20° C. and about room temperature.

In certain embodiments, in step (f) said deprotecting is carried out by catalytic hydrogenation.

In certain embodiments, in step (g) said purifying the compound of formula (I) is done by a slurry of its hydrochloride salt in a solvent. Preferably, the slurry is carried out in methanol as the solvent.

In certain embodiments said providing the compound of formula (VIII) includes:

(i) reducing the racemic compound of formula (V) in a solvent and optionally in a presence of a Lewis acid, wherein LG is bromine or chlorine to give a diastereomeric mixture of compounds of formula (VI)

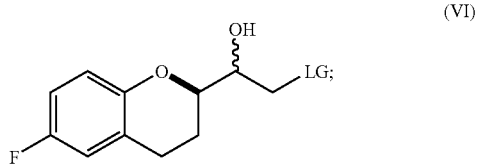

(VI)

(ii) forming a mixture of diastereomers of a compound of formula (VII)

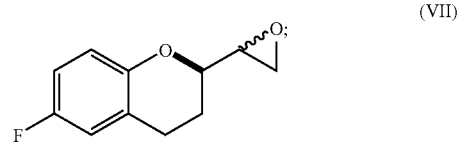

(VII)

(iii) reacting diastereomers of the compound of formula (VII) with NH$_2$PG to give a mixture of diastereomers of the compound of formula (VIII)

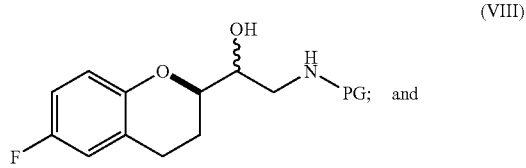

(VIII)

(iv) separating diastereomers of the compound of formula (VIII) from the mixture of diastereomers by the fractional crystallization optionally after formation of a salt. In a preferred embodiment, PG is a benzylic group.

In certain embodiments, at least one of the diastereomers of the compound of formula VIII having a RR/SS or RS/SR configuration is isolated.

In another aspect of the present invention, a recycling process of undesired diastereomers produced during the process is provided, which reduces the costs and makes the process of making Nebivolol more efficient. Specifically, during the selective preparations of compounds VIIIa and Xa, the undesired diastereomers are formed as minor products. Thus, recycling of the waste presents an economical and ecological advantage over prior methods of making Nebivolol.

Also, the alkylation of compound VIIIa with compound V forms a diastereomeric mixture (a 1/1 mixture of IXa and IXb), wherein the recycling step enables the transformation of the undesired form IXb either by selective cleavage into compound VIIIa or by a suitable epimerization step into a mixture of compounds IXa and IXb followed by selective isolation of desired diastereomer IXa.

In certain embodiments of the process, recycling the RR/SS configuration of the compound of formula (VII) is conducted, wherein said recycling comprises:

providing the RR/SS configuration of the compound of formula (VIII) with a protective group; and inversion of the alcohol configuration to provide the SR/RS configuration of formula VIII.

In certain embodiments, in step i) the reducing agent is selected from alkali borohydride, tetraalkylammonium borohydride, zinc borohydride, alkali triacetoxyborohydride, SUPERHYDRIDE, RED-AL, alkali-SELECTRIDE or coordinated borohydrides. In certain embodiments, in step i) the reduction is carried out under Meerwein Pondorf Verley conditions. In certain embodiments, in step i) said reducing is carried out by catalytic hydrogenation. In certain embodiments, in step i) the Lewis acid is a member selected from the group consisting of alkali or alkaline earth chlorides, zinc chloride, titanium(IV) alkoxide, and aluminium trialkoxide. In certain embodiments, in step i) said reducing is carried out under conditions which give an RR/SS isomer of the compound of formula (VI) in excess. In certain embodiments, in step i) said reducing is carried out at a temperature between about −78° C. and about room temperature. Preferably, said reducing is carried out at the temperature between −20° C. and room temperature. In certain embodiments, in step i) the solvent is a member selected from the group consisting of alcohols, ethers, halogenated hydrocarbons and aromatic solvents.

In certain embodiments, in step ii) said forming the mixture of diastereomers of the compound of formula (VII) is carried out in a solvent and in a presence of a base. Preferably, the solvent is an alcohol and the base an alkali alkoholate. Preferably, 1.0 to 2.0 equivalents of the base are used.

In certain embodiments, in step ii) said forming of the mixture of diastereomers of the compound of formula (VII) is carried out at temperatures between 0° C. and 40° C.

In certain embodiments, in step iv) the fractional crystallization is carried out in toluene, acetonitrile, a $C_1$-$C_3$-alcohol, an ether or mixtures thereof. Preferably, the $C_1$-$C_3$-alcohol is 2-propanol and the ether is at least one of diisopropylether or MTBE.

In certain embodiments, said providing the racemic compound of formula (V) comprises:

(1) transforming a compound of formula (II)

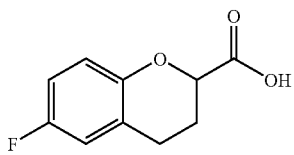

into an activated acid derivative;

(2) reacting the activated acid derivative with Meldrums acid in a presence of a base to give a compound of formula (III)

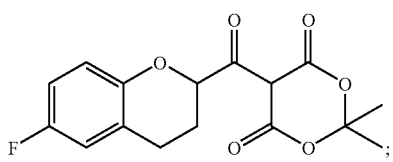

(3) converting the compound of formula (III) into a compound of formula (IV)

(IV)

R = H (IVa)
R = COOR' (IVb)

wherein R is hydrogen or COOR' and wherein R' is $C_1$-$C_6$ alkyl or aryl-$C_1$ alkyl; and (4) halogenating the compound of formula (IV) and optionally conducting hydrolysis and decarboxylation to give the compound of formula (V).

In certain embodiments, in step (1) the carboxylic acid is transformed into a corresponding acid chloride.

In certain embodiments, in step (2) the base is a tertiary amine. In certain embodiments, 1 to 3 equivalents of Meldrums acids are used. In certain embodiments, in step (2), the reaction temperature is between about −10° C. and about +30° C.

In certain embodiments, in step (3) the compound of formula (III) is hydrolyzed in a mixture of an organic acid and water to give a compound of formula (IV) wherein R is H. In a preferred embodiment, the organic acid is acetic acid and the hydrolysis is carried out at a reflux temperature. In certain embodiments, in step (3) the compound of formula (IV) having R as COOR' and R' as $C_1$-$C_6$ alkyl or aryl-$C_1$ alkyl is prepared by an alkoholysis of the compound of formula (III). Preferably, the alkoholysis is carried out with ethanol and tert-butanol. Preferably, the alkoholysis is carried out at temperatures between about 70° C. and about 80° C.

In certain embodiments, in step (3) the solvent is at least one of alcohol or toluene.

In certain embodiments, in step (4) before the halogenation is carried out, the compound of formula (IV) wherein R is H is transformed to a corresponding silylenol ether having the terminal double bond by silylation. In certain embodiments, the silylation is done by a kinetically controlled deprotonation using LDA followed by silylation at about −78° C. to about −40° C. Preferably, the silylation is done at −78° C. to −70° C. In a preferred embodiment, the silylating reagent is TMSCl.

In certain embodiments, in step (4) after the transformation to the silylenol ether, the halogenation is carried out by using a brominating reagent. Preferably, the bromination reagent is NBS.

In certain embodiments, in step (4) the compound of formula (IV) wherein R is COOR' is first halogenated and then transformed into the compound of formula (V) by ester hydrolysis followed by decarboxylation. Preferably, the halogenation is done in a presence of a catalyst. In certain embodiments, about 1.0 to about 1.5 equivalents of NBS, NCS or $SO_2Cl_2$ are used as halogenation reagents. In certain embodiments, about 0.2 equivalents to 0.4 equivalents of $Mg(ClO_4)_2$ are used as a catalyst.

In certain embodiments, in step (4) said halogenating is carried out at temperatures between 0° C. and about room temperature.

In certain embodiments, in step (4) after said halogenating, the hydrolysis of the ester followed by decarboxylation is carried out in an aqueous organic acid solution. Preferably, the organic acid is at least one of trifluoro acetic acid, formic acid and acetic acid. Preferably, the hydrolysis and decarboxylation are carried out at temperatures between about 75° C. and about 90° C.

In certain embodiments, the process further includes recycling an RSR/SRS or RRR/SSS configuration of the compound of formula (IX) or (IX'), wherein said recycling comprises:

epimerizing the RSR/SRS or RRR/SSS configuration of the compound of formula (IX) or (IX') to give a mixture of the RSS/SRR configuration containing the RSR/SRS configuration of diastereomers of formula (IX) or formula (IX') or RRS/SSR configuration containing the RRR/SSS configuration of diastereomers of formula (IX) or formula (IX') and separating the mixture by fractional crystallization after salt formation or after derivatization to obtain substantially pure diastereomers of formula (IX) or formula (IX') having the RSS/SRR or RRS/SSR configuration.

In certain embodiments, the process further includes recycling an RSR/SRS or RRR/SSS configuration of the compound of formula (IX) or (IX') wherein said recycling comprises:

cleaving the RSR/SRS or RRR/SSS configuration of the compound of formula (IX) or (IX') to give a mixture comprising an RS/SR or RR/SS configuration of diastereomers of formula (VIII); and separating the RS/SR or RR/SS configuration of diastereomers of formula (VIII).

Further provided is a compound of formula (III)

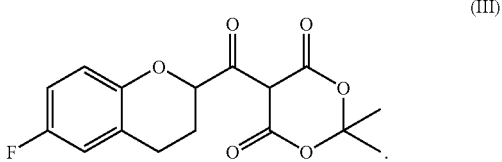

Further provided is a compound of formula (IV)

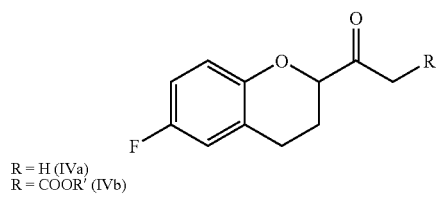

R = H (IVa)
R = COOR' (IVb)

wherein R is hydrogen or COOR' and R' is $C_1$-$C_6$ alkyl or aryl-$C_1$ alkyl.

Further provided is a compound of formula (V)

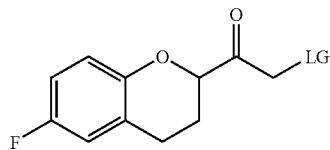

wherein LG is bromine or chlorine.

Further provided is a compound of formula (VI)

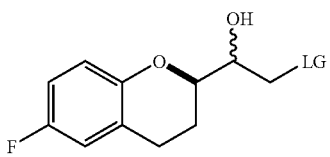

wherein LG is bromine or chlorine.

Further provided is a compound of formula (IX)

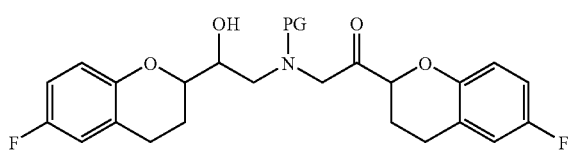

or its cyclic semi-katal form having the formula (IX')

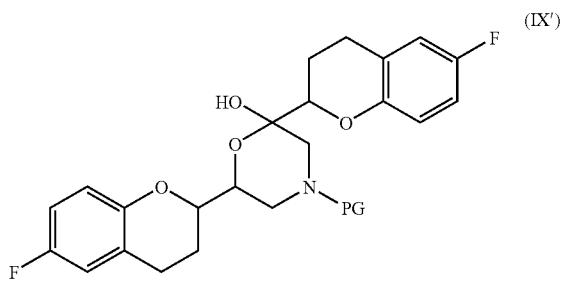

wherein PG is protecting group selected from hydrogen, allyl and aryl-$C_1$ alkyl.

Further provided is a compound of formula (IX) having a RSS/SRR configuration

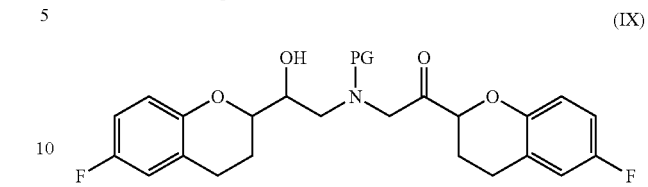

or its corresponding cyclic semi-ketal form (IX')

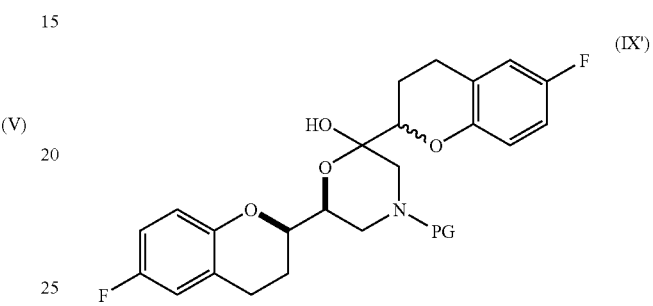

wherein PG is a benzylic group.

Also provided is a process for preparing racemic [2S*[R*[R*[R*]]]] and [2R*[S*[S*[S*]]]]-(±)α,α'-[iminobis(methylene)]bis[6-fluoro-3,4-dihydro-2H-1-benzopyran-2-methanol] and pharmaceutically acceptable salts thereof, the process comprising: providing a compound of formula (IX); and reducing the compound of formula (IX) to obtain a compound of formula (X) having at most 50% of a stereoisomer having a RSRS configuration. This process further comprises providing a compound of formula (VIII) and a compound of formula (V).

In accordance with the invention, enantiomerically pure Nebivolol (l-Nebivolol or d-Nebivolol) may also be obtained, e.g., after resolution of compound II (see Schemes 6b and 6c). Each of the enantiomers (S-II and R-II) may be transformed by the same methods as described for the corresponding racemic compound II (compare Scheme 6a) to give the first key intermediates S-V and R-V. L-Nebivolol-Hydrochloride (Scheme 6b) may be then prepared by the synthesis of R-VIIIa starting from R-V, followed by coupling with S-V (step 11), selective reduction (step 12), deprotection and salt formation (step 13). D-Nebivolol-Hydrochloride may be prepared in the same manner with the exception that, in contrast to the synthesis of l-Nebivolol, the enantiomeric intermediate S-VIIIa will be prepared from S-V and then coupled with R-V (Scheme 6c, step 11). Selective reduction (step 12) followed by deprotection and salt formation will give d-Nebivolol-Hydrochloride.

It will be apparent to one skilled in the art that various changes and modifications of these routes may be used for enantioselective syntheses of l- or d-Nebivolol. Therefore, the use of intermediates for the enantioselective synthesis of l- or d-Nebivolol, prepared according to Schemes 6b and 6c, is not limited to the described routes. For example, the epoxides R-VIIa, R-VIIb, S-VIIa and S-VIIb (prepared from the key intermediates R-V or S-V) may also be used directly for the synthesis of each Nebivolol enantiomer, e.g., according to the route described in Scheme 2. Whether the epoxides R-VIIa, R-VIIb, S-VIIa and S-VIIb are prepared as major or minor compounds depends on the reducing agent.

Scheme 6b:
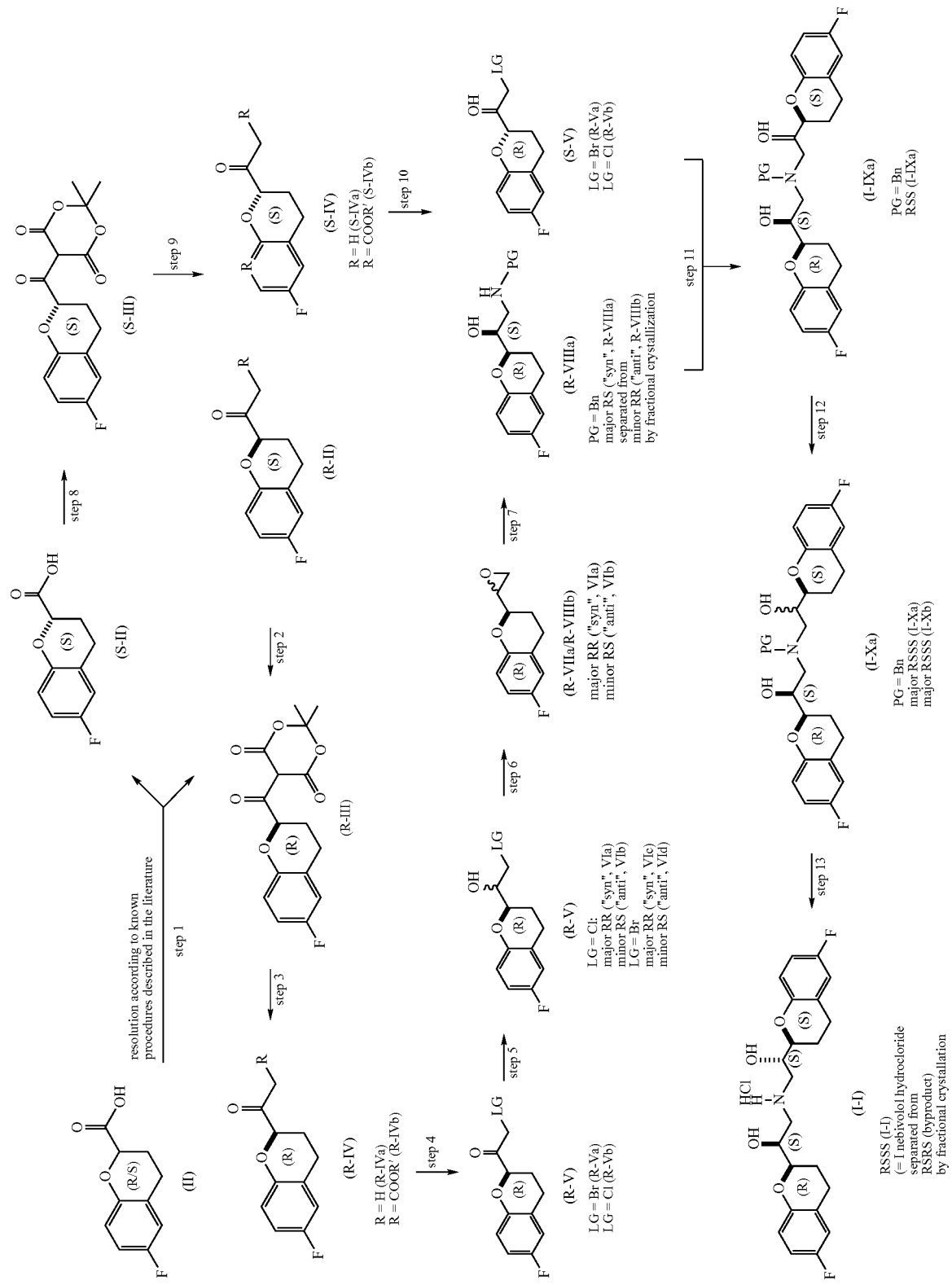

Scheme 6c:
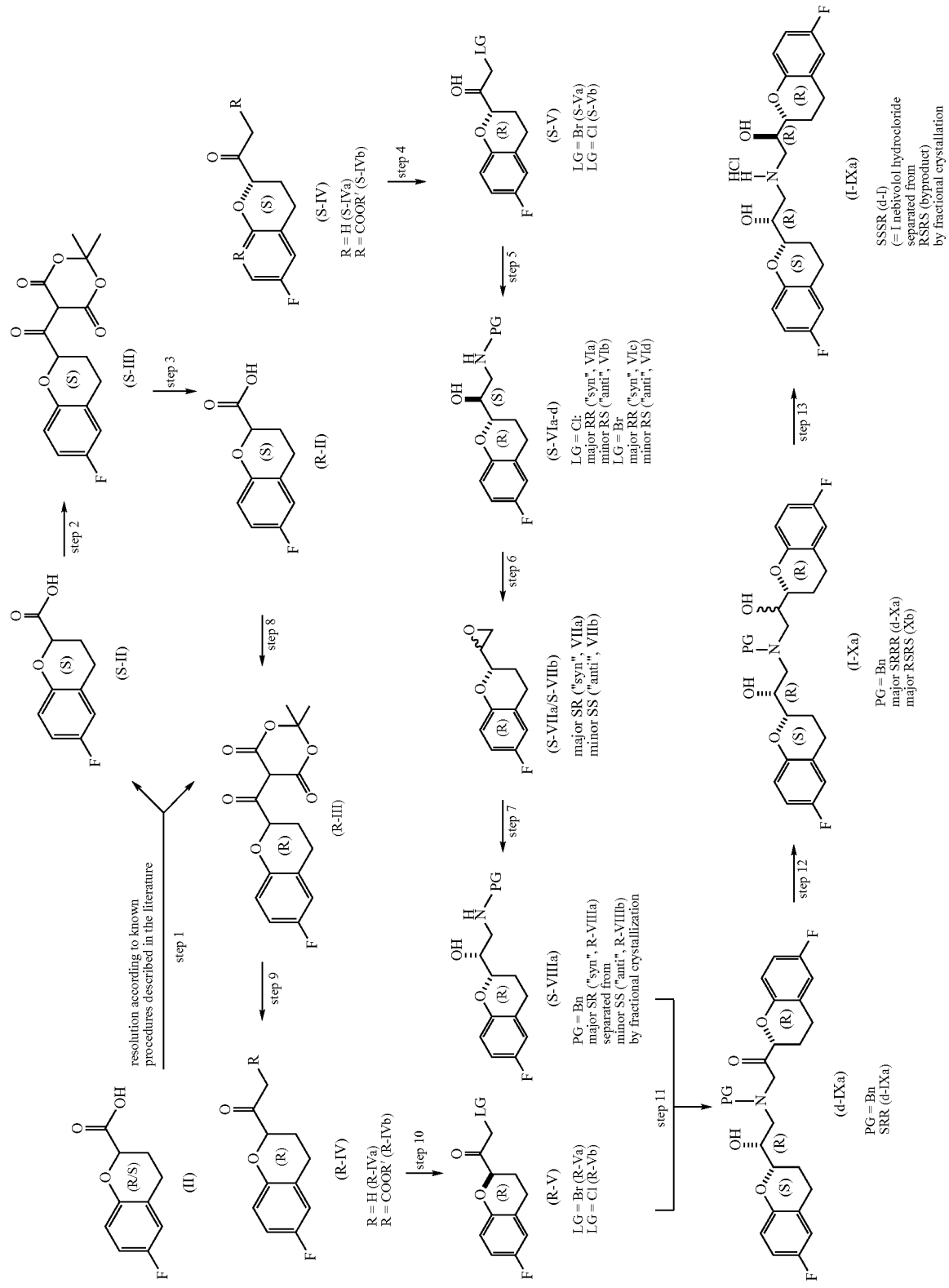

The process of preparing a compound of formula (I) as a racemic mixture or an enantiomerically pure form and pharmaceutically acceptable salts thereof includes:

(a) resolving a compound of formula (II)

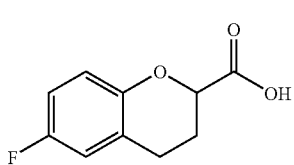
(II)

to obtain an S configuration and an R configuration of the compound of formula (II);

(b) converting the S configuration of the compound of formula (II) into an S configuration of a compound of formula (V)

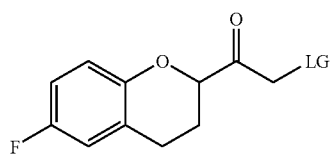
(V)

wherein LG is a member selected from the group consisting of chloro, bromo, iodo, alkylsulfonyloxy and arylsufonyloxy, via formation of an S configuration of a compound of formula (III) and an S configuration of a compound of formula (IV);

(c) converting the R configuration of the compound of formula (II) into an R configuration of the compound of formula (V) via formation of an R configuration of the compound of formula (III) and an R configuration of the compound of formula (IV);

(d) providing a compound of formula (VIII)

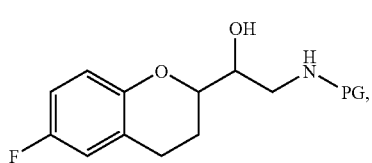
(VIII)

wherein PG is hydrogen or an amine protecting group, wherein the amine protecting group is at least one of an allyl group or an aryl-$C_1$ alkyl group and wherein the compound of formula (VIII) is enantiomeric compound having an RS or SR configuration;

(e) conducting N-alkylation of (i) the RS configuration of compound of formula (VIII) with the S configuration of compound of formula (V) or (ii) the SR configuration of compound of formula (VIII) with the R configuration of compound of formula (V), provided that said N-alkylation is carried out in an inert organic solvent in a presence of a base and optionally in the presence of a catalyst to give a RSS or SRR enantiomeric form of a compound of formula (IX)

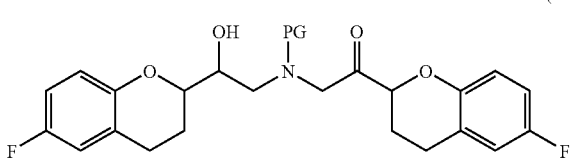
(IX)

or a RSS or SRR enantiomeric form of a compound of formula (IX') which is a cyclic semi-ketal form of the compound of formula (IX)

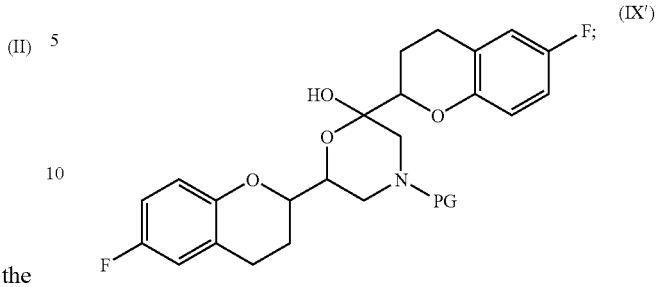
(IX')

(f) reducing at least one of the RSS or SRR enantiomeric form of the compound of formula (IX) or formula (IX') to give at least one RSSS or SRRR enantiomeric form of a compound of formula (X)

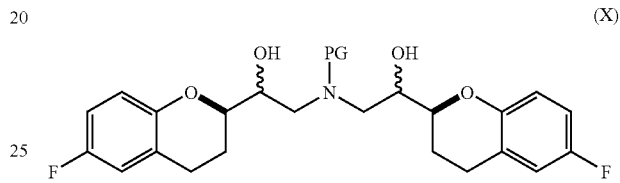
(X)

(g) deprotecting the at least one of the RSSS or SRRR enantiomeric form of the compound of formula (X), provided that PG is not H and if PG is H then omitting said deprotecting, to obtain the compound of formula (I) or pharmaceutically acceptable salts thereof; and (h) removing a RSRS diastereomeric configuration of the compound of formula (I) or pharmaceutically acceptable salts thereof if present as a byproduct by recrystallization or by a slurry to give at least one of ([2S*[R*[R*[R*]]]]- and ([2R*[S*[S*[S*]]]]-enantiomer of the compound of the formula (I) and pharmaceutically acceptable salts thereof; and (i) optionally combining ([2S*[R*[R*[R*]]]]- and ([2R*[S*[S*[S*]]]]-enantiomer of the compound of the formula (I) and pharmaceutically acceptable salts thereof to form racemic ([2S*[R*[R*[R*]]]]- and ([2R*[S[*[S*]]]]-(±)-alpha,alpha'-[imino-bis(methylene)]bis[6-fluoro-chroman-2-methanol] of the compound of the formula (I) and pharmaceutically acceptable salts thereof.

Also provided is a process for preparing racemic [2S*[R*[R*[R*]]]] and [2R*[*[S*[S*]]]]-(±)α,α'-[iminobis(methylene)]bis[6-fluoro-3,4-dihydro-2H-1-benzopyran-2-methanol] and pharmaceutically acceptable salts thereof, the process comprising:

(a) providing a compound of formula (VIII) as a diastereomer having RR/SS configuration, wherein PG is hydrogen or an amine protecting group, wherein the amine protecting group is at least one of an allyl group or an aryl-$C_1$ alkyl group;

(b) providing a racemic compound of formula (V) wherein LG is a member selected from the group consisting of chloro, bromo, iodo, alkylsulfonyloxy and arylsufonyloxy;

(c) N-alkylating the compound of formula (VIII) with the compound of formula (V), wherein said N-alkylating is carried out in an inert organic solvent in a presence of a base and optionally in the presence of a catalyst to give a compound of formula (IX), a compound of formula (IX') which is a cyclic semi-ketal form of the compound of formula (IX), or a mixture thereof, wherein the compound of formula (IX) and the compound of formula (IX') are mixtures of diastereomers having a RRR/SSS and RRS/SSR configuration;

(d) separating diastereomers of the compound of formula (IX) or the compound of formula (IX') by fractional crystallization after salt formation or after derivatization to obtain substantially pure diastereomers of formula (IX) or formula (IX') having at least 50% of the RRR/SSS or RRS/SSR configuration;

(e) reducing the substantially pure diastereomers of formula (IX) or formula (IX') having a RRS/SSR configuration to give a compound of formula (X) as a RSSS/SRRR diastereomeric mixture having a ratio of a RSSS/SRRR diastereomeric configuration to a SRSR or RRSS diastereomeric configuration, wherein said ratio is at least 1;

(f) deprotecting the compound of formula (X), provided that PG is not H, to obtain a compound of formula (I) or pharmaceutically acceptable salts thereof; and (g) removing a RSRS diastereomeric configuration of the compound of formula (I) or pharmaceutically acceptable salts thereof if present by recrystallization or by a slurry to give racemic [2S[2R*[R[R*]]]] and [2R[2S*[S[S*]]]]-(±)α,α'-[iminobis(methylene)]bis[6-fluoro-3,4-dihydro-2H-1-benzopyran-2-methanol] or pharmaceutically acceptable salts thereof.

In certain embodiments, the process further comprises cleaving the RRR/SSS configuration of the compound of formula (IX) or the compound of formula (IX') to give the compound of formula (VIII) as the diastereomer having RR/SS configuration.

In one variant, the process further comprises epimerizing the RRR/SSS configuration of the compound of formula (IX) or the compound of formula (IX') to give said mixtures of diastereomers having the RRR/SSS and RRS/SSR configuration of the compound of formula (IX) or the compound of formula (IX'). In yet another variant of the above variant, the process further comprises cleaving the RRR/SSS configuration of the compound of formula (IX) or the compound of formula (IX') to give the compound of formula (VIII) as the diastereomer having RR/SS configuration.

Also provided is a process of making a compound of formula (VIII)

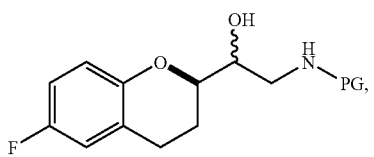

(VIII)

the process includes (i) providing a racemic compound of formula (V)

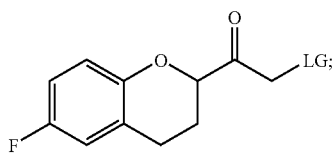

(V)

(i) reducing the racemic compound of formula (V) in a solvent and optionally in a presence of a Lewis acid, wherein LG is bromine or chlorine to give a diastereomeric mixture of a compound of formula (VI)

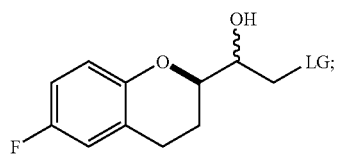

(VI)

(ii) forming a mixture of diastereomers of a compound of formula (VII)

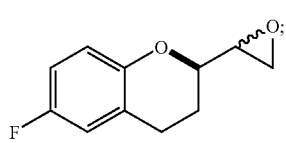

(VII)

(iii) reacting diastereomers of the compound of formula (VII) with NH$_2$PG to give the compound of formula (VIII) as a mixture of diastereomers; and (iv) optionally separating diastereomers of the compound of formula (VIII) from the mixture of diastereomers by the fractional crystallization.

Novel compounds discovered by the inventors include the following

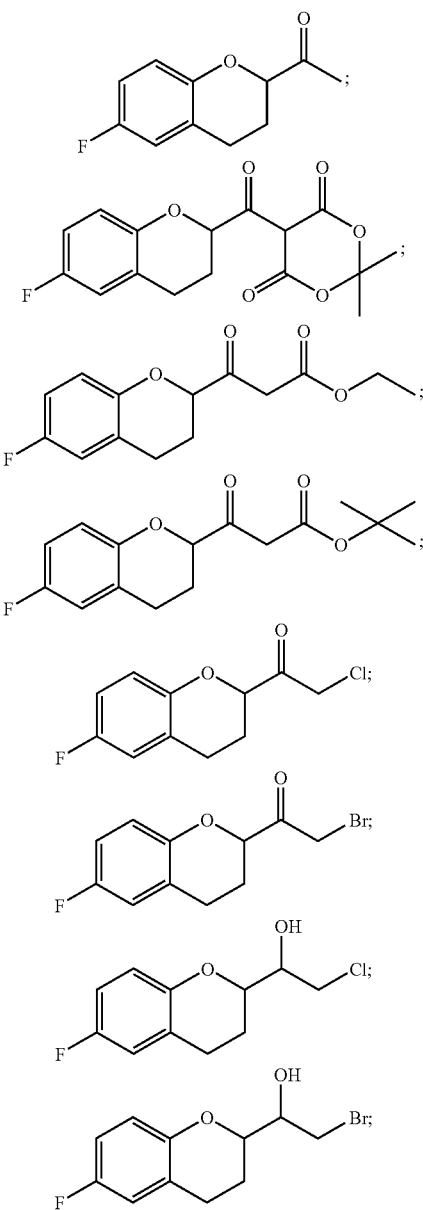

-continued

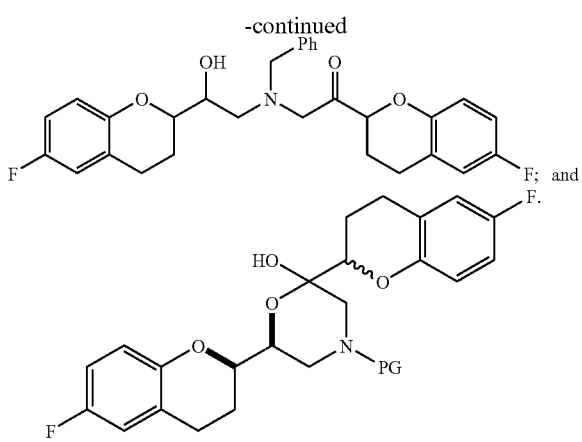

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

Figure 1A:
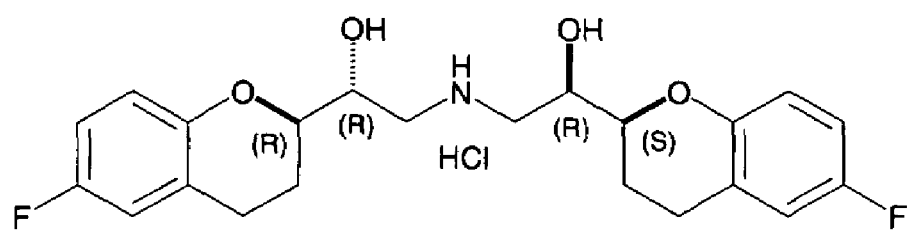
FIG. 1A depicts a structural formula of d-Nebivolol-HCl.
Figure 1B:
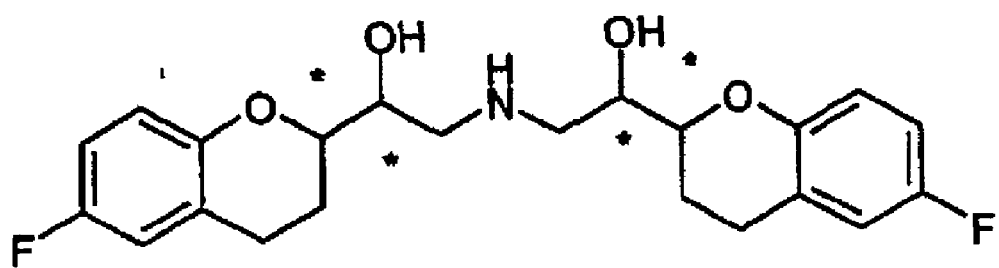
FIG. 1B depicts a structural formula of racemic Nebivolol.

The present invention provides new compounds and methods for the synthesis of a racemic Nebivolol and its pharmaceutically acceptable salts as well as an enantiomerically pure Nebivolol and its pharmaceutically acceptable salts. This invention was driven by a desire to create a more efficient process having fewer reaction steps by avoiding steps of separating enantiomers prior to making a racemic mixture. One example of separating enantiomers is described in WO 2004/041805 (Scheme 3b). Since all enantiomers were separated during early stages of the process, up to 30 steps in four convergent pathways were necessary to produce racemic Nebivolol. Thus, the process of making racemic Nebivolol based on such strategy is complicated and inefficient. This invention offers a solution by enabling selective preparation of the intermediates as depicted in Scheme 6a, wherein each of the intermediates is obtained as a racemic mixture without prior resolution of enantiomers which are formed during the process.

Further, this invention offers possibility of preparing of enantiomerically pure Nebivolol, e.g., after resolution of selected racemic compounds, e.g., compound II (Schemes 6b and 6c).

This invention also provides a method of preparation of racemic Nebivolol, in which the formation of undesired diastereomers (e.g., SRSS/RSRR) in the final steps is reduced to a minimum by facilitating the purification and increasing the efficiency. Surprisingly, inventors have discovered that effective preparation of Nebivolol can advantageously utilize differences in solubility of other diastereomeric Nebivolol compounds as their HCl salts. Specifically, inventors observed that the racemic Nebivolol meso form (as HCl salt) having the configuration RSRS has an increased solubility as compared to the solubility of Nebivolol hydrochloride, whereas the second meso form having the configuration RRSS has a comparable solubility to that of Nebivolol hydrochloride. Solubility of the HCL-salts in MeOH: Nebivolol equals 1.5%, RRSS-meso form equals 1.0%, and RSRS-meso form is above 15%. In a preferred embodiment of this invention, a selective preparation of racemic Nebivolol is provided which may contain only a selected diastereomer (e.g., RSRS-meso form) as a possible impurity, which can be easily removed by a simple recrystallization due to the higher solubility. Therefore, a difficult and low yielding purification of the final product is avoided by this synthetic strategy because the formation of poorly soluble Nebivolol diastereomers (SRRS/RSSR, RRSS, SRSS/RSRR and RRRR/SSSS) is prevented.

Another aspect of the present invention is to provide a diastereoselective synthesis of the intermediate VIIIa containing the preferred syn-configuration. This compound is a useful intermediate in the above described synthetic strategy for the selective preparation of racemic Nebivolol, since it can only form as a contaminant the diastereomer having the RSRS configuration which can be easily removed in the final steps (Scheme 6a, steps 8 and 9).

Yet another aspect of the present invention is to provide an efficient method for selective reduction of compound IXa wherein the formation of the undesired RSRS isomer is reduced to a minimum.

Inventors have discovered that the efficiency of the process is further increased by providing recycling methods for the re-use of undesired diastereomers, which may be produced during the syntheses of the intermediates.

The method of preparing racemic Nebivolol (as shown in Scheme 6a) will now be described in detail.

The starting material for the present process is compound II, a racemic acid, which can be prepared by different routes according to the methods disclosed in U.S. Pat. No. 5,171,865 (see also counterpart EP 0331078) and U.S. Pat. No. 4,985,574 (see also counterpart EP 0264586).

Step 1 involves preparation of (±)-5-[6-fluorochroman-2-carbonyl]-2,2-dimethyl[1,3]dioxane-4,6-dione (compound III) from compound II as shown in Scheme 7.

Initially, the racemic acid II is transformed in an activated acid derivative which is then reacted with Meldrum's acid in an organic solvent and in the presence of a base to give the corresponding acylated Meldrumate III as a novel compound and a useful intermediate in the synthesis of Nebivolol. The acylation of Meldrum's acid can be carried out in the manner similar to a conventional procedure, e.g., as disclosed in J. Org. Chem. 43(10), 1978, 2087.

Scheme 7

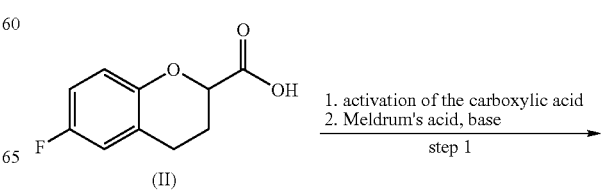

1. activation of the carboxylic acid
2. Meldrum's acid, base step 1

(II)

-continued

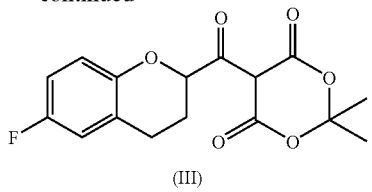

(III)

The carboxylic group can be activated in a conventional manner, e.g., as a carboxylic acide halide by using $PHal_5$, $PHal_3$, $SOHal_2$, $(COHal)_2$, as a carboxylic acid anhydride, as an activated ester, etc. Activation as an acid halide is preferred, and the chloride is the most preferred acid halide, which is prepared with 1 to 5 equivalents $SOCl_2$, preferably with 1-3 equivalents, in the presence of catalytical amounts of DMF. This reaction can be carried out without the use of any solvent or in a solvent such as, for example, benzene, alkyl or halogen substituted benzene, halogenated hydrocarbons, etc. Alkyl or halogen substituted benzene are preferred solvents and toluene is the most preferred solvent.

The reaction temperature can have a range from room temperature to the boiling point of the solvent. In a preferred embodiment, the reaction temperature ranges from 60° C. to 90° C. in toluene as the solvent. The acyl chloride can be obtained in almost quantitative yield by evaporation of the solvent together with the excess of chlorination reagent.

The acylation of Meldrum's acid can be done in the same solvent as used for the activation of the carboxylic acid. Halogenated hydrocarbons are the preferred solvents and methylene chloride is most preferred: Typically, the Meldrum's acid is used in molar proportions of 1 to 3 moles per mole of compound II, preferably in 1 to 1.5 moles per mole of compound II. The reaction is carried out in the presence of an organic or inorganic base, preferably in the presence of an organic base such as, for example, tertiary amine and most preferably in the presence of pyridine. In certain embodiments, 1 to 5 equivalents, preferably 1.5 to 3 equivalents of pyridine are used as the base. The reaction temperature may range between about −10° C. (but not below the melting point of the pure solvent, e.g., benzene) and about +30° C., preferably between 0° C. and room temperature. The reaction carried out in this temperature range (0° C.-RT) will be typically completed within 2 hours.

At the end of the reaction, the mixture is hydrolyzed and extracted with water or a diluted aqueous solution of an inorganic acid, preferably a 5% to 10% aqueous hydrochloride solution.

After separation of the layers, the organic solvent is evaporated and the residue may be used directly for the next step or purified by a recrystallization or by slurry in an organic solvent. Preferably, the residue is purified by slurry in an ether and most preferably in methyl tertiary-butyl ether (MTBE) or in diisopropyl ether.

If the preparation of enantiomerically pure Nebivolol is desired, it can be achieved by resolution of compound II using e.g. (+)-dehydroabietylamine as described in U.S. Pat. No. 6,545,040.

Step 2 involves preparation of compound IV, Scheme 6a, wherein R is H, yielding (±)-1-(6-fluoro-chroman-2-yl)-ethanone (compound IVa, Scheme 8, Route A), or COOR', wherein R' is alkyl or substituted alkyl, yielding (±)-3-(6-fluorochroman-2-yl)-3-oxo-propionic acid alkyl ester (compound IVb, Scheme 9, Route B).

Acylated Meldrum's acids are suitable intermediates for the preparation of the corresponding methyl ketone after hydrolysis and decarboxylation, or for the preparation of the corresponding beta-keto acids after alcoholysis and decarboxylation. The reactions may be carried out in the manner similar to a conventional procedure, e.g. as disclosed in J. Org. Chem. 43(10), 1978, 2087 and Synth. Commun., 10, 1980, 221.

Route A:

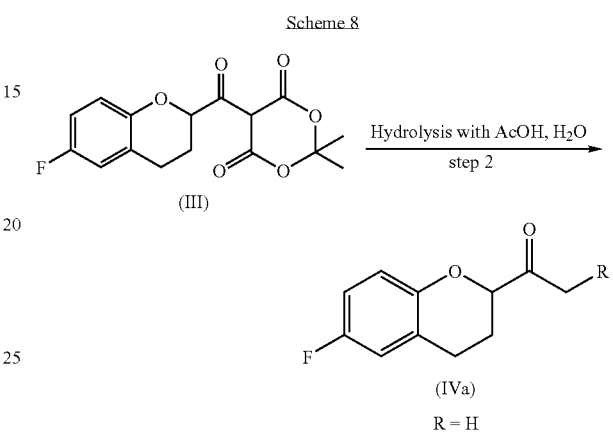

Scheme 8

(III)

Hydrolysis with AcOH, $H_2O$
step 2

(IVa)

R = H

The hydrolysis and decarboxylation of compound III to yield compound IVa (Scheme 8) as a novel compound and useful intermediate for the synthesis of Nebivolol can be carried out in an aqueous acid solution at reflux temperature. A mineral acid or an organic acid may be used, wherein acetic acid is preferred. Water may be used in excess; equal volume amounts of water and acetic acid are preferred. The compound can be used directly as a crude product or may be further purified by column chromatography.

Route B:

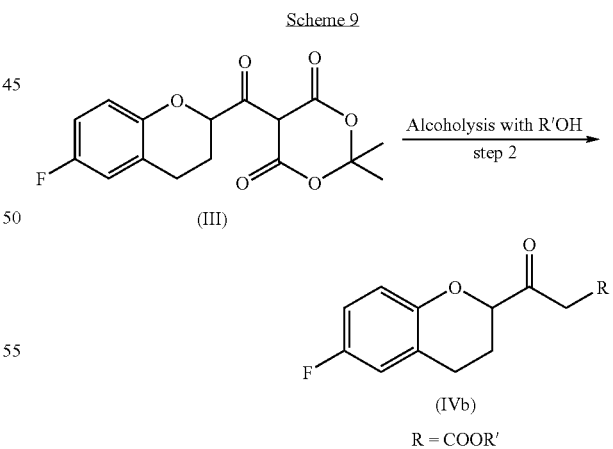

Scheme 9

(III)

Alcoholysis with R'OH
step 2

(IVb)

R = COOR'

Reaction of compound III with alcohols gives the corresponding beta-keto ester IVb as a novel compound and useful intermediate for the synthesis of Nebivolol, wherein R' is alkyl or substituted alkyl. This alcoholysis can be carried out with primary, secondary or tertiary alcohols, preferably with primary and tertiary alcohols and most preferably with ethanol or tert-butanol. As a solvent, the alcohol itself or an inert aromatic solvent can be used. Ethanol is the preferred solvent for the synthesis of the corresponding ethyl ester and toluene is the preferred solvent for the synthesis of the tert-butyl ester. The reaction temperature may have a range from reflux temperature for low boiling alcohols up to reflux temperature for toluene or the reflux temperature of the corresponding toluene/alcohol azeotrope. Preferred temperatures for the preparation of beta-keto ethyl ester as well as for the beta-keto tert-butyl ester are in a range from about 70 to about 80° C. After completion of the reaction, the reaction mixture may be worked up in a usual manner, e.g., by an extractive method, and the crude product may be used directly for the next step or purified by column chromatography.

Step 3 involves preparation of compound V from compound IV, e.g., (±)-2-bromo-1-(6-fluoro-chroman-2-yl)-ethanone (compound Va) and (±)-2-chloro-1-(6-fluoro-chroman-2-yl)-ethanone (compound Vb) (Schemes 10 and 11a-c).

The compound IV prepared according to step 2 can be used for the synthesis of compound V having a suitable leaving group (LG). Non-limiting examples of suitable leaving groups include substituted and non substituted alkyl and aryl sulfonic acid derivatives and halogen atoms. In a preferred embodiment, leaving groups are halogen atoms and the most preferred leaving groups are bromine (compound Va) and chlorine (compound Vb).

Compounds Va and Vb can be prepared via route A of Scheme 10 or route B of Schemes 11a-c as described below.

Route A:

The synthesis of the bromoketone (compound Va) by direct bromination of the methyl ketone (compound IVa) using bromine or NBS leads in most cases to a competitive bromination of the aromatic ring. However, after the previous conversion of the methyl ketone IVa to the corresponding silyl enol ether having the terminal double bond, the selective preparation of compound Va is possible (see Scheme 10).

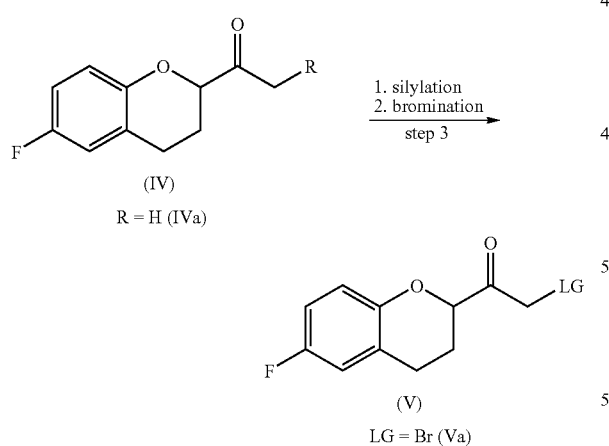

In a general procedure, the silyl enol ether can be obtained by kinetically controlled deprotonation using a strong base followed by silylation. Examples of a solvent include ethers or mixtures of ethers with such solvents, in which solutions of the strong bases are commonly available. The preferred preparation of the silyl enol ether uses lithium diisopropylamide (LDA) as the base, trimethylsilyl chloride (TMSCl) as a silylating reagent and tetrahydrofuran (THF) as the ether. The reaction starts at −78° C. with the addition of the compound IVa to a mixture of 1 to 1.5 equivalents LDA and 1 to 2 equivalents of TMSCl. Preferred are 1.2 equivalents of LDA and 1.6 equivalents of TMSCl. After the reaction is allowed to warm to room temperature, the mixture is first worked up by an extractive method and then concentrated. The bromination may be carried out in a suitable solvent with N-bromosuccinimide (NBS), 1,3-dibromo-5,5-dimethylhydantoin, or pyridine hydrobromide perbromide at 0° C. to room temperature. Suitable solvents include, for example, halogenated hydrocarbons, preferably, methylene chloride. After completion of the reaction, the mixture is worked up by an extractive method, and the product may be purified by column chromatography or by recrystallization. Since byproduct formation by nonselective bromination was observed, resulting in difficult purification, a more selective and efficient preparation of compound V was developed (see route B, Scheme 11a).

Route B:

Route B is an alternative preparation of the halogenated compounds Va and Vb, which gives a better selectivity than that of route A (see Scheme 11a).

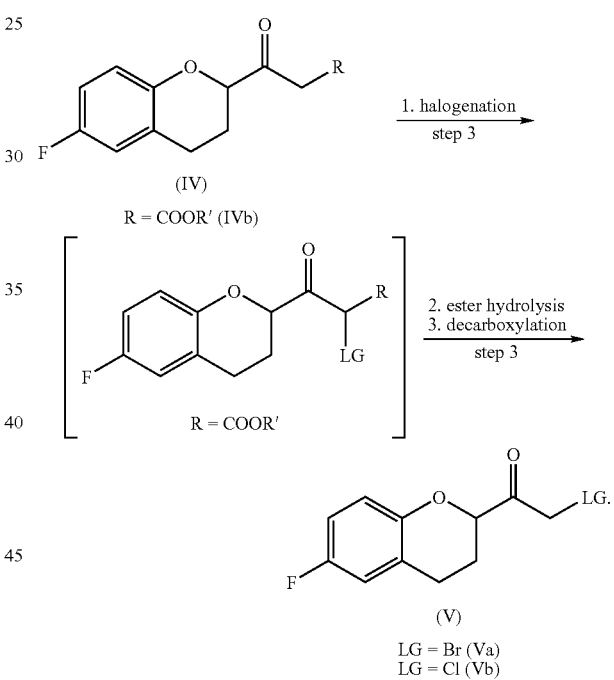

Advantageously, in route B, the reaction can be carried out at higher, more convenient temperatures by successive halogenation of the beta-keto ester IVb, followed by hydrolysis and decarboxylation. The halogenation can be done with a suitable halogenation reagent with or without a catalyst. Typical halogenation reagents for the preparation of the corresponding bromides or chlorides include, for example, NBS, NCS, and $SO_2Cl_2$. A non-limiting example of a catalyst includes $Mg(ClO_4)_2$. Suitable solvents for this reaction include acetonitrile, esters or halogenated hydrocarbons; acetonitrile, ethyl acetate and methylene chloride are preferred. In certain embodiments, 1.0 to 1.5 equivalents of the halogenation reagent and 0.3 equivalents of the catalyst can be used. The reaction proceeds between 0° C. and room temperature to a complete conversion within 3-4 hours. Higher temperatures for the halogenation should be avoided because of possible side reactions, and lower temperature may prolong the reaction time. The following ester hydrolysis and decarboxylation to form compound V can be done in an aqueous or non-aqueous acid solution at higher temperatures. Mineral acids or organic acids may be used.

Compound IVb as the ethyl or tert-butyl ester may be used as the starting material, with the tert-butyl ester being preferred. In the case of the use of the ethyl ester, the hydrolysis and decarboxylation of the corresponding halogenated beta keto ethyl ester may be preferably carried out with an aqueous trifluoro acetic acid solution. When the tert-butyl ester form is used, the hydrolysis and decarboxylation of the corresponding halogenated beta keto tert-butyl ester is carried out preferably in a mixture of formic acid and acetic acid and preferably in the presence of water. The reaction temperature for the ester hydrolysis and decarboxylation is in a range from about 60° C. to about 100° C., preferably 75-90° C. The purification of compound V may be done by as aforementioned for compound Va. Since compound Vb shows greater storage stability than compound Va, compound Vb is preferred.

Compound V having substituted or non substituted alkyl and aryl sulfonic acid derivatives as leaving groups may be prepared, e.g., by transformation of the compound IVb' or IVb" (LG=halogen) with salts of carboxylic acids to compound IVb''' followed first by ester hydrolysis then decarboxylation and sulfonylation using the corresponding alkyl or aryl sulfonic acid chlorides (see Scheme 11b). Alernatively, compound Vc may be prepared by similar transformation starting directly with the haloketones Va or Vb (see Scheme 11c)

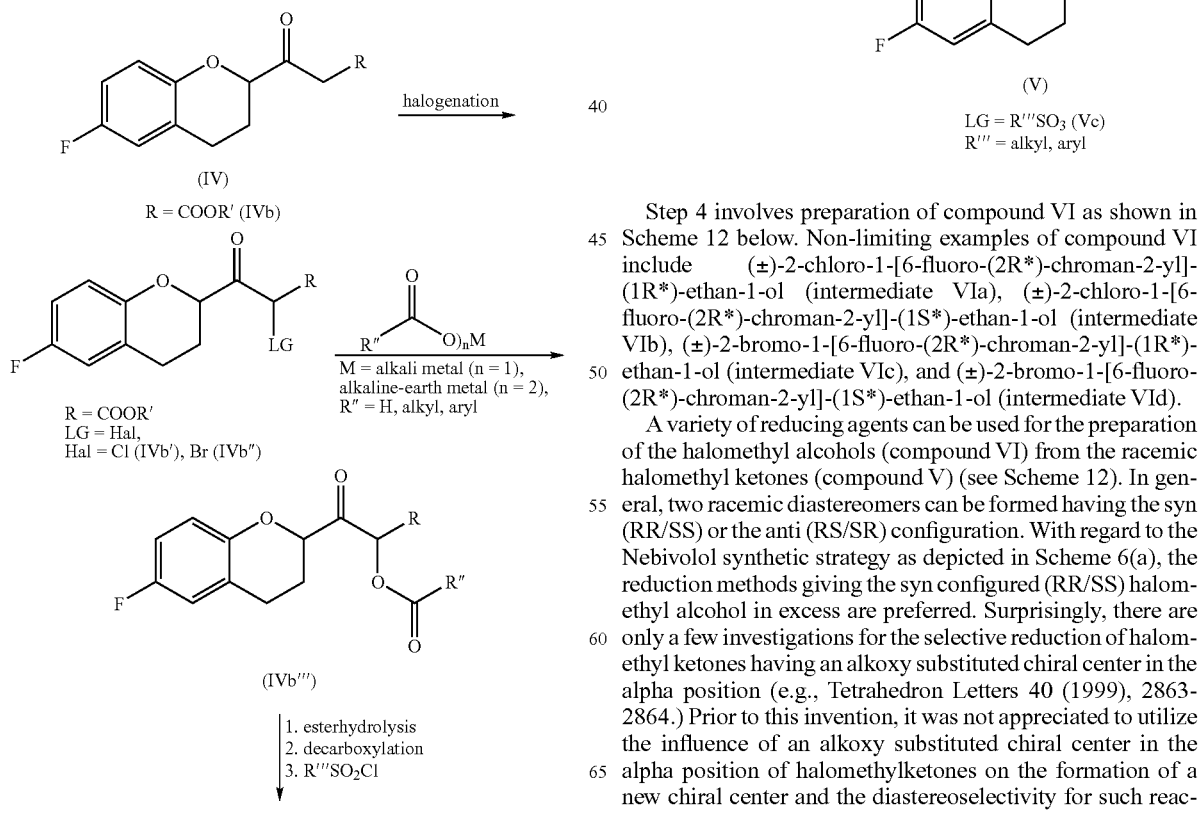

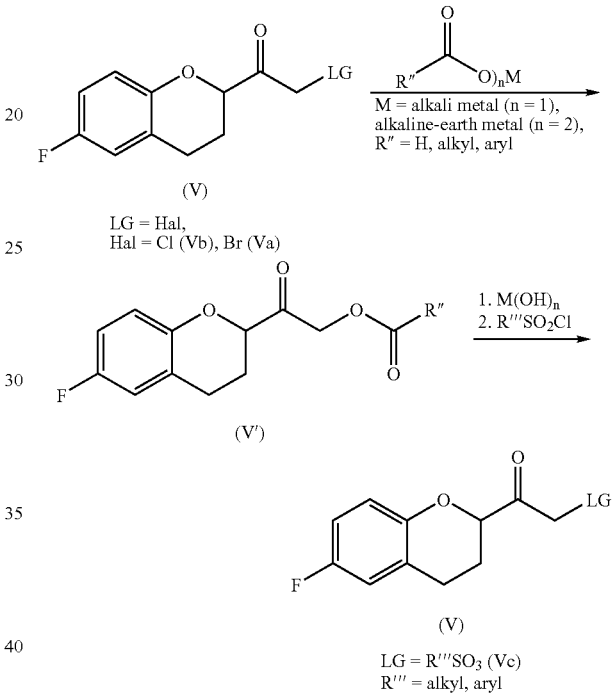

Step 4 involves preparation of compound VI as shown in Scheme 12 below. Non-limiting examples of compound VI include (±)-2-chloro-1-[6-fluoro-(2R*)-chroman-2-yl]-(1R*)-ethan-1-ol (intermediate VIa), (±)-2-chloro-1-[6-fluoro-(2R*)-chroman-2-yl]-(1S*)-ethan-1-ol (intermediate VIb), (±)-2-bromo-1-[6-fluoro-(2R*)-chroman-2-yl]-(1R*)-ethan-1-ol (intermediate VIc), and (±)-2-bromo-1-[6-fluoro-(2R*)-chroman-2-yl]-(1S*)-ethan-1-ol (intermediate VId).

A variety of reducing agents can be used for the preparation of the halomethyl alcohols (compound VI) from the racemic halomethyl ketones (compound V) (see Scheme 12). In general, two racemic diastereomers can be formed having the syn (RR/SS) or the anti (RS/SR) configuration. With regard to the Nebivolol synthetic strategy as depicted in Scheme 6(a), the reduction methods giving the syn configured (RR/SS) halomethyl alcohol in excess are preferred. Surprisingly, there are only a few investigations for the selective reduction of halomethyl ketones having an alkoxy substituted chiral center in the alpha position (e.g., Tetrahedron Letters 40 (1999), 2863-2864.) Prior to this invention, it was not appreciated to utilize the influence of an alkoxy substituted chiral center in the alpha position of halomethylketones on the formation of a new chiral center and the diastereoselectivity for such reactions is not well established).

Scheme 12:

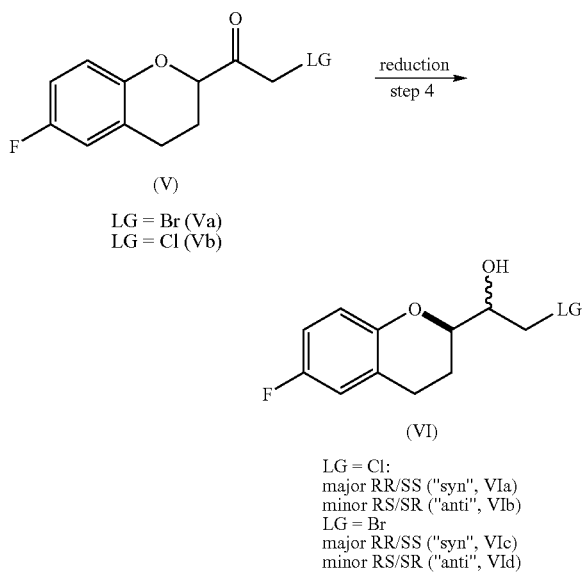

LG = Br (Va)
LG = Cl (Vb)

LG = Cl:
major RR/SS ("syn", VIa)
minor RS/SR ("anti", VIb)
LG = Br
major RR/SS ("syn", VIc)
minor RS/SR ("anti", VId)

In general, there is no limitation on the use of reduction agents, e.g., borohydride or aluminiumhydride reduction reagents as well as the reagents that are useful for Meerwein Pondorf Verley reductions. Non-limiting examples of reduction agents include $LiBH_4$, $NaBH_4$, $KBH_4$ $N(nBu)_4BH_4$, $Zn(BH_4)_2$, $NaH(Oac)_3$, Superhydride®, Red-Al, Li-Selectride, $BH_3xSMe_2$ or the like. In case of catalytic hydrogenation, suitable catalysts are catalysts that do not give side reactions with halogenated compounds (e.g., the catalyst as disclosed and cited in WO 03/064357). The reduction maybe carried out in the absence or in the presence of a Lewis acid, such as, for example, $MgCl_2$, $CaCl_2$, $BaCl_2$, $ZnCl_2$ $Al(Oalkyl)_3$, $Ti(Oalkyl)_4$ $BF_3xOEt_2$ and the like. Suitable solvents include ethers, alcohols, halogenated hydrocarbons, halogenated or alkylated aromatic solvents and the like, with the exception, that halogenated solvents are unsuited for catalytic reductions. Preferred halomethyl ketones of compound V bear chlorine or bromine as the substituent "LG". The reduction is conveniently carried out at temperatures between about −78° C. and about room temperature, preferably between −20° C. and room temperature. Table 2 shows representative results for the reduction of chloromethyl ketone Vb (LG=Cl).

TABLE 2

| Reagent (eq.) | Catalyst (eq.) | Solvent | Temperature [° C.] | Time [h] | Ratio RR/SS//RS/SR |
|---|---|---|---|---|---|
| $LiBH_4$ (1) | none | THF | −20 to −15 | 1 | 58.3//41.7 |
| $LiBH_4$ (1) | none | MeOH | −20 to −15 | 1 | 60.2//39.8 |
| $LiBH_4$ (1) | none | iPrOH | −20 to −15 | 1 | 51.0//49.0 |
| $LiBH_4$ (1) | none | $CH_2Cl_2$ | −20 to −15 | 3 | 42.8//57.2 |
| $LiBH_4$ (1) | none | toluene | −20 to RT | overnight | 41.5//58.5 |
| $LiBH_4$ (1) | none | DME | −20 to −15 | 1 | 53.8//46.2 |
| $LiBH_4$ (1) | $ZnCl_2$ (2) | THF | −20 to −15 | 1 | 56.9//43.1 |
| $LiBH_4$ (1) | $ZnCl_2$ (2) | MeOH | −20 to −15 | 1 | 63.7//36.3 |
| $LiBH_4$ (1) | $ZnCl_2$ (2) | iPrOH | −20 to −15 | 1 | 60.3//39.7 |
| $LiBH_4$ (1) | $ZnCl_2$ (2) | $CH_2Cl_2$ | −20 to RT | overnight | 59.3//40.7 |
| $LiBH_4$ (1) | $ZnCl_2$ (2) | toluene | −20 to RT | overnight | 53.0//47.0 |
| $LiBH_4$ (1) | $ZnCl_2$ (2) | DME | −20 to −15 | 2 | 46.7//53.3 |
| $LiBH_4$ (1) | $Ti(OiPr)_4$ (2) | THF | −20 to −15 | 1 | 48.8//51.2 |
| $LiBH_4$ (1) | $Ti(OiPr)_4$ (2) | MeOH | −20 to −15 | 1 | 59.3//40.7 |
| $LiBH_4$ (1) | $Ti(OiPr)_4$ (2) | iPrOH | −20 to −15 | 1 | 47.3//52.7 |
| $LiBH_4$ (1) | $Ti(OiPr)_4$ (2) | $CH_2Cl_2$ | −20 to −15 | 1 | 35.6//64.4 |
| $LiBH_4$ (1) | $Ti(OiPr)_4$ (2) | Toluene | −20 to −15 | 1 | 38.1//61.9 |
| $LiBH_4$ (1) | $Ti(OiPr)_4$ (2) | DME | −20 to −15 | 1 | 43.4//56.6 |
| $LiBH_4$ (1) | $MgCl_2$ (2) | THF | −20 to −15 | 3 | 57.8//42.2 |
| $LiBH_4$ (1) | $MgCl_2$ (2) | MeOH | −20 to −15 | 1.5 | 59.5//40.5 |
| $LiBH_4$ (1) | $MgCl_2$ (2) | iPrOH | −20 to −15 | 1.5 | 41.1//58.9 |
| $LiBH_4$ (1) | $MgCl_2$ (2) | $CH_2Cl_2$ | −20 to −15 | 2.5 | 44.3//55.7 |
| $LiBH_4$ (1) | $MgCl_2$ (2) | Toluene | −20 to −15 | 2.5 | 42.9//57.1 |
| $LiBH_4$ (1) | $MgCl_2$ (2) | DME | −20 to −15 | 1 | 52.4//47.6 |
| $LiBH_4$ (1) | $Al(OiPr)_3$ (2) | THF | −20 to −15 | 1 | 54.7//45.3 |
| $LiBH_4$ (1) | $Al(OiPr)_3$ (2) | MeOH | −20 to −15 | 1 | 59.7//40.3 |
| $LiBH_4$ (1) | $Al(OiPr)_3$ (2) | iPrOH | −20 to −15 | 1 | 50.5//49.5 |
| $LiBH_4$ (1) | $Al(OiPr)_3$ (2) | $CH_2Cl_2$ | −20 to −15 | 1 | 41.9//58.1 |
| $LiBH_4$ (1) | $Al(OiPr)_3$ (2) | Toluene | −20 to −15 | 1 | 39.6//60.4 |
| $LiBH_4$ (1) | $Al(OiPr)_3$ (2) | DME | −20 to −15 | 1 | 51.1//48.9 |
| $LiBH_4$ (1) | $BF_3xOEt_2$ (2) | THF | −20 to RT | overnight | 61.5//38.5* |
| $LiBH_4$ (1) | $BF_3xOEt_2$ (2) | MeOH | −20 to RT | overnight | 56.3//43.7* |
| $LiBH_4$ (1) | $BF_3xOEt_2$ (2) | iPrOH | −20 to RT | overnight | 55.4//44.6* |
| $LiBH_4$ (1) | $BF_3xOEt_2$ (2) | $CH_2Cl_2$ | −20 to −15 | 3 | 44.9//55.1 |
| $LiBH_4$ (1) | $BF_3xOEt_2$ (2) | Toluene | −20 to RT | overnight | 45.6//54.6* |
| $LiBH_4$ (1) | $BF_3xOEt_2$ (2) | DME | −20 to −15 | 1 | 46.0//54.0 |
| $NaBH_4$ (1) | none | THF | −20 to −15 | 1 | 51.8//48.2 |
| $NaBH_4$ (1) | none | MeOH | −20 to −15 | 1 | 60.2//39.8 |
| $NaBH_4$ (1) | none | iPrOH | −20 to RT | 22.25 | 59.1//40.9 |
| $NaBH_4$ (1) | none | $CH_2Cl_2$ | −20 to RT | 21 | 50.9//49.1* |
| $NaBH_4$ (1) | none | Toluene | −20 to RT | 21 | 51.7//48.3* |
| $NaBH_4$ (1) | none | DME | −20 to −15 | 1 | 54.7//45.3 |
| $NaBH_4$ (1) | none | EtOH | −78° C. to RT | 3 | 56.8//43.2 |

TABLE 2-continued

| Reagent (eq.) | Catalyst (eq.) | Solvent | Temperature [° C.] | Time [h] | Ratio RR/SS//RS/SR |
|---|---|---|---|---|---|
| NaBH$_4$ (0.5) | none | iPrOH | RT | 0.5 | 50.4//49.6 |
| NaBH$_4$ (1) | ZnCl$_2$ (2) | THF | −20 to −15 | 1 | 58.3//41.7 |
| NaBH$_4$ (1) | ZnCl$_2$ (2) | MeOH | −20 to −15 | 1 | 63.4//36.6 |
| NaBH$_4$ (1) | ZnCl$_2$ (2) | iPrOH | −20 to RT | 18 | 59.7//40.3 |
| NaBH$_4$ (1) | ZnCl$_2$ (2) | CH$_2$Cl$_2$ | −20 to RT | 21 | 63.8//36.2* |
| NaBH$_4$ (1) | ZnCl$_2$ (2) | Toluene | −20 to RT | 21 | 61.5//38.5* |
| NaBH$_4$ (1) | ZnCl$_2$ (2) | DME | −20 to −15 | 2 | 49.3//50.7 |
| NaBH$_4$ (1) | Ti(OiPr)$_4$ (2) | THF | −20 to −15 | 1 | 42.8//57.2 |
| NaBH$_4$ (1) | Ti(OiPr)$_4$ (2) | MeOH | −20 to −15 | 1 | 58.8//41.2 |
| NaBH$_4$ (1) | Ti(OiPr)$_4$ (2) | iPrOH | −20 to −15 | 3 | 46.4//63.6 |
| NaBH$_4$ (1) | Ti(OiPr)$_4$ (2) | CH$_2$Cl$_2$ | −20 to RT | 18 | 38.4//61.6 |
| NaBH$_4$ (1) | Ti(OiPr)$_4$ (2) | Toluene | −20 to RT | 18 | 41.4//58.6 |
| NaBH$_4$ (1) | Ti(OiPr)$_4$ (2) | DME | −20 to −15 | 1 | 44.9//55.7 |
| NaBH$_4$ (1) | MgCl$_2$ (2) | THF | −20 to RT | 18 | 44.4//55.6* |
| NaBH$_4$ (1) | MgCl$_2$ (2) | MeOH | −20 to −15 | 2 | 58.1//41.99 |
| NaBH$_4$ (1) | MgCl$_2$ (2) | iPrOH | −20 to −15 | 2 | 53.4//46.6 |
| NaBH$_4$ (1) | MgCl$_2$ (2) | CH$_2$Cl$_2$ | −20 to RT | 18 | 58.2//41.8* |
| NaBH$_4$ (1) | MgCl$_2$ (2) | Toluene | −20 to RT | 18 | 47.9//52.1 |
| NaBH$_4$ (1) | MgCl$_2$ (2) | DME | −20 to −15 | 1 | 47.8//52.2 |
| NaBH$_4$ (1) | Al(OiPr)$_3$ (2) | THF | −20 to RT | | 46.5//53.5 |
| NaBH$_4$ (1) | Al(OiPr)$_3$ (2) | MeOH | −20 to −15 | 1 | 59.6//40.4 |
| NaBH$_4$ (1) | Al(OiPr)$_3$ (2) | iPrOH | −20 to −15 | 3 | 48.6//51.4 |
| NaBH$_4$ (1) | Al(OiPr)$_3$ (2) | CH$_2$Cl$_2$ | −20 to −15 | 3 | 55.0//45.0* |
| NaBH$_4$ (1) | Al(OiPr)$_3$ (2) | Toluene | −20 to −15 | 3 | 52.0//48.0* |
| NaBH$_4$ (1) | Al(OiPr)$_3$ (2) | DME | −20 to −15 | 1 | 50.4//49.6 |
| NaBH$_4$ (1) | BF$_3$xOEt$_2$ (2) | THF | −20 to RT | 20 | 52.3//47.7* |
| NaBH$_4$ (1) | BF$_3$xOEt$_2$ (2) | MeOH | −20 to RT | 20 | 57.0//43.0* |
| NaBH$_4$ (1) | BF$_3$xOEt$_2$ (2) | iPrOH | −20 to RT | 20 | 53.4//46.6* |
| NaBH$_4$ (1) | BF$_3$xOEt$_2$ (2) | CH$_2$Cl$_2$ | −20 to RT | 20 | 60.0//40.0* |
| NaBH$_4$ (1) | BF$_3$xOEt$_2$ (2) | Toluene | −20 to RT | 20 | 61.5//38.5* |
| NaBH$_4$ (1) | BF$_3$xOEt$_2$ (2) | DME | −20 to −15 | 1 | 41.7//58.3 |
| NaBH$_4$ (1) | MgCl$_2$ (2) | MeOH | 0 to 5 | 0.5 | 54.0//46.0 |
| NaBH$_4$ (1) | MgCl$_2$ (2) | MeOH | −78 to RT | 0.5 | 65.9//34.1 |
| NaBH$_4$ (1) | MgCl$_2$ (2) | THF | 0 to RT | 22 | 41.0//59.0 |
| NaBH$_4$ (1) | CaCl$_2$ (2) | MeOH | 0 to 5 | 0.5 | 47.0//53.0 |
| NaBH$_4$ (1) | BaCl$_2$ (2) | MeOH | 0 to 5 | 0.5 | 50.0//50.0 |
| NaBH$_4$ (11.1) | CeCl$_3$ (2) | MeOH | 0 to 5 | 2 | 36.9//63.1 |
| NaBH$_4$ (1) | ZnCl$_2$ (2) | MeOH | 0 to 5 | 0.5 | 61.0//39.0 |
| NaBH$_4$ (1) | ZnCl$_2$ (2) | MeOH | −78 to RT | 2 | 64.7//35.5 |
| NaBH$_4$ (1) | ZnCl$_2$ (2) | THF | −10 | 0.25 | 57.0//43.0 |
| NaBH$_4$ (1) | ZnCl$_2$ (2) | Et$_2$O | −10 | 0.25 | 56.0//44.0 |
| NaBH$_4$ (1) | ZnCl$_2$ (2) | DME | −10 | 0.25 | 50.0//50.0 |
| NaBH$_4$ (1) | ZnCl$_2$ (2) | EtOH | −20 to −15 | 1 | 64.0//36.0 |
| NaBH$_4$ (1) | ZnCl$_2$ (1.5) | EtOH | −20 to −15 | 1.5 | 64.2//35.8 |
| NaBH$_4$ (1) | ZnCl$_2$ (1.0) | EtOH | −20 to −15 | 1.5 | 64.7//35.3 |
| NaBH$_4$ (1) | ZnCl$_2$ (0.5) | EtOH | −20 to −15 | 1.5 | 64.9//35.1 |
| NaBH$_4$ (1) | ZnCl$_2$ (0.3) | EtOH | −20 to −15 | 1.5 | 63.8//36.2 |
| NaBH$_4$ (1) | ZnCl$_2$ (0.2) | EtOH | −20 to −15 | 1.5 | 63.2//36.8 |
| NaBH$_4$ (1) | ZnCl$_2$ (0.1) | EtOH | −20 to −15 | 1.5 | 63.0//37.0 |
| NaBH$_4$ (1) | none | EtOH | −20 to −15 | 1.0 | 54.7//45.3 |
| Bu$_4$NH$_4$ (1) | ZnCl$_2$ (2) | MeOH | −20 to −15 | 1 | 63.9//36.1 |
| Bu$_4$NH$_4$ (1) | Al(OiPr)$_3$ (2) | MeOH | −20 to −15 | 1 | 60.5//39.5 |
| Bu$_4$NH$_4$ (1) | ZnCl$_2$ (2) | EtOH | −20 to −15 | 1 | 62.7//37.3 |
| Zn(BH$_4$)$_2$ (1.0) | none | Et$_2$O | −78 to RT | 3 | 64.9//34.1 |
| Zn(BH$_4$)$_2$ (1.4) | none | Et$_2$O | −78 | 0.5 | 59.1//40.9 |
| Zn(BH$_4$)$_2$ (1.4) | none | THF/Et$_2$O (1/1) | −78 | 0.5 | 59.4//40.6 |
| Zn(BH$_4$)$_2$ (1.4) | none | THF/Et$_2$O (1/2) | −78 | 0.5 | 58.4//41.6 |
| Zn(BH$_4$)$_2$ (1.4) | none | THF/Et$_2$O (2/1) | −78 | 0.5 | 62.2//37.8 |
| Bu$_4$NBH$_4$ (1.1) | none | THF | −78 | 2 | 59.8//40.2 |
| Bu$_4$NBH$_4$ (1.3) | none | CH$_2$Cl$_2$ | −78 | 2 | 39.2//60.8 |
| Bu$_4$NBH$_4$ (1.1) | none | THF/CH$_2$Cl$_2$ (1/1) | −78 | 2 | 66.7//33.3 |
| Bu$_4$NBH$_4$ (1.1) | none | THF/CH$_2$Cl$_2$ (1/1) | 0 | 2 | 52.2//47.8 |
| Bu$_4$NBH$_4$ (1.1) | ZnCl$_2$ (2) | THF/CH$_2$Cl$_2$ (1/1) | −78 | 2 | 60.7//39.3 |
| NaBH(Oac)$_3$ (2) | ZnCl$_2$ (2) | THF/Et$_2$O (2/1) | 0 to RT | 22 | 52.2//47.8* |
| BH$_3$xSMe$_2$ (1.1) | none | THF/CH$_2$Cl$_2$ (1/1) | −78 | 2 | 57.7//42.3 |
| BH$_3$xSMe$_2$ (1.1) | ZnCl$_2$ (2) | THF/CH$_2$Cl$_2$ (1/1) | −78 | 2 | 61.8//38.2 |
| Red-Al (1.3) | none | CH$_2$Cl$_2$/Toluene (1/1) | −78 | 3 | 52.9//48.0 |
| Red-Al (1.3) | ZnCl$_2$ (2) | CH$_2$Cl$_2$/Toluene (1/1) | −78 | 3 | 54.1//45.9* |
| Superhydride ® (1.1) | none | THF/CH$_2$Cl$_2$ (1/1) | −78 | 2 | 35.5//64.4 |
| Superhydride ® (1.1) | ZnCl$_2$ (2) | THF/CH$_2$Cl$_2$ (1/1) | −78 | 2 | 37.4//62.6 |
| DIBAH (1.1) | none | THF/CH$_2$Cl$_2$ (1/1) | −78 | 2 | 60.1//39.9* |
| Li(tBuO)$_3$AlH | none | THF/CH$_2$Cl$_2$ (1/1) | −78 | 2 | 44.4//55.6 |
| Li(tBuO)$_3$AlH | ZnCl$_2$ (2) | THF/CH$_2$Cl$_2$ (1/1) | −78 | 2 | 56.6//43.4 |
| Al(OiPr)$_3$ (0.5) iPrOH (7.0) | CH$_3$SO$_3$H (0.5) | Toluene | 35–45 | 1.5 | 27.9//72.1 |

TABLE 2-continued

| Reagent (eq.) | Catalyst (eq.) | Solvent | Temperature [° C.] | Time [h] | Ratio RR/SS//RS/SR |
|---|---|---|---|---|---|
| Al(OiPr)$_3$ (0.5) BINAPHTHOL iPrOH (5.0) | none | Toluene | 20-25 | 16 | 25.6//74.4 |
| DIBAH (2.0) Acetone (2.0) | none | THF | 20-25 | 16 | 27.6//72.4 |
| DIBAH (2.0) Acetone (2.0) | none | THF/Toluene (1/1) | 20-25 | 16 | 27.6//72.4 |
| Al(OtBu)$_3$ (0.5) D/L-Phenethyl-alkohol (2.0) | none | Toluene | 20-25 | 2 | 28.0//72.0 |
| Al(OtBu)$_3$ (0.1) D/L-Phenethyl-alkohol (2.0) | none | Toluene | 20-25 | 6 | 28.0//72.0 |
| Al(OsBu)$_3$ (0.5) sBuOH (7.0) | CH$_3$SO$_3$H (0.5) | Toluene | 20-25 | 1 | 25.7//74.3 |
| Al(OiPr)$_3$ (0.5) Cyclohexanol (7.0) | CH$_3$SO$_3$H (0.5) | Toluene | 20-25 | 5 | 19.6//80.4 |
| Al(OtBu)$_3$ (0.5) Cyclohexanol (7.0) | CH$_3$SO$_3$H (0.5) | Toluene | 20-25 | 3 | 18.4//81.6 |
| Al(OtBu)$_3$ (0.5) Cyclohexanol (7.0) | CH$_3$SO$_3$H (0.5) | Toluene | 0-5 | 6 | 14.5//85.5 |
| Al(OtBu)$_3$ (0.5) 3-Pentanol (7.0) | CH$_3$SO$_3$H (0.5) | Toluene | 0-5 | 3 | 18.0//82.0 |
| Al(OtBu)$_3$ (0.5) 9-Hydroxyfluoren (3.4) | CH$_3$SO$_3$H (0.5) | Toluene | 0-5 | 4.5 | 27.1//72.9 |
| Al(OtBu)$_3$ (0.5) Diphenylcarbinol (7.0) | CH$_3$SO$_3$H (0.5) | Toluene | 0-RT | 31 | 11.7//88.3 |

In Table 2, incomplete conversion is marked with the symbol "*".

The ratio of diastereomeric configurations RR/SS to RS/SR is from about 0.3 to about 2, preferably 1.1 to 2, and most preferably 1.2 to 2.

It was observed that diastereoselective reductions at temperatures above −20° C. give the best ratio for the diastereomer (compound VIa, syn configuration RR/SS) when the reaction is carried out e.g. with NaBH$_4$ in MeOH or EtOH in the presence of a catalyst e.g., ZnCl2 (0.1-2.0 equivalents). Formation of the diastereomer having the anti configuration (compound VIb, RS/SR) is favored by using the Meerwein Pondorf Verley reduction. In this case, the ratio of RS/SR to RR/SS is up to 9.

After the almost complete conversion, the reaction can be worked up in a manner known in the art, by concentrating the reaction mixture and dissolving the residue in a water immiscible solvent, preferably toluene or MTBE, followed by successive washing with an aqueous acid solution, preferably 2N HCl solution followed by washing with water and/or an alkaline solution, preferably NaHCO$_3$ solution. The diastereomeric product mixture may be purified by column chromatography or used directly for the next step.

It was observed that in contrast to the reduction of compound Vb, the reduction of compound Va proceeds with partial cyclization to the corresponding epoxides (compounds VIIa and VIIb, see below).

Step 5 involves preparation of compound VII from compound VI as shown in Scheme 13. Non-limiting examples of compound VH include (±)-6-fluoro-[(2R*)-oxiran-2-yl]-(2S*)-chromane (compound VIIa) and (±)-6-fluoro-[(2R*)-oxiran-2-yl]-(2R*)-chromane (compound VIIb).

Scheme 13:

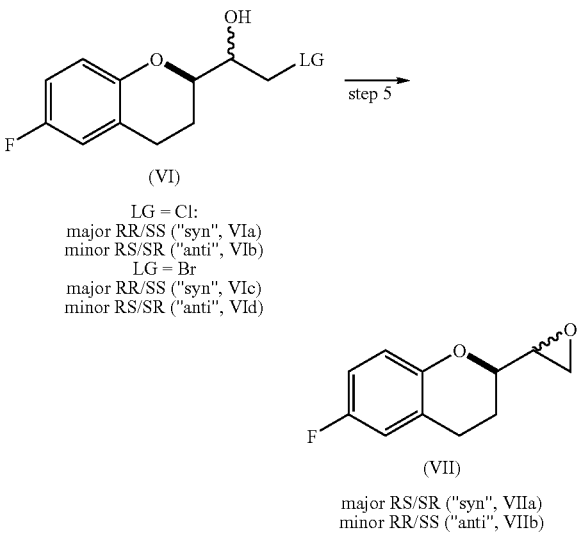

(VI)

LG = Cl:
major RR/SS ("syn", VIa)
minor RS/SR ("anti", VIb)
LG = Br
major RR/SS ("syn", VIc)
minor RS/SR ("anti", VId)

(VII)

major RS/SR ("syn", VIIa)
minor RR/SS ("anti", VIIb)

Formation of the epoxides of compound VII from the halomethyl alcohols of compound VI is conveniently carried out in solvents such as, for example, ethers or alcohols with a base such as, for example, alkali or alkaline earth metal hydroxide, alkali or alkaline earth metal alkoxides, alkali or alkaline earth metal carbonates, tertiary amines or alkali hydrides. The use of alkali alkoxides in alcohols as the solvent is preferred, and most preferred is the use of sodium methoxide in methanol as the solvent. The temperature for this reaction may range between about 0° C. and about 40° C., preferably between 15° C. and 25° C. About 1.0 to about 2.0 equivalents of the base may be used and 1.1 equivalents are preferred. Upon completion of the reaction, the excess base is typically neutralized by addition of an acid, preferably acetic acid. The mixture is then concentrated, and the residue is dissolved in a suitable solvent, e.g., an ether or a halogenated hydrocarbon. Washing this solution off with a half saturated aqueous sodium chloride solution and concentration of the organic layer gives epoxides of compound VII. If the reaction is carried out using a mixture of diastereomeric halomethyl alcohols of formula VI, then the corresponding diastereomeric epoxide mixture of formula VII will be formed. The diastereomeric mixture of epoxides may be used directly for the next step or separated by column chromatography. In a preferred embodiment of the process, the mixture is used for the next step without separation of the diastereomers.

Step 6 involves preparation of compound VIII from compound VII as shown in Scheme 14 and separation of the diastereomers. Non-limiting examples of compound VIII include (±)-2-Benzylamino-1-[6-fluoro-(2R*)-chroman-2-yl]-(1S*)-ethan-1-ol (compound VIIIa) and (±)-2-Benzylamino-1-[6-fluoro-(2R*)-chroman-2-yl]-(1R*)-ethan-1-ol (compound VIIIb).

Scheme 14:

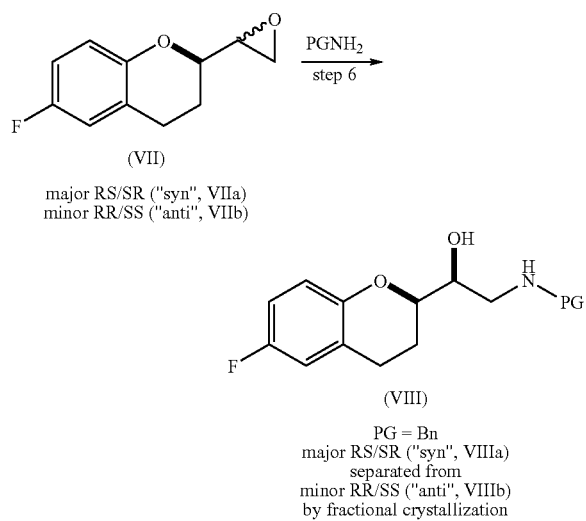

(VII)

major RS/SR ("syn", VIIa)
minor RR/SS ("anti", VIIb)

PG = Bn
major RS/SR ("syn", VIIIa)
separated from
minor RR/SS ("anti", VIIIb)
by fractional crystallization Examples of suitable protective groups (PG) include hydrogen or a suitable amine protecting group. Preferred are protecting groups which permit the subsequent alkylation step (step 7) and can be easily removed in the final step by a simple deprotection method. Therefore, preferred PG is an allyl group, a substituted or unsubstituted arylmethyl group. If PG is a benzyl group, then the preparation of compounds VIII may be carried out in the same manner as described in EP 0145067 but without any prior separation of the diastereomeric mixture of compounds VIIa and VIIb. Advantageously, inventors have discovered that a chromatographic separation of the oily compounds VIIa and VIIb is not necessary in this method, and that the diastereomeric mixture can be separated by fractional crystallization after conversion to VIIIa and VIIIb. Therefore, in a preferred embodiment of the procedure, a mixture of VIIa and VIIb is reacted with benzylamine to give the corresponding diastereomeric mixture of the compounds VIIIa and VIIIb, which is further separated by fractional crystallization. Since compounds VIIIa and VIIIb have basic properties, the fractional crystallization may be carried out not only with the free amine but also with an appropriate salt. Compound VIIIa as well as compound VIIIb are useful intermediates for the preparation of Nebivolol and therefore this method can be used for the selective preparation of both isomers in a commercial scale process.

With regard to the present strategy for the preparation of Nebivolol, the selective preparation and isolation of compound VIIIa is most preferred.

In a typical preparation, an equimolar or an enriched diastereomeric mixture of compounds VIIa (syn) and VIIb (anti) at ratio syn/anti of more or equal 1, produced according to steps 4 and 5, is treated with an excess benzylamine ($\geqq 3$ equivalents) in a $C_1$-$C_3$-alcohol as the solvent at temperatures ranging from about room temperature to about 50° C. In a preferred embodiment, the reaction is carried out at 40° C. with 3 equivalents of benzylamine in 2-propanol.

After complete conversion, the reaction mixture is cooled to initiate the crystallization. It was found that the preferred reaction solvent is suitable for the fractional crystallization. Additional crops may be obtained by further crystallization of the concentrated mother liquors from the same alcohol or mixture of this alcohol with ethers, preferably diisopropyl ether. Further enrichment of the diastereomeric ratio with regard to compound VIIIa can be obtained by recrystallization or by slurry in $C_1$-$C_3$-alcohols, ethers, toluene, acetonitrile or mixtures thereof.

Beginning with a diastereomeric mixture of compounds VIIa and VIIb at a ratio of about 57/43, the compound VIIIa could be obtained according to the aforementioned procedure containing 5% or less of compound VIIIb.

Figure 2:
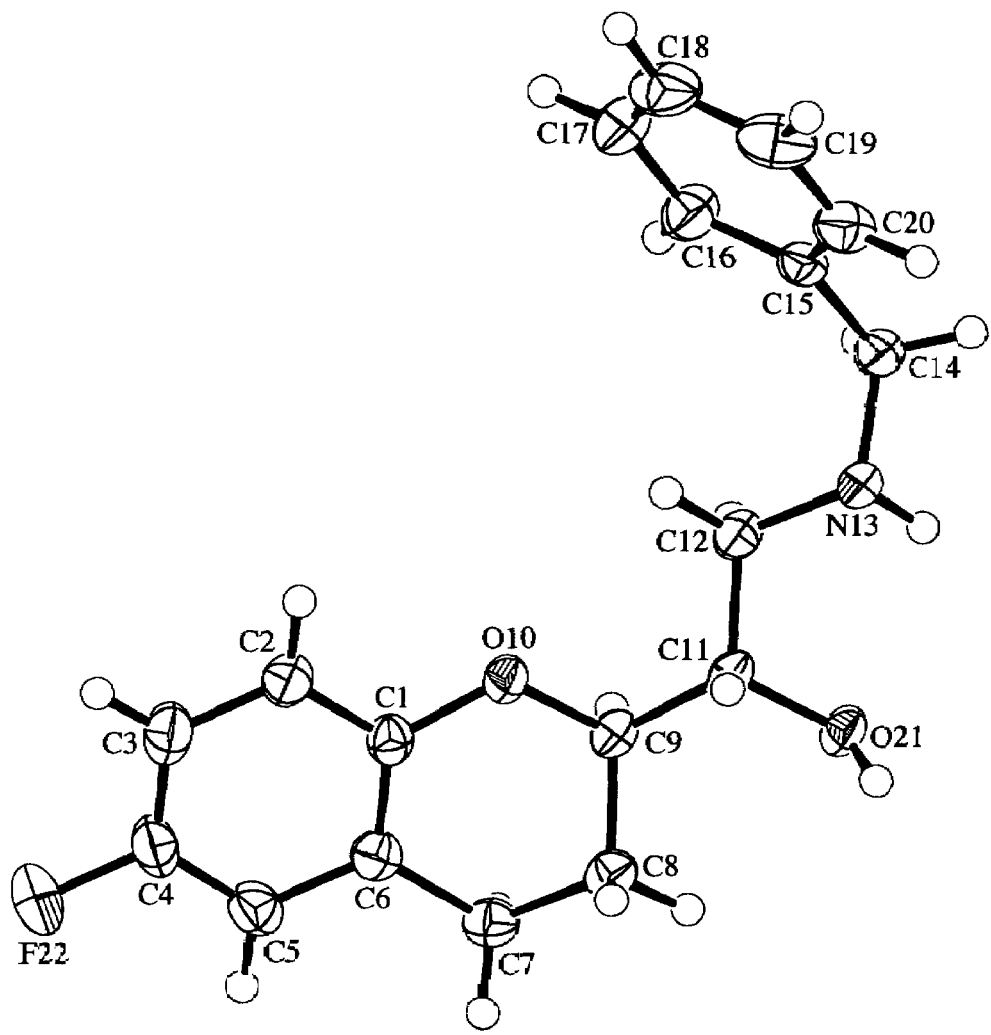
FIG. 2 is an atom-numbering schematic representation of the molecule of compound VIIIa (50% probability ellipsoids; H-atoms given arbitrary displacement parameters for clarity).

The relative configuration of the preferred compound VIIIa (see FIG. 2) was confirmed by single X-ray measurement as shown in Table 3 below.

TABLE 3

| Crystallographic data of compound VIIIa | |
|---|---|
| Crystallized from | diisopropyl ether/$CH_2Cl_2$ |
| Empirical formula | $C_{18}H_{20}FNO_2$ |
| Formula weight [g mol$^{-1}$] | 301.36 |
| Crystal colour, habit | colorless, prism |
| Crystal dimensions [mm] | 0.15 × 0.20 × 0.25 |
| Temperature [K] | 160(1) |
| Crystal system | monoclinic |
| Space group | $P2_1/c$ (#14) |
| Z | 4 |
| Reflections for cell determination | 4489 |
| 2θ range for cell determination [°] | 4-60 |
| Unit cell parameters a [Å] | 4.5882(1) |
| b [Å] | 26.3162(5) |
| c [Å] | 12.4357(3) |
| α [°] | 90 |
| β [°] | 92.288(1) |
| γ [°] | 90 |
| V [Å$^3$] | 1500.34(6) |
| F(000) | 640 |
| $D_x$ [g cm$^{-3}$] | 1.334 |
| μ(Mo Kα) [mm$^{-1}$] | 0.0947 |
| Scan type | φ and ω |
| $2\theta_{(max)}$ [°] | 60 |
| Total reflections measured | 35736 |
| Symmetry independent reflections | 4388 |
| $R_{int}$ | 0.061 |
| Reflections with I > 2σ(I) | 3005 |
| Reflections used in refinement | 4386 |
| Parameters refined | 208 |
| Final R(F) [I > 2σ(I) reflections] | 0.0480 |
| wR(F$^2$) (all data) | 0.1162 |
| Weights: | w = [σ$^2$(F$_o^2$) + (0.0419P)$^2$ + 0.2604P]$^{-1}$ where P = (F$_o^2$ + 2F$_c^2$)/3 |
| Goodness of fit | 1.036 |
| Secondary extinction coefficient | 0.012(2) |
| Final $\Delta_{max}/\sigma$ | 0.001 |
| Δρ (max; min) [e Å$^{-3}$] | 0.24; −0.19 |
| σ(d$_{(C-C)}$) [Å] | 0.002 |

Step 7 involves preparation of compound IX from compounds VIII and V and separation of diastereomers of compound IX. Non-limiting examples of compound IX include (±)-2-{Benzyl-[2-(6-fluoro-(2R*)-chroman-2-yl)-(2S*)-hydroxy-ethyl]-amino}-1-(6-fluoro-(2S*)-chroman-2-yl)-ethanone (compound IXa) (Scheme 15) and (±)-2-{Benzyl-[2-(6-fluoro-(2R*)-chroman-2-yl)-(2S*)-hydroxy-ethyl]-amino}-1-(6-fluoro-(2R*)-chroman-2-yl)-ethanone (compound IXb) (see Scheme 17).

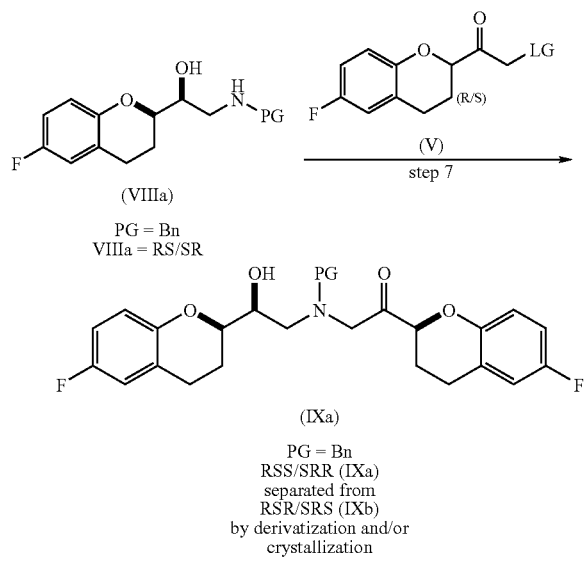

Reaction of the preferred racemic diastereomer of compound VIIIa with the racemic compound V, having an appropriate reactive leaving group (LG), gives a diastereomeric mixture of the new compounds IXa and IXb. This mixture may be separated by column chromatography or by fractional crystallization to obtain the desired compound IXa as a suitable intermediate for the synthesis of racemic Nebivolol. Since the compounds IXa and IXb have basic properties, the fractional crystallization may be carried out using the free amine or an appropriate salt.

As described in Step 3 above, suitable leaving groups (LG) of compound V include halogen, alkylsulfonyloxy groups, substituted or unsubstituted arylsulfonyloxy groups or the like. Preferred leaving groups are halogen and the most preferred leaving groups are bromine (compound Va) and chlorine (compound Vb). Protecting groups (PG) are described in Step 6; a benzyl group is the most preferred protecting group.

The alkylation reactions are conveniently carried out in a suitable inert organic solvent or mixture of such solvents and in the presence of a base and a suitable amount of a catalyst. Exemplary solvents include substituted or halogenated hydrocarbons such as methylene chloride, dichloroethane etc.; ether, e.g., THF, dioxane, dimethoxyethane and polar aprotic solvents, e.g., DMF, DMA, NMP, DMSO and the like. Preferred solvents are polar aprotic solvents. 1.0-1.5 equivalents of compound V may be used, and 1.1 equivalents are preferred. Exemplary bases include tertiary amines, e.g., triethylamine, pyridine, alkali metal carbonate, alkali metal hydrogen carbonate or sodium hydride. Preferred bases are alkali metal hydrogen carbonates and most preferred is sodium hydrogen carbonate. 1.5-2.5 equivalents of the base may be used, and 2.0 equivalents are preferred. Exemplary catalysts for acceleration of the reaction include alkali metal halides or tetraalkylammonium halides. If the leaving group is chloride, then the corresponding bromides or iodides are preferred and most preferably, sodium bromide or sodium iodide. At least 0.1 equivalents of the catalyst may be used and 0.15 equivalents are preferred. In a preferred embodiment, the reaction may be carried out at temperatures between about room temperature and about 80° C. Lower temperatures may prolong the reaction time and higher temperatures may cause side reactions. After the reaction is completed, the mixture can be worked up by an extractive method as known in the art. Evaporation of the solvent after the extraction and crystallization of the diastereomeric mixture by using a suitable antisolvent delivers the diastereomeric compounds IXa and IXb, which may be separated by column chromatography or by fractional crystallization from a suitable solvent. Since the compounds IXa and IXb have basic properties, the fractional crystallization may be carried out with the free amine mixture or with appropriate salts. Advantageously, the separation of a mixture of compounds IXa and IXb could be effected by fractional crystallization of the free amines from acetonitrile as solvent. Suitable derivatization of compounds IXa and IXb may also be useful for separation of the diastereomeric mixture. Surprisingly, the inventors have discovered that the diastereomer IXb can be selectively silylated in the presence of the diastereomer IXa. Because of the higher solubility of the silylated compound IXb compared with the non-silylated compounds, the efficiency of the fractional crystallization can be significantly increased. In general, the silylation may be carried out in organic solvents or mixture of solvents such as ethers, esters, halogenated hydrocarbons, aromatic solvents (e.g., toluene, chlorobenzene, etc.), polar aprotic solvents (e.g., DMF, DMSO) with a silylating reagent, if necessary in the presence of a base. Preferred organic solvents include acetonitrile, THF and MTBE and mixtures thereof. If bases are necessary, then amines, e.g., triethylamine, pyridine, imidazole, etc., alkali metal carbonate or alkali metal hydrogen carbonate may be used. Amines are the preferred organic solvents and the most preferred is imidazole. 1.0-2.0 equivalents of the base may be used, and 1.5 equivalents are preferred. As a silylating reagent, TMSCl, HMDS, BSU, etc. may be used, but TMSCl is preferred. For a successful separation of the diastereomers, it is important to use the silylating reagent in molar ratios of 0.40/n to 0.60/n with regard to the total amount of both diastereomers, wherein n is the possible amount of transferred silyl groups per silylating reagent. Fewer equivalents may give an insufficient separation and more equivalents may result in the loss of a yield. The reaction is typically carried out in a temperature range between about 0° C. and about room temperature. Lower temperature may prolong the reaction time and higher temperatures may cause an insufficient selectivity.

With regard to the present strategy for the preparation of Nebivolol, the isolation of compound IXa from a mixture consisting of IXa and IXb by fractional crystallization or by selective derivatization of IXb followed by crystallization of IXa is preferred.

Figure 3:
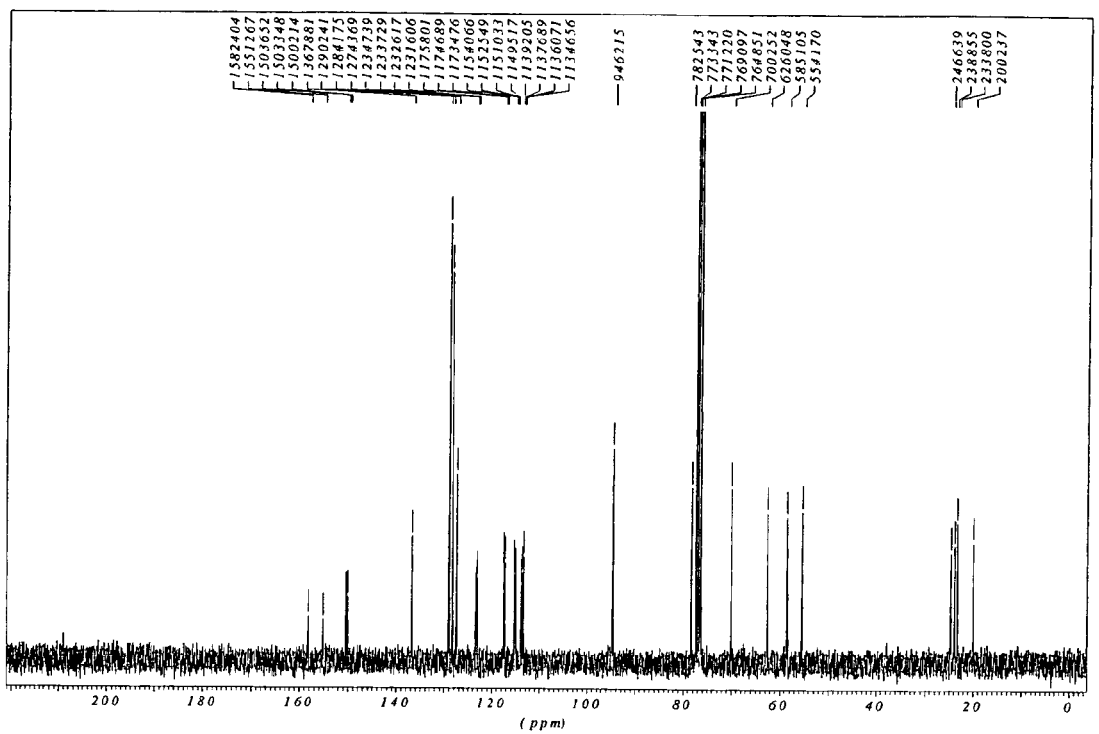
FIG. 3 is a $^{13}$C-NMR graph of compound IXa in a cyclic semi-ketal form.
Figure 4:
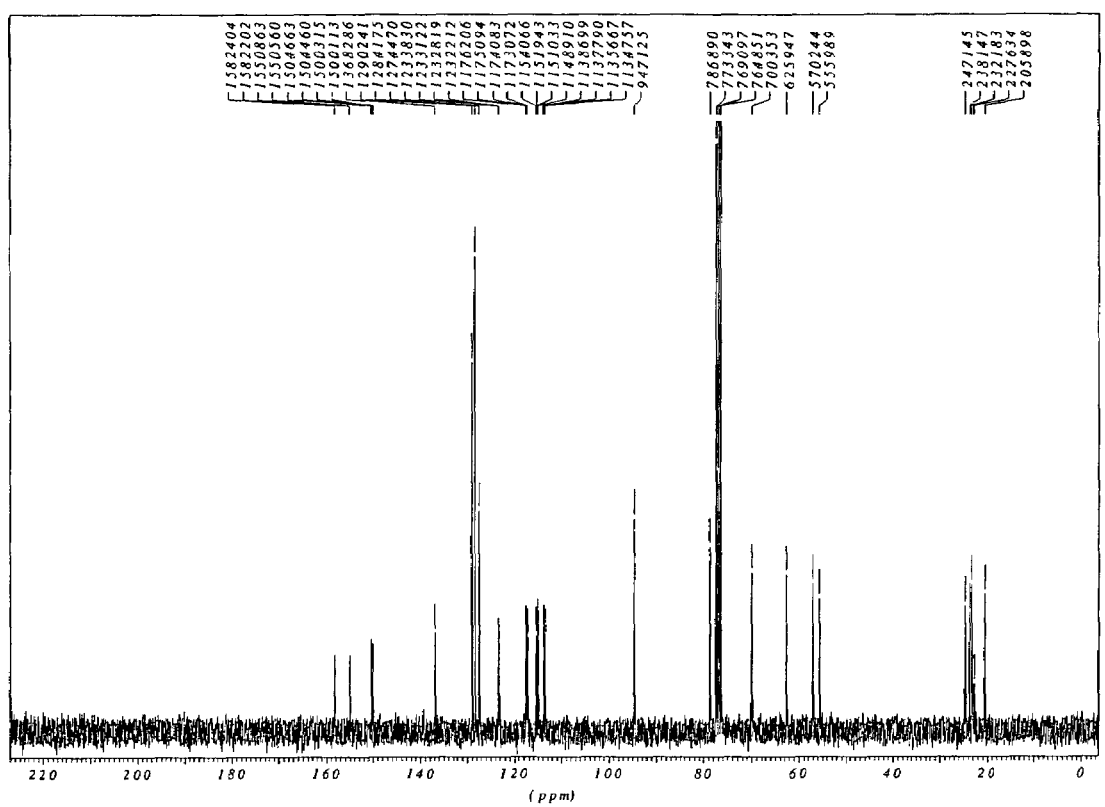
FIG. 4 is a $^{13}$C-NMR graph of compound IXb in a cyclic semi-ketal form.
Figure 5:
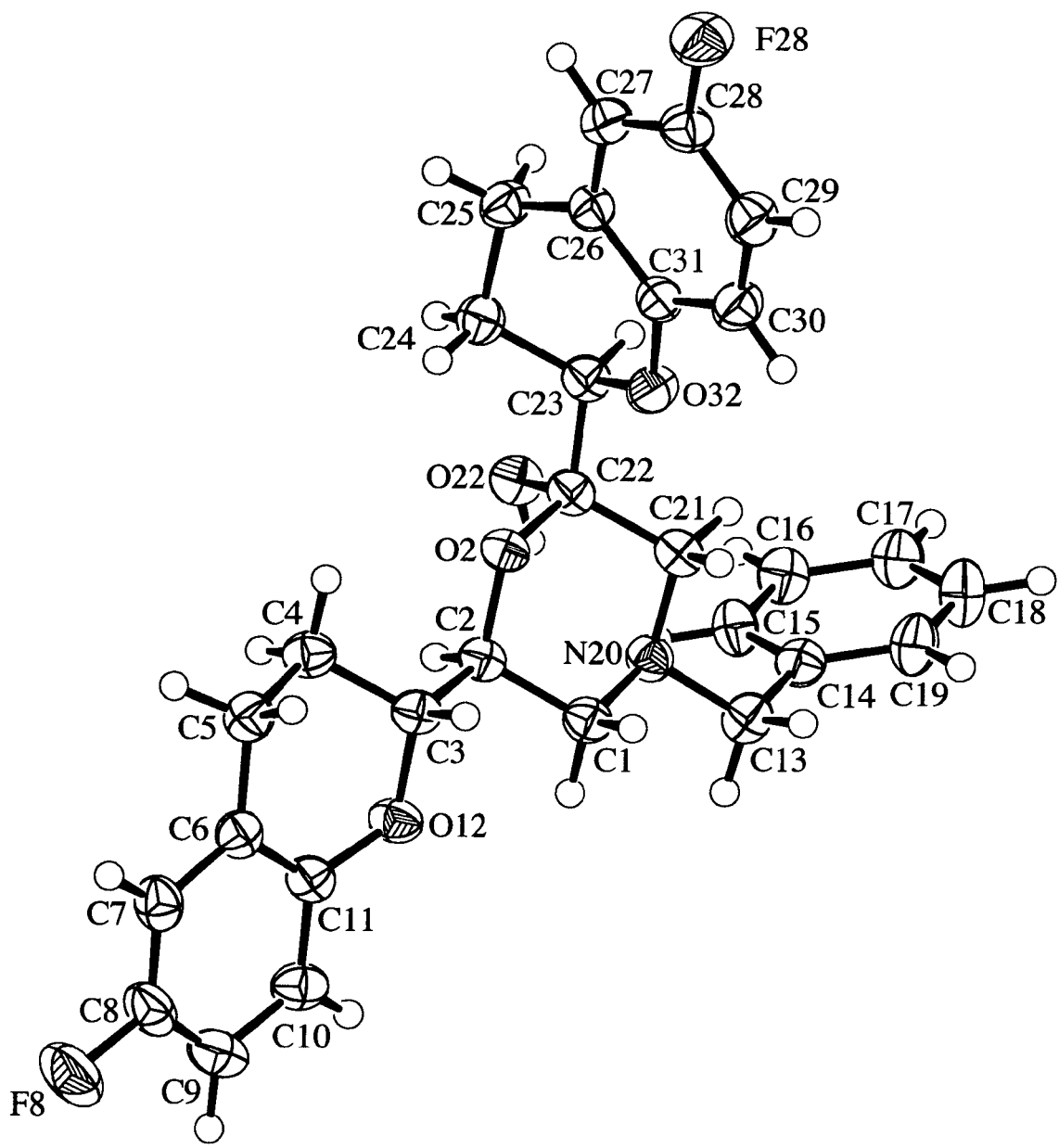
FIG. 5 is an atom-numbering schematic representation of the molecule of compound IXb in a cyclic semi-ketal form.
Figure 6:
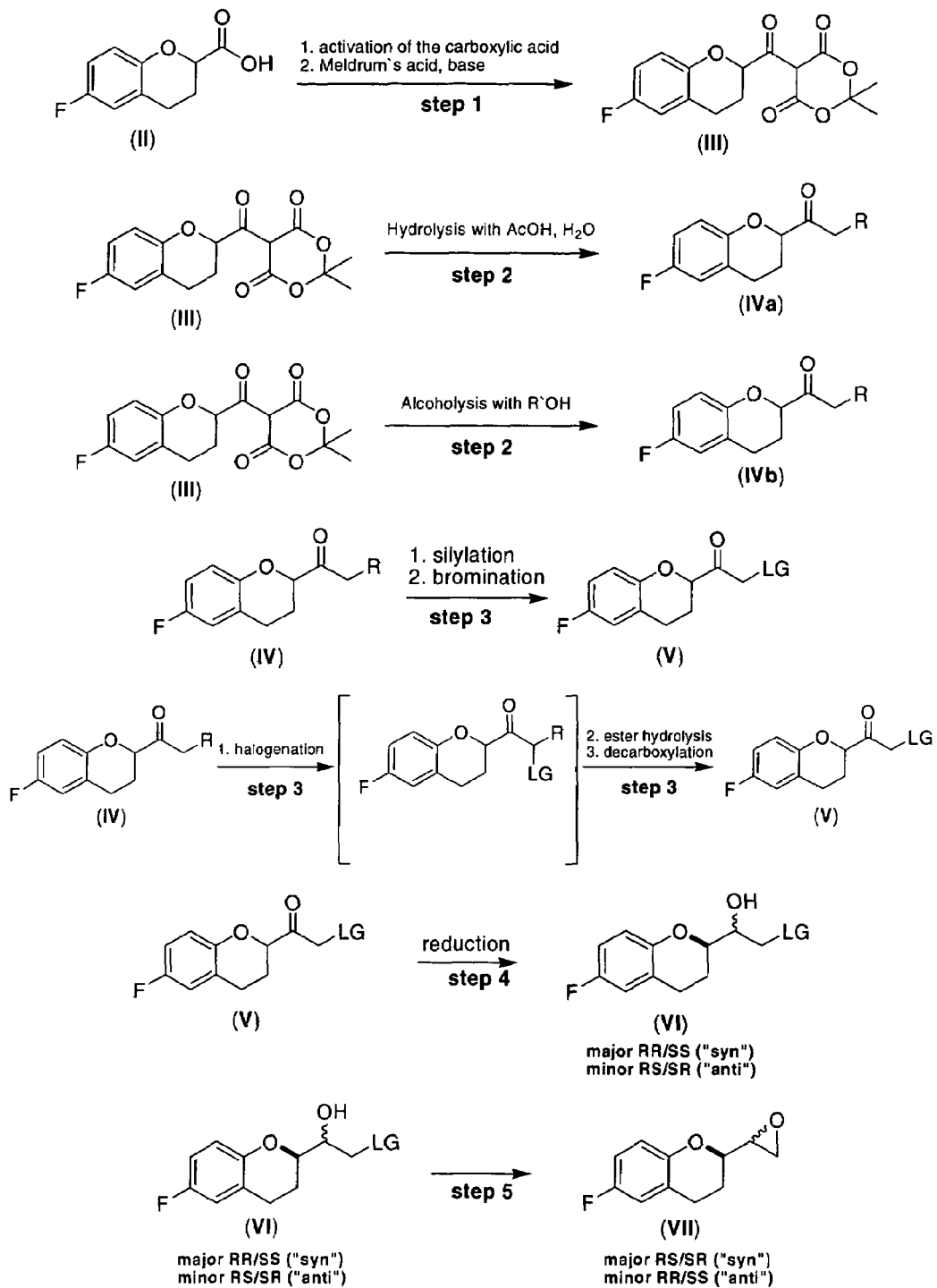
FIG. 6 is a scheme demonstrating a process of making racemic Nebivolol and its pharmaceutically acceptable salts.
Figure 6:
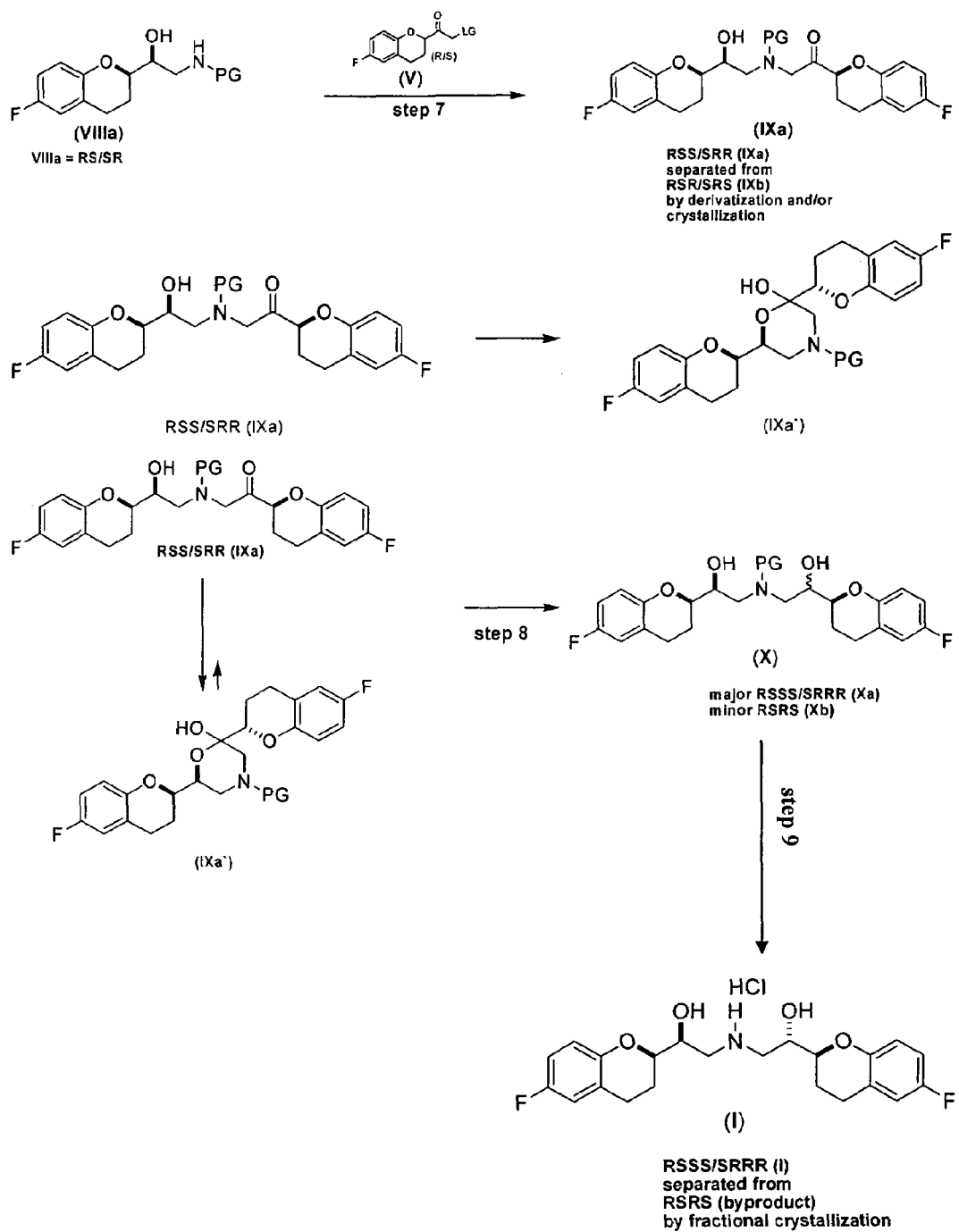

NMR measurements of the separated diastereomers have indicated that both isomers cyclize to a semi-ketal form. $^{13}$C-NMR spectra showed that instead of the carbonyl peaks, new peaks at 94.616 and 94.707 respectively were present, which indicated a carbon atom of the cyclic semi-ketal form (see Schemes 16 and 17 and FIGS. 3 and 4).

Scheme 16

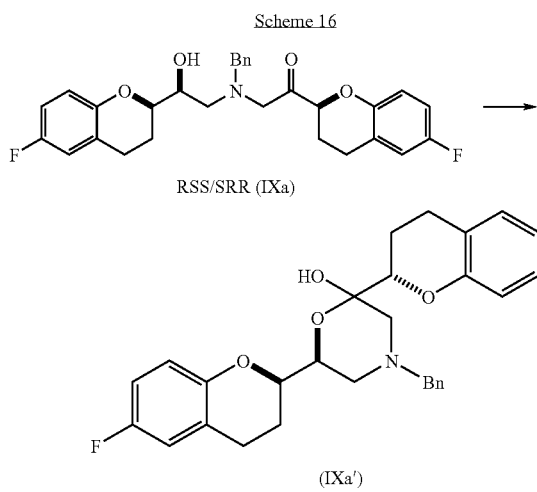

RSS/SRR (IXa)

(IXa')

Scheme 17

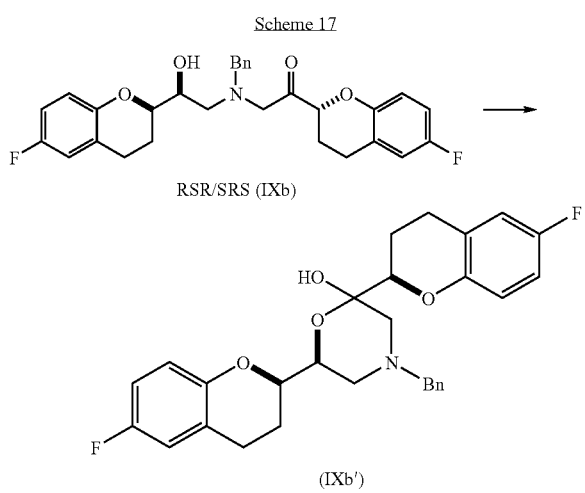

RSR/SRS (IXb)

(IXb')

The relative configuration of the compound IXb' was confirmed by single X-ray measurement as shown below:

TABLE 4

Crystallographic data of compound IXb'

| | |
|---|---|
| Crystallized from | MeCN |
| Empirical formula | $C_{29}H_{29}F_2NO_4$ |
| Formula weight [g mol$^{-1}$] | 493.55 |
| Crystal colour, habit | colorless, prism |
| Crystal dimensions [mm] | 0.25 × 0.25 × 0.28 |
| Temperature [K] | 160(1) |
| Crystal system | monoclinic |
| Space group | $P2_1/n$ (#14) |
| Z | 4 |
| Reflections for cell determination | 5882 |
| 2θ range for cell determination [°] | 4-55 |
| Unit cell parameters   a [Å] | 14.0502(3) |
| b [Å] | 11.3937(3) |
| c [Å] | 15.5302(3) |
| α [°] | 90 |
| β [°] | 100.145(1) |
| γ [°] | 90 |
| V [Å$^3$] | 2447.3(1) |
| F(000) | 1040 |
| $D_x$ [g cm$^{-3}$] | 1.339 |
| μ(Mo Kα) [mm$^{-1}$] | 0.0986 |
| Scan type | φ and ω |
| $2\theta_{(max)}$ [°] | 55 |

TABLE 4-continued

Crystallographic data of compound IXb'

| | | |
|---|---|---|
| Total reflections measured | | 54789 |
| Symmetry independent reflections | | 5601 |
| $R_{int}$ | | 0.057 |
| Reflections with I > 2σ(I) | | 4092 |
| Reflections used in refinement | | 5598 |
| Parameters refined | | 330 |
| Final | R(F) [I > 2σ(I) reflections] | 0.0468 |
| | wR(F$^2$) (all data) | 0.1252 |
| Weights: | | w = [σ$^2$(F$_o^2$) + (0.0616P)$^2$ + 0.3697P]$^{-1}$ where P = (F$_o^2$ + 2F$_c^2$)/3 |
| Goodness of fit | | 1.052 |
| Secondary extinction coefficient | | 0.012(2) |
| Final Δ$_{max}$/σ | | 0.001 |
| Δρ (max; min) [e Å$^{-3}$] | | 0.27; −0.21 |
| σ(d$_{(C-C)}$) [Å] | | 0.002 |

Step 8 involves preparation of compound X as shown in Scheme 18. Non-limiting examples of compound X include (±)-[2R*[R*[R*(S*)]]]-α,α'-[[(phenylmethyl)imino]bis(methylene)]-bis[6-fluoro-chroman-2-methanol] (intermediate Xa) and (±)-[2R*[S*[R*(S*)]]]-α,α'-[[(phenylmethyl)imino]bis(methylene)]bis[6-fluoro-chroman-2-methanol] (compound Xb). A variety of reducing agents may be used for reduction of compound IXa, whereupon two racemic diastereomers can be formed having the RSSS/SRRR configuration (compound Xa) or the RSRS configuration (compound Xb). With regard to the Nebivolol synthetic strategy as depicted in Schemes 6a and 18, reduction methods giving the compound Xa in excess are preferred. There are few investigations of the selective reductions of chiral 1-hydroxy-5-keto compounds controlled by stereogenic centres at remote positions of the chain (distance of four or more atom centers; Tetrahedron Letters 35 (1994) 4891-4894, Tetrahedron Letters 40 (1999) 593-596, J. Org. Chem. 63 (1998) 7964-7981). In contrast to these investigations, compound IXa contains three asymmetric centres especially in 1-2, as well as in 1-5 and 1-6 position, which may control the diastereoselectivity in the reduction of the keto group.

Scheme 18:

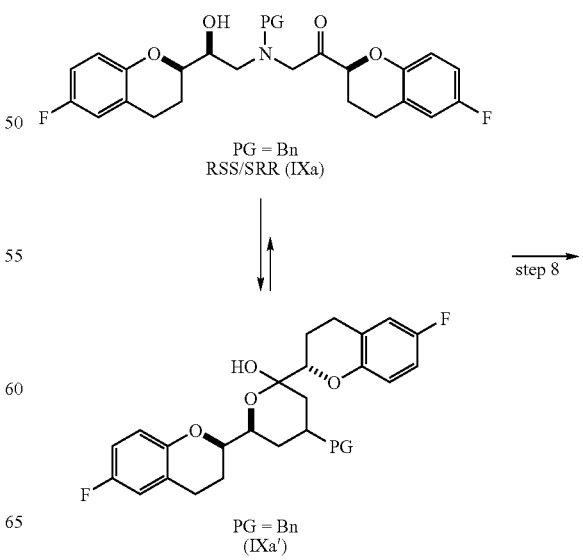

PG = Bn
RSS/SRR (IXa)

step 8

PG = Bn
(IXa')

-continued

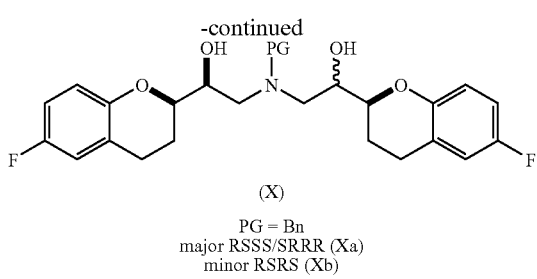

(X)

PG = Bn
major RSSS/SRRR (Xa)
minor RSRS (Xb)

PG may be hydrogen or an appropriate amine protecting group as defined above. Preferred are the same protecting groups as already described for Steps 6a-c and 7.

There is in principle no limitation in the use of borohydride or aluminiumhydride reduction reagents which may be selected from, e.g., $LiBH_4$, $NaBH_4$, $KBH_4$ $N(nBu)_4BH_4$, $Zn(BH_4)_2$, $NaH(Oac)_3$, Superhydride®, Red-Al, Li-Selectride, $BH_3xSMe_2$ or the like, or such reagents which are useful for Meerwein PondorfVerley reductions. However, it must be considered that Meerwein Pondorf Verley reductions are reversible (Oppenauer Oxidation). Since compound Xa contains two secondary alcohol groups which may be in an oxididation/reduction equilibrium with the reduction reagent, a mixture of three diastereomers (benzylated Nebivolol (RSSS/SRRR) and the two meso forms thereof (RSRS and RRSS)) may be formed.

To avoid such side reactions, the hydroxyl group of compound IXa may be protected before the Meerwein Ponndorf Verley reduction is carried out. Another possibility is the continuous distillation of the ketone (e.g. acetone if isopropanol is used as hydride donor).

Catalytic hydrogenation of compound IXa may be a further option but if PG is a reduction labile protective group (e.g. benzyl) then deprotection must be taken into account.

The reductions may be carried out in absence or in presence of a Lewis acid selected from $MgCl_2$, $CaCl_2$, $BaCl_2$, $ZnCl_2$ $Al(Oalkyl)_3$, $Ti(Oalkyl)_4$ $BF_3xOEt_2$ or the like. Suitable solvents are ether, alcohols, halogenated hydrocarbons, or the like, with the exception that halogenated solvents are unsuited for catalytic reductions. The reduction is conveniently carried out at −20° C. to room temperature. Even though lower temperatures may increase the selectivity, the reaction time will be extended, and higher temperature may cause a lost of selectivity. Table 5 shows typical results for the selective reduction of compound IXa.

In Table 2, incomplete conversion is marked with the symbol "*."

The ratio of diastereomeric configurations RSSS/SRRR to RSRS is from about 1 to about 20, preferably 2 to 20, and most preferably 4 to 20.

After a complete conversion, the work up procedure can be done in a normal manner. The diastereomeric product mixture may be separated by column chromatography or by fractional crystallization. Since the compounds Xa and Xb have basic properties, salt formation prior to the fractional crystallization is a further option. The diastereomeric product mixture may be also used as crude product without further purification for the next step.

Step 9 involves preparation of (±)-[2R*[R*[R*(S*)]]]-α, α'-[iminobis(methylene)]bis[6-fluoro-chroman-2-methanol] hydrochloride (compound I) and separation from the byproduct (±)-[2R*[S*[R*(S*)]]]-α,α'-[iminobis-(methylene)]bis [6-fluoro-chroman-2-methanol] hydrochloride as shown in Scheme 19.

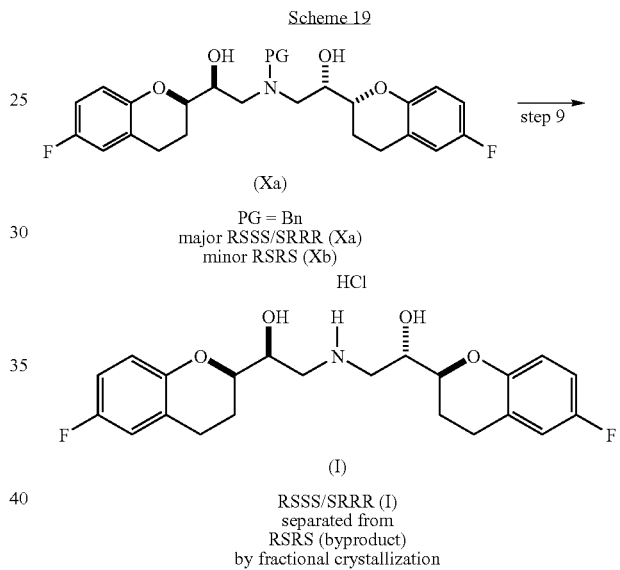

Scheme 19

(Xa)

PG = Bn
major RSSS/SRRR (Xa)
minor RSRS (Xb)

HCl (I)

RSSS/SRRR (I)
separated from
RSRS (byproduct)
by fractional crystallization

The final steps for the preparation of racemic Nebivolol hydrochloride include deprotection, salt formation and purification by fractional crystallization to remove the byproducts, mainly the undesired diastereomer having the RSRS configuration.

TABLE 5

| Reagent (eq.) | Catalyst (eq.) | Solvent | Temperature [° C.] | Time [h] | Ratio Xa//Xb RSSS/SRRR//RSRS |
|---|---|---|---|---|---|
| $NaBH_4$ (1) | none | $THF/EtOH/H_2O$ | RT | 3 | 50//50 |
| $LiBH_4$ (1) | none | THF | 0-5 | 5 | 70//30 |
| $LiBH_4$ (1) | $Ti(OiPr)_4$ (2) | THF | −20 to −RT | 3 | 78//22 |
| $LiBH_4$ (1) | $Ti(OiPr)_4$ (2) | THF | 0-5 | 2 | 82//18 |
| $Zn(BH_4)_2$ (1) | none | $Et_2O$/THF | RT | 3 | 77//23* |
| $KBH_4$ (1) | $ZnCl_2$ (2) | MeOH/THF | 0-5 | 2 | 83//17* |
| K-Selectride (2) | none | THF | 0-5 | 3 | 84//16 |
| K-Selectride (4) | $Ti(OiPr)_4$ (2) | DCM/THF | 0-5 | 3 | 83//17* |
| $KBH_4$ (1) | LiCl | THF | 0-5 | 18 | 70//30 |
| $Bu_4BH_4$ (1) | none | THF | 0-RT | 24 | 94.4//5.6 |
| $KBH_4$ (1) | $Ti(OiPr)_4$ (2) Diglyme (3) | THF | 0-RT | 26 | 94.5//4.5 |
| $KBH_4$ (1) | $Ti(OiPr)_4$ (2) | DME | 0-RT | 26 | 94.5//4.5 |

PG may have the same meaning as already described above, and if PG is other than hydrogen, the deprotection may be carried out by known procedures. Since benzyl groups are most preferred, the deprotection can be carried out by catalytic hydrogenation. If compound Xa contains compound Xb as a byproduct, then the purification may be done by fractional crystallization. Since compounds Xa and Xb have basic properties after deprotection, the fractional crystallization may be done after an appropriate salt formation. It was found that a mixture consisting of Nebivolol and its RSRS diastereomer can be readily separated by fractional crystallization after formation of the HCl salt or any other pharmaceutically acceptable salt.

Compound I may be converted to its pharmaceutically acceptable non-toxic acid addition salt formed by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propane-tricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

The salt formation using HCl is preferred for the fractional crystallization to provide readily pharmaceutically acceptable HCl salt of Nebivolol. The fractional crystallization may be generally done in suitable solvents in which Nebivolol is less soluble than its RSRS diastereomer. Alcohols as solvents for the fractional crystallization are preferred and methanol is the most preferred solvent.

Steps for Recycling of Diastereomers

This invention also includes steps for the diastereomer recycling formed during the process.

I. Recycling options for the intermediates formed in Step 5 and Step 6

A non-limiting example of recycling is illustrated in Scheme 20 using Cl as a leaving group.

The recycling step can be conducted using e.g. a Mitsunobu reaction for inversion of the secondary alcohol group for recycling of the undesired diastereomer VIII(b) formed in Step 6. However, a suitable protection (PG') of the nitrogen may be required. As a person skilled in the art would appreciate, examples of suitable protective groups PG' include formation of corresponding carbamates by using e.g., alkyl chloroformates or formation of corresponding amides by using carboxylic acid chlorides or anhydrides. The protective group can be introduced after separation of the diastereomeric mixture by fractional crystallization followed by isolation of the undesired diastereomer from the mother liquors.

Scheme 20

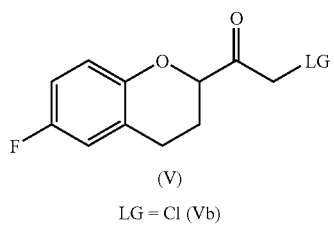

(V)

LG = Cl (Vb)

step 4

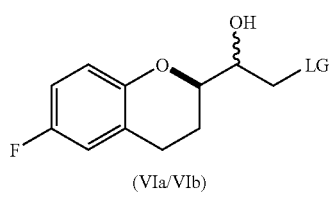

(VIa/VIb)

LG = Cl:
major RR/SS ("syn", VIa)
minor RS/SR ("anti", VIb)

step 5

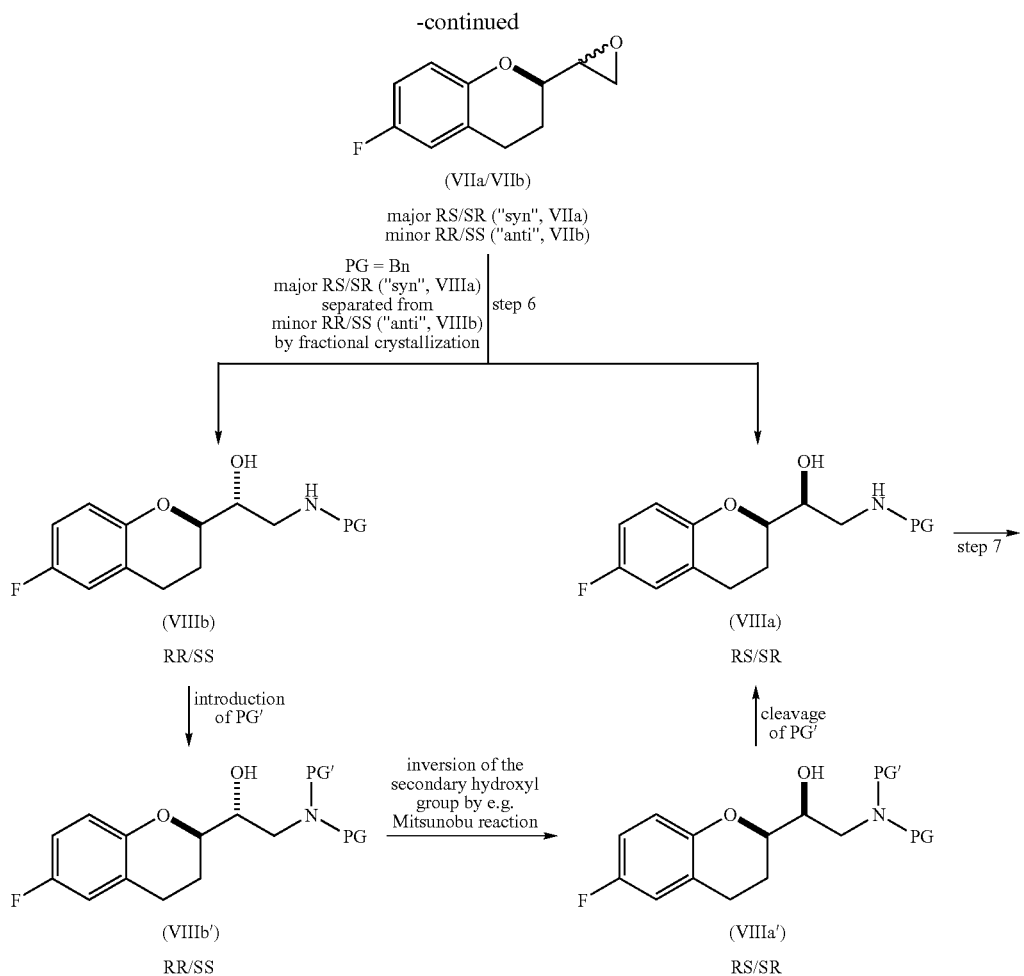

II. Recycling option for compounds formed in Step 7

In Step 7, a mixture of two diastereomers is formed (compounds IXa and IXb) which is separated by fractional crystallization. There are two options for a recycling of the undesired diastereomer IXb (Scheme 21, Tables 6, 7, 8). The first one is an epimerization of the undesired diastereomer IXb to give again a mixture consisting of IXa and IXb which can be separated by the above described method.

TABLE 6

Epimerization studies in various solvents containing 10% 1,8-Diazabicyclo[5.4.0]undec-7-ene (DBU), starting from IXa/IXb ratio of about 23/77. The mixtures were analyzed after 40 h by HPLC.

| Solvent | Temperature [° C.] | Ratio of compounds IXa/IXb | Ratio of compounds IXa + IXb/VIIIa |
|---|---|---|---|
| MeOH | RT | 69/31 | 20/80 |
| DMF | RT | 53/47 | 85/15 |
| Acn | RT | 53/47 | 71/29 |
| THF | 40 | 53/47 | 61/39 |
| AcOEt | 40 | 54/46 | 74/26 |
| Toluene | 40 | 55/45 | 81/19 |

The results in Table 6 show that the cleavage of the compounds IXa/IXb in methanol to the compound VIIIa is faster than the epimerization. Epimerization in all other solvents gave after 40 h an almost 1/1 mixture of the diastereomers IXa and IXb, whereas the tendency for cleavage to compound VIIIa is accurately suppressed especially in DMF and toluene as solvent. Further investigations of epimerization in DMF and toluene are shown in Tables 7 and 8.

TABLE 7

Epimerization studies in DMF containing 5% 1,8-Diazabicyclo[5.4.0]undec-7-ene (DBU) at 30° C., starting from IXa/IXb ratio of about 23/77. The mixtures were analyzed by HPLC

| Time [h] | Ratio of compounds IXa/IXb | Ratio of compounds IXa + IXb/VIIIa |
|---|---|---|
| 1 | 28/72 | 98.3/1.7 |
| 2.5 | 31/69 | 97.4/2.6 |
| 5.5 | 37/63 | 95.6/4.4 |
| 22.5 | 50/50 | 91.3/8.7 |
| 45.5 | 54/46 | 87.8/12.2 |

TABLE 8

Epimerization studies in toluene containing 5%
1,8-Diazabicyclo[5.4.0]undec-7-ene (DBU) at
30° C., starting from IXa/IXb ratio of about
23/77. The mixtures were analyzed by HPLC

| Time [h] | Ratio of compounds IXa/IXb | Ratio of compounds IXa + IXb/VIIIa |
|---|---|---|
| 1 | 24/76 | 99.7/0.3 |
| 5.5 | 27/73 | 99.4/0.6 |
| 22.5 | 33/67 | 98.3/1.7 |
| 45.5 | 43/58 | 96.0/4.0 |

The second recycling option includes the cleavage of the undesired diastereomer IXb to give a mixture of compound VIIIa and some byproducts. The cleavage may be done by a tautoterism of the aminoketone into the enamine form followed by hydrolysis using methods known in the art. The compound VIIIa could then be isolated and reintroduced into the process again as shown in Scheme 21.

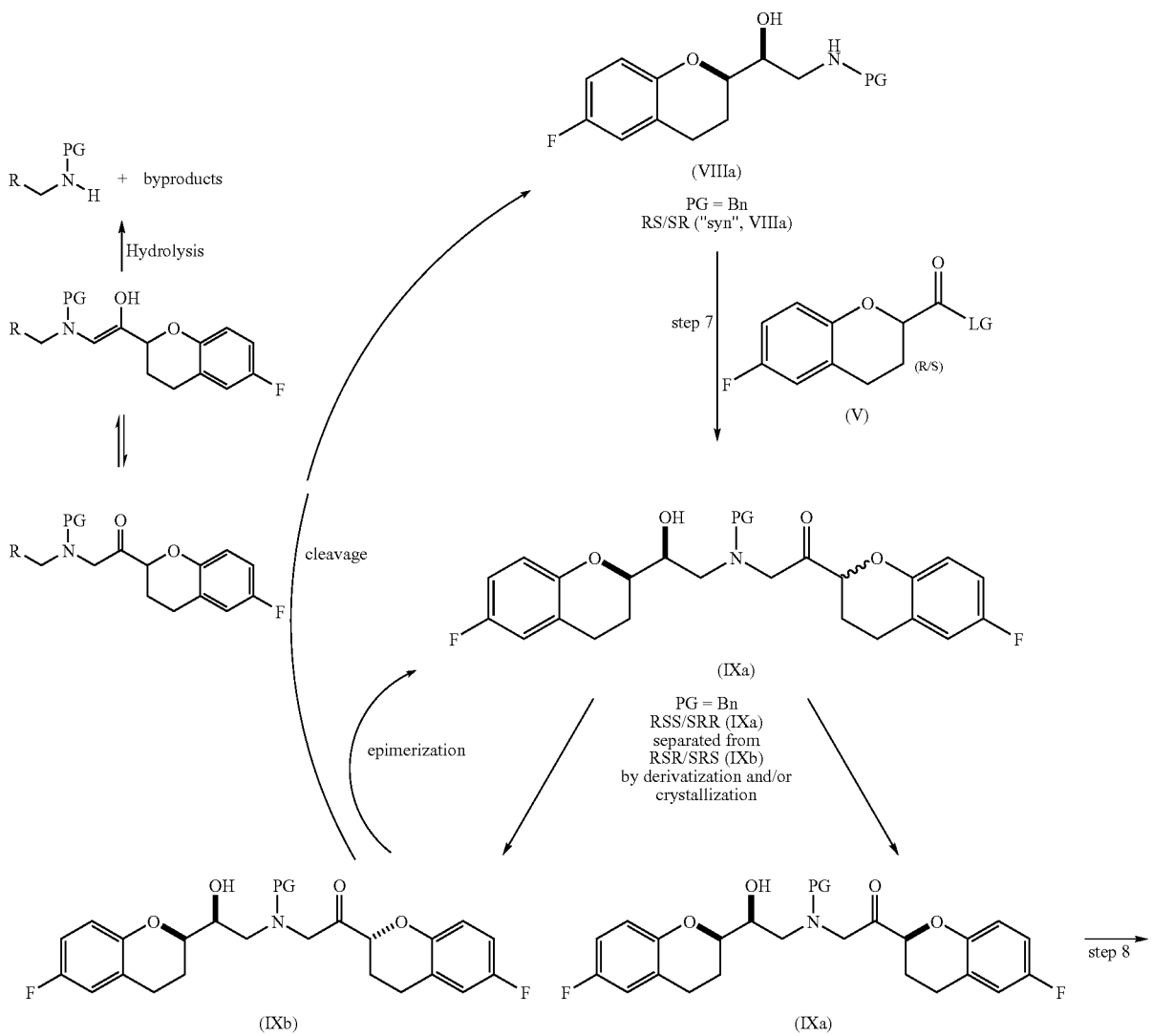

III. Alternative synthesis of Nebivolol using the diastereomer VIIb
Although, in accordance with the above described synthetic strategy producing the diastereomer VIIIa as an intermediate is preferred, the undesired diastereomer VIIIb can also be used as intermediate for the preparation of racemic Nebivolol as shown in Scheme 22.
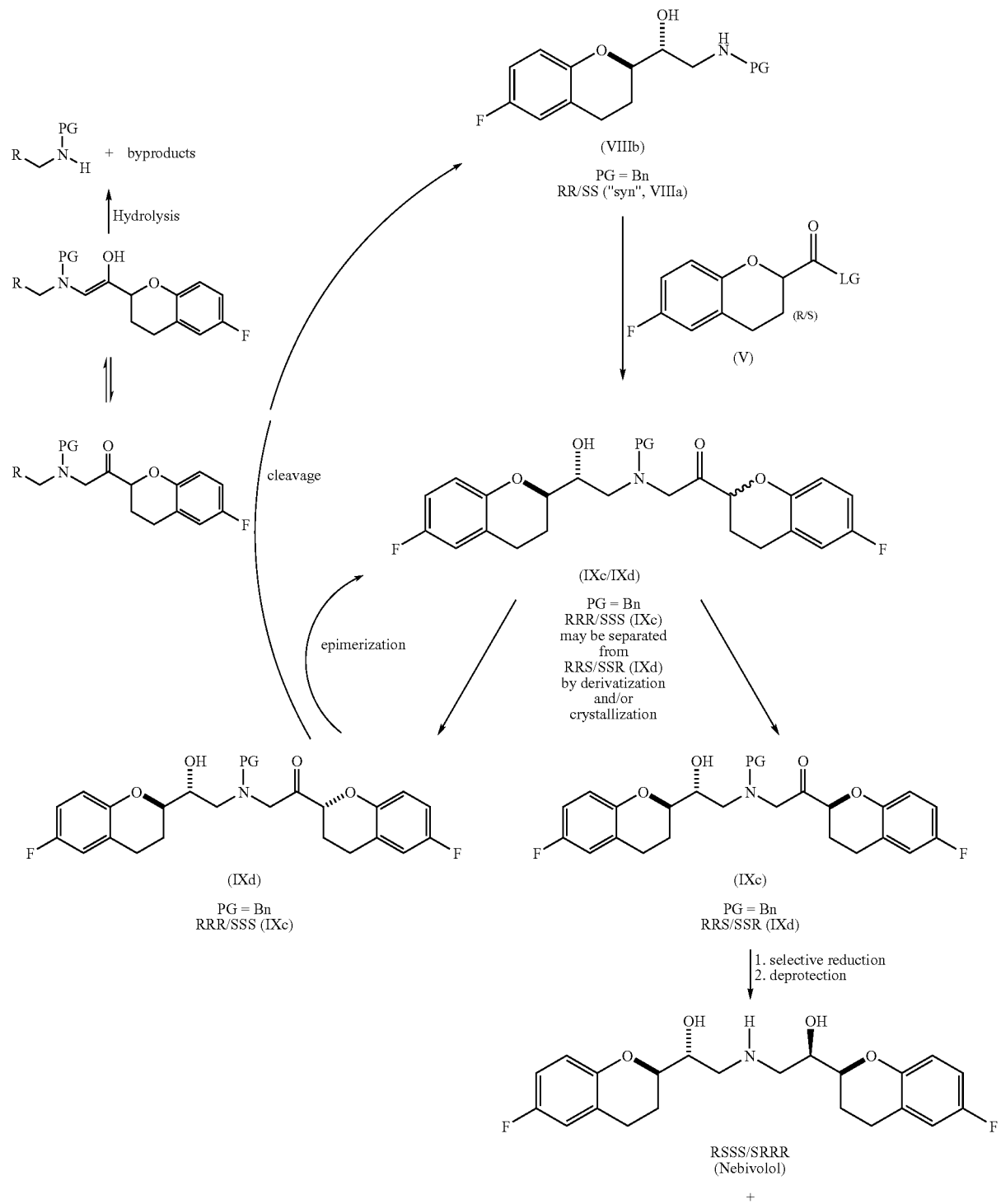

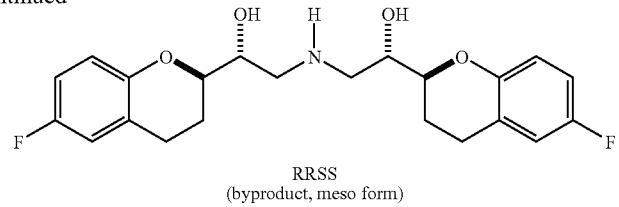

RRSS
(byproduct, meso form)

Other similar recycling methods are also possible. For example, in contrast to the route using the preferred compound VIIIa, the use of compound VIIIb will deliver after the alkylation step a diastereomeric mixture of compounds IXc and IXd. Reduction of compound IXd will give after deprotection Nebivolol and the second meso form having the RRSS configuration (in contrast, the preferred route produces the meso form having RSRS configuration). As mentioned above, the meso form having RSRS configuration is more soluble than the second meso form (RRSS), and therefore, Nebivolol contaminated with the RSRS diastereomer (according to the preferred route) can be easily purified by recrystallization. In case of RRSS contamination of Nebovolol, purification could be also carried out by recrystallization, but due to the similar solubility of the RRSS diastereomer compared with the solubility of Nebivolol, the purification is more difficult and loss of yield has to be taken into account.

IV. Recycling of the Nebivolol meso forms (RSRS and RRSS)

Both Nebivolol meso forms obtained according to the above described processes may be directly converted to Nebivolol after a suitable protection (e.g. cyclic carbamate, cyclic silyl group etc.), followed by inversion of the secondary alcohol group (e.g. by Mitsunobu reaction) and deprotection as shown in Scheme 23.

Scheme 23

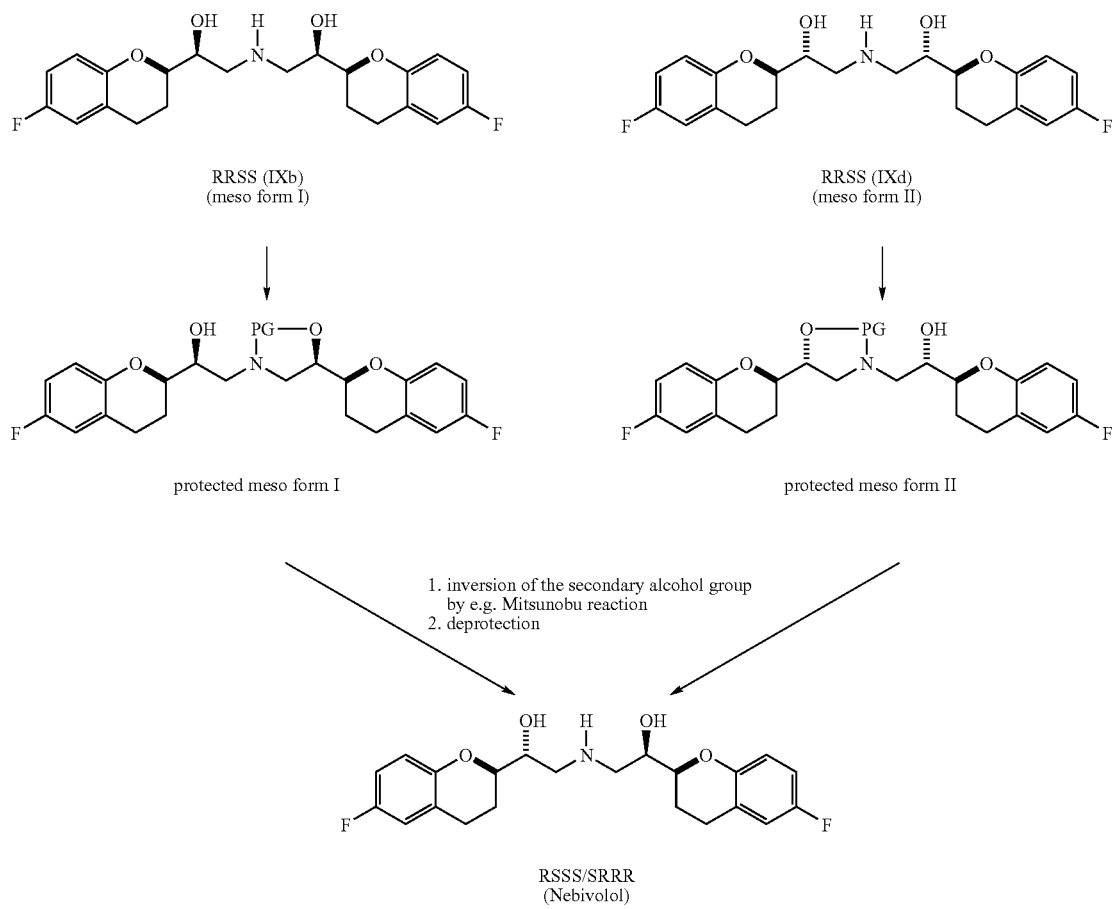

Reactions for protecting, deprotecting and inversion can be performed by methods known in art.

The invention will be illustrated in more detail with reference to the following Examples, but it should be understood that the present invention is not deemed to be limited thereto.

EXAMPLES

Example 1

Step 1: Preparation of (±)-5-[6-fluorochroman-2-carbonyl]-2,2-dimethyl[1,3]dioxane-4,6-dione (compound III).

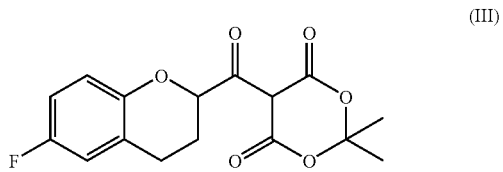

(III)

Thionylchloride (109.21 g, 918 mmol) was added under nitrogen atmosphere at 20-25° C. to a suspension of 6-fluorochroman-2-carboxylic acid (90.00 g, 459 mmol) and DMF (1.68 g, 23 mmol) in toluene (635 ml). Afterwards, the suspension was heated to an internal temperature of 60-70° C., whereupon a clear yellow solution was obtained under simultaneous evolution of a gas. The reaction was completed within 70 min at this temperature, and the mixture was then concentrated in vacuum (bath temperature 45-50° C., pressure≦35 mbar) to yield the chroman-2-carboxylic acid chloride as a yellow oil (112.65 g). The crude product was dissolved in methylene chloride (65 ml) and added slowly under nitrogen atmosphere to a solution of Meldrum's acid (70.90 g, 482 mmol) and pyridine (72.62 g, 918 mmol) in methylene chloride (261 ml) at an internal temperature of 0-10° C. The reaction mixture was allowed to warm to 20-25° C. within 50 min. and stirred at this temperature for additional 30 min. Methylene chloride (325 ml) and water (325 ml) were then added to the formed brown suspension. The two phase mixture was stirred for 5 min, separated, and the organic layer was subsequently extracted twice with water (200 ml each), then with 2N aqueous HCl solution (250 ml) and finally with water (250 ml). After drying over Na$_2$SO$_4$, the organic layer was filtrated and concentrated in vacuo (≦50 mbar) to give a brown, viscous oil (170.76 g), which crystallized after 10 min at room temperature. The solid was slurried at 20-25° C. in diisopropyl ether (500 ml) for 2 h. After filtration of the suspension, the wet product was washed with diisopropyl ether (70 ml) and dried in vacuo (13 h at 40° C.) to give a yellow-ocher colored solid (yield: 114.71 g, HPLC-purity: 96.98%).

Example 2

Step 2, route A: Preparation of (±)-1-(6-fluoro-chroman-2-yl)-ethanone (compound IVa)

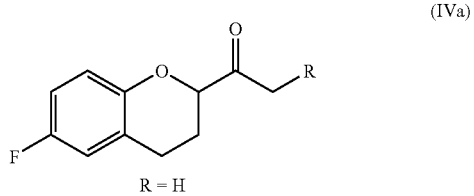

(IVa)

R = H

Example 1 was reproduced using 16 g of 6-fluorochroman-2-carboxylic acid, and the residue obtained after work up and evaporation of methylene chloride was used directly for Step 2, route A. A mixture of thus obtained crude product (compound III) with water (40 ml) and acetic acid (40 ml) was heated for 70 min to reflux and then cooled to room temperature. The reaction mixture was extracted with methylene chloride (40 ml), and the organic layer was twice washed with 1 N aqueous NaOH solution (each 20 ml). After drying over MgSO$_4$, the organic layer was filtrated and evaporated. The residue was purified by column chromatography over silica gel using ethylacetate/cyclohexane (⅓ by volume) as eluent. Collection of the second fraction and evaporation of the solvent gave the product as yellow oil (yield: 11.89 g, HPLC-purity: 98.76%).

Example 3

Step 2, route B: Preparation of (±)-3-(6-fluorochroman-2-yl)-3-oxo-propionic acid ethyl ester (compound IVb as ethylester).

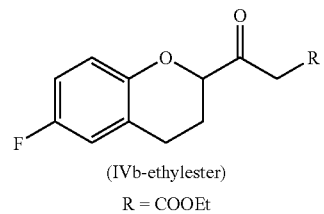

(IVb-ethylester)

R = COOEt

Example 1 was reproduced using 16 g of 6-fluorochroman-2-carboxylic acid and the residue obtained after work up and evaporation of methylene chloride was used directly for Step 2, route B. A suspension of this crude product (compound III) in ethanol (150 ml) was heated to reflux for 75 min, whereupon a clear solution was obtained. After cooling of the solution to room temperature and evaporation of the solvent, the residue was portioned between methylene chloride (80 ml) and water (80 ml). The phases were separated, and the organic layer extracted with 1 N aqueous NaOH solution (40 ml). The methylene chloride solution was dried over MgSO$_4$, filtrated and evaporated. The residue was purified by column chromatography over silica gel using ethylacetate/cyclohexane (¼ by volume) as eluent. Collection of the first fraction and evaporation of the solvent gave the product as yellow-brown oil (yield: 11.89 g, HPLC-purity: 92.45%).

Example 4

Step 2, route B: Preparation of (±)-3-(6-fluorochroman-2-yl)-3-oxo-propionic acid tert-butyl ester (compound IVb as tert-butyl ester).

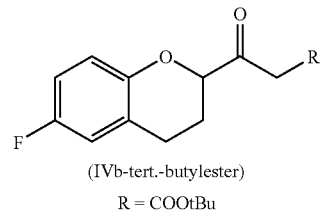

(IVb-tert.-butylester)

R = COOtBu

Tert-butanol (83.90 g) was added at room temperature to a suspension of compound III (94.00 g) (obtained by the process as described in Example 1) in toluene (280 ml). The suspension was heated to the internal temperature of 70-80° C., whereupon a clear solution was obtained under simultaneous evolution of a gas. The reaction was completed within 80 min. The mixture was cooled to room temperature and extracted successively with saturated NaHCO$_3$ solution (235 ml) and saturated NaCl solution. The organic layer was dried over Na$_2$SO$_4$, filtrated and concentrated in vacuo to give the product as an orange-brown oil (yield: 95.79 g, HPLC-purity:

97.20%; the crude product contained small amounts of toluene). The crude product was used for the next step without further purification.

Example 5

Step 3, route A: Preparation of (±)-2-bromo-1-(6-fluoro-chroman-2-yl)-ethanone (compound Va).

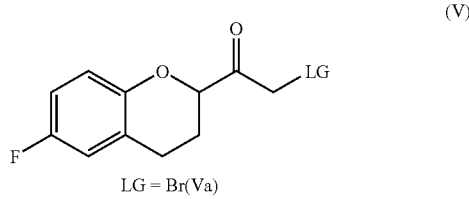

LG = Br(Va)

TMSCl (3.2 ml) was added to a solution of 2 M LDA (9.0 ml) in 20 ml THF at −78° C. within 10 min. A solution of compound IVa (3.0 g) (obtained by the process as described in Example 2) in THF (3 ml) was then added and after 10 min, the reaction mixture was allowed to warm to room temperature within 40 min. A white solid precipitated and the suspension were portioned between cyclohexane (100 ml) and cold 10% NaHCO$_3$ solution (60 ml). The aqueous layer was diluted with water (20 ml) and separated. The organic layer was extracted twice with 10% NaHCO$_3$ solution (each 30 ml), dried over Na$_2$SO$_4$ filtrated and concentrated. The residue was dissolved in methylene chloride (15 ml) and cooled to an internal temperature of 0-5° C. A suspension of NBS (2.94 g) in methylene chloride (10 ml) was added to this mixture. After stirring for 1.5-2 h at this temperature, the reaction mixture was poured into 10% NaHCO$_3$ solution (15 ml), the organic layer was separated and concentrated. The residue was purified by column chromatography over silica gel using ethylacetate/cyclohexane (1/5 by volume) as eluent. Collection of the first fraction and evaporation of the solvent gave a product mixture consisting of compound Va (78.1% by HPLC) and the corresponding byproduct (VaBP1), (VaBP1)

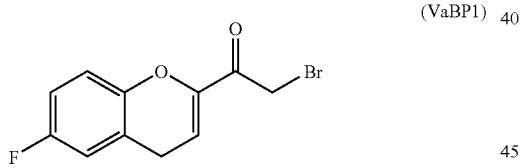

which was formed by non selective bromination followed by elimination as a yellow-brown oil (yield: 2.17 g, since compound Va seems to be less stable than compound Vb, it should be stored preferably under light exclusion at −20° C.).

Example 6

Step 3, route B: Preparation of (±)-2-bromo-1-(6-fluoro-chroman-2-yl)-ethanone (compound Va).

(V)

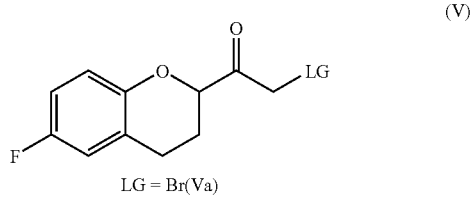

LG = Br(Va)

N-Bromo succinimide (NBS) (5.04 g) was added at 5-10° C. in portions to a solution of compound IVb-tert-butyl ester (10.0 g) (obtained by the process as described in Example 4) and Mg(ClO$_4$)$_2$ (2.32 g) in ethyl acetate (100 ml). The reaction was subsequently monitored by HPLC. After the addition, the mixture was stirred at 5-10° C. for 45 min. Since 16% of the adduct remained, additional NBS (1.0 g) was added. The mixture was stirred for 20 min at 5-10° C., then allowed to warm to room temperature and stirred for 20 min at this temperature. The precipitate was filtered off, and the mother liquor concentrated in vacuo to give 2-bromo-3-(6-fluoro-chroman-2-yl)-3-oxo-propionic acid tert-butyl ester as a red oil (15.3 g). To carry out the hydrolysis and decarboxylation, the red oil was taken up in acetic acid (42 ml) and formic acid (49 ml), and the mixture was heated to an internal temperature of 80-85° C., whereupon an evolution of a gas was observed. After 60 min, the reaction was completed, and the mixture was concentrated in vacuo to give a brown oil. The oil was then dissolved in ethyl acetate (50 ml) and n-hexane (50 ml), and the solution was extracted successively twice with semi saturated NaCl solution (each 20 ml) and with saturated NaHCO$_3$ solution (20 ml). The organic layer was dried over MgSO$_4$, filtrated and concentrated in vacuo to give an amber oil, which was taken up in cyclohexane. The crystallization was initiated at room temperature by seeding. After 45 min, the suspension was filtered to give compound Va (2.98 g, beige solid) after drying. Additional amounts of compound Va (1.9 g) was obtained from the mother liquor after stirring at 6-7° C. for 1.5 h, filtrating and drying (overall yield: 4.88 g, HPLC-purity: 98.5%; since compound Va seems to be less stable than compound Vb, it should be stored preferably under light exclusion at −20° C.).

Example 7

Step 3, route B: Preparation of (±)-2-chloro-1-(6-fluoro-chroman-2-yl)-ethanone (compound Vb).

(V)

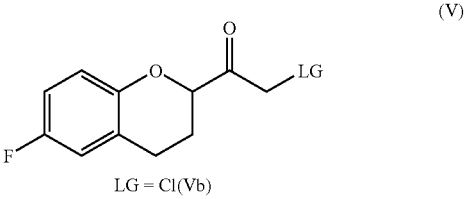

LG = Cl(Vb)

Mg(ClO$_4$)$_2$ (21.40 g) was slowly added at room temperature to a solution of compound IVb-tert-butyl ester (105.59 g) (obtained by the process as described in Example 4) in ethyl acetate (800 ml). Afterwards, NCS (41.80 g) was added in portions at 20-25° C. within 3.5-4 h, and the reaction was subsequently monitored by HPLC. After complete addition, the yellow suspension was stirred for 30 min at 20-25° C. and then filtrated. The filter cake was washed with ethyl acetate (100 ml), and the combined filtrates were extracted successively with saturated NaCl solution (150 ml) and water (150 ml) and afterwards concentrated in vacuo (60 mbar) to give a brown oil (116.82 g). To carry out the hydrolysis and decarboxylation, the brown oil was taken up in a mixture of acetic acid (420 ml), formic acid (390 ml) and water (80 ml). The solution was heated to an internal temperature of 80-90° C., whereupon an evolution of a gas was observed. After completion of the reaction (within 2 h), the solution was concentrated in vacuo (≦30 mbar) to give a dark orange oil (83.25 g), which was dissolved in ethyl acetate (400 ml). This solution was successively extracted with semi saturated NaCl solution (300 ml), saturated NaHCO$_3$ (300 ml) solution and water (100 ml). After drying over Na$_2$SO$_4$, the suspension was filtrated and concentrated to give initially a red oil (80.00 g), which slowly crystallized at room temperature. For further purification, the crude product (77.0 g) was dissolved in isopropanol (240 ml) at an internal temperature of 45-50° C. The solution was seeded to initiate the crystallization and cooled to 0-5° C. After 75 min stirring at 0-5° C., the suspension was filtrated, and the filter cake was washed with cold isopropanol (40 ml). The wet product was dried in vacuo at 35-40° C. to give a yellowish solid (57.13 g, HPLC-purity: 99.00%).

Example 8

Steps 1-3: Preparation of (±)-2-chloro-1-(6-fluoro-chroman-2-yl)-ethanone (compound Vb) from 6-fluorochroman-2-carboxylic acid (II)

A mixture of 6-fluorochroman-2-carboxylic acid (114.4 g, assay=99%, 577 mmol), thionylchloride (83.15 g, 692 mmol) and DMF (2.18 g, 30 mmol) in toluene (471 g) was slowly heated under nitrogen atmosphere to an internal temperature of 70-80° C. (at an internal temperature of 57° C. an evolution of a gas started). When the raction was complete (within 40 min at 78° C., HPLC analysis showed 98.6% of the corresponding acid chloride), an amount of 208 g solvent was distilled off in vacuum (pressure: 220 (start)-155 (end) mbar, internal temperature: 73 (start)-69 (end)° C., steam temperature: 39 (start)-63 (end)° C.). A second flask was charged with Meldrum's acid (89.1 g, 606 mmol), pyridine (89 ml, 1.11 mol) and methylenechloride (375 ml). After this mixture was cooled to an internal temperature of 0-5° C., the above prepared solution of 6-fluorochroman-2-carboxylic acid chloride in toluene was added slowly at an internal temperature of 0-5° C. The reaction mixture was then allowed to warm to 20° C. within 80 minutes (an in process HPLC analysis showed 92.6% product). Tert-butanol (81.0 g, 1.08 mol) was added and the mixture was slowly (within 4 h) heated to an internal temperature of 70-80° C. under simultaneous distillation of the solvent and evolution of a gas. During the heating up (after 75 min and at an internal temperature of 56° C.) additional tert-butanol (75 g, 1.00 mol) was added. The distillation and the evolution of the gas stopped when the internal temperature had reached 75-80° C. (at this time 370 g solvent were distilled off). When an in process HPLC anlysis showed the completion of the reaction, the mixture was cooled to 20° C. and a solution of sulfuric acid (41.8 g) in water (200 ml) was added. The organic layer was separated, extracted twice with saturated NaHCO₃ solution (each 200 ml), then concentrated in vacuo to approximately 60% of the volume (pressure: 370-150 mbar; note: during distillation the water should be removed completely) and diluted at room temperature with ethylacetate (450 ml). After addition of Na₃PO₄ (91.5 g), sulfuryl chloride (53 ml) was added slowly (within 3 h) at an internal temperature of 10-20° C. and stirring was continued until an in process HPLC analysis showed the completion of the reaction (approx. 1 h). The mixture was extracted twice with water (each 150 ml) and distilled in vacuo (pressure: 150-170 mbar) until 305 g distillate was obtained. Afterwards, acetic acid (400 ml) was added and the mixture was distilled in vacuo again (pressure: 30-40 mbar) until additional 292 g distillate were obtained. Concentrated hydrochloric acid (84 ml) was added and the mixture was stirred at an internal temperature of 40-50° C. until the reaction (hydrolysis and decarboxylation) was complete (4 h, monitored by HPLC). After 100 g solvent were distilled off in vacuo (pressure: 200-40 mbar; removal of remaining toluene and tert.-butanol), the emulsion was diluted at an internal temperature of 20° C. with acetic acid (70 ml) to give a solution. Then, water (20 ml) and seeding crystalls were added to initiate the crystallization. When the crystallization started, additional water (230 ml) was added slowly. The suspension was stirred at room temperature (15 h), then filtrated and the filter cake was washed with a mixture of acetic acid and water (v/v=1/1, 100 ml). The wet product was dried in vacuo at 40° C. to give a ocher solid (overall yield: 101.84 g, HPLC-purity: 98.9%).

Example 9

Step 4: Preparation of (±)-2-chloro-1-(6-fluoro-(2R*)-chroman-2-yl)-(1R*)-ethan-1-ol (compound VIa) and (±)-2-chloro-1-(6-fluoro-(2S*)-chroman-2-yl)-(1R*)-ethan-1-ol (compound VIb)

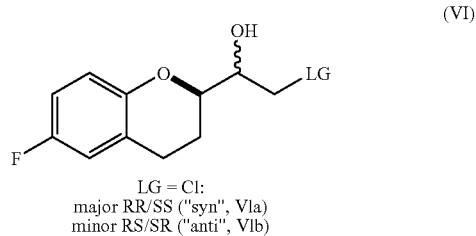

LG = Cl:
major RR/SS ("syn", VIa)
minor RS/SR ("anti", VIb)

Compound Vb (33.74 g) was added at 0-5° C. to a solution of ZnCl₂ (40.3 g) in methanol (470 ml), and the mixture was stirred until all solid was dissolved (1 h). The solution was cooled to −10° C., and NaBH₄ was added in portions within 35 min. After completion of the reaction monitored by HPLC, the mixture was concentrated to a volume of about 150 ml and then diluted with toluene (400 ml). The organic solution was successively extracted twice with 1.0 N HCl solution (each 200 ml) and with saturated NaHCO₃ solution (100 ml). After drying over MgSO₄, the suspension was filtrated, and the solvent evaporated in vacuo to give a brownish oil (35.28 g, ratio VIa/VIb=61/39; the crude product mixture contains small amounts of toluene). The crude product was used for the next step without further purification.

Example 10

Step 5: Preparation of (±)-6-fluoro-[(2R*)-oxiran-2-yl]-(2S*)-chromane (compound VIIa) and (±)-6-fluoro-[(2R*)-oxiran-2-yl]-(2R*)-chromane (compound VIIb)

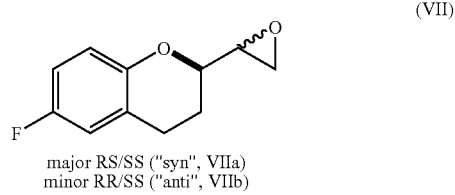

major RS/SS ("syn", VIIa)
minor RR/SS ("anti", VIIb)

A methanolic NaOMe solution (30%, 30.9 g) was added at 20-25° C. to a solution of a mixture of compounds VIa and VIb (37.9 g, ratio VIa/VIb=61/39) in methanol (380 ml). The reaction was monitored by HPLC and after stirring for 3.5 h at 20-25° C., additional methanolic NaOMe solution (30%, 1.4 g) was added. After the reaction was completed (within 3.5 h), the mixture was neutralized by addition of acetic acid and then concentrated in vacuo. The residue was portioned between methylene chloride (300 ml) and a semi saturated NaCl solution (200 ml). The phases were separated, and the organic layer was dried over MgSO₄. After filtration, the filtrate was concentrated to give a brownish oil (32.1 g, ratio VIIa/VIIb=61/39). The crude product was used directly for the next step.

Example 11

Step 6: Preparation of (±)-2-Benzylamino-1-[6-fluoro-(2R*)-chroman-2-yl]-(1S*)-ethan-1-ol (compound VIIIa) and (±)-2-Benzylamino-1-[6-fluoro-(2R*)-chroman-2-yl]-(1R*)-ethan-1-ol (compound VIIIb) and separation of the diastereomers VIIIa and VIIIb

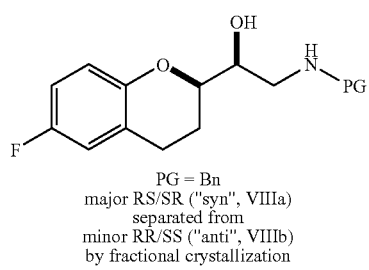

(VIII)

PG = Bn
major RS/SR ("syn", VIIIa)
separated from
minor RR/SS ("anti", VIIIb)
by fractional crystallization A mixture of compounds VIIa and VIIb (ratio: 57/43) was slowly added (within 1.5 h) at an internal temperature of 40° C. to a solution of benzylamine (5.4 g) in 2-propanol (30 ml). After completion of the reaction monitored by HPLC, the solution was cooled to room temperature and seeding material was added. Next, the diastereomers VIIIa and VIIIb were separated by fractional crystallization. The suspension was stirred at room temperature for 1 h and filtrated to give a colorless solid after drying in vacuo (1.01 g). The mother liquor was concentrated until 25 g residue was obtained. Afterwards, the concentrated mixture was heated to 60° C. and cooled within 3 h to 0-5° C. Additional product was obtained after filtration and drying of the wet product in vacuo (0.3 g). The mother liquor was concentrated until 15 g residue was obtained, and diisopropyl ether (15 g) was added. A third fraction was obtained after filtration and drying of the wet product in vacuo (0.33 g). The second and third crop were recrystallized from 2-propanol (3.7 g), and after the filtration, the wet product (0.6 g) was dissolved with the first crop in 2-propanol (10 g) at reflux. The mixture was cooled to 0-5° C. and then filtrated. The wet product was dried in vacuo to give a colorless solid (yield: 1.1 g, ratio VIIIa/VIIIb=96/4).

Diastereomer VIIIb could be e.g., obtained from the mother liquor after concentration to dryness followed by an extractive work up and crystallization.

Example 12

Steps 4-6: Preparation of (±)-2-Benzylamino-1-[6-fluoro-(2R*)-chroman-2-yl]-(S*)-ethan-1-ol (compound VIIIa) and (±)-2-Benzylamino-1-[6-fluoro-(2R*)-chroman-2-yl]-(1R*)-ethan-1-ol (compound VIIIb) from (±)-2-chloro-1-(6-fluoro-chroman-2-yl)-ethanone (compound Vb) and separation of the diastereomers VIIIa and VIIIb

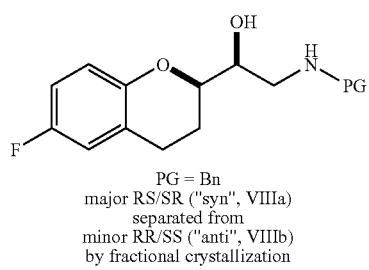

(VIII)

PG = Bn
major RS/SR ("syn", VIIIa)
separated from
minor RR/SS ("anti", VIIIb)
by fractional crystallization Compound Vb (76.31 g, 324 mmol) and $ZnCl_2$ (22.53 g, 162 mmol) was dissolved in ethanol (648 ml) at an internal temperature of 20-30° C. This solution was then cooled to an internal temperature of −15 to −20° C. and a solution of $NaBH_4$ (12.77 g, 324 mmol) and NaOMe (4 ml of a 30% solution in MeOH) in MeOH (136 ml) was added slowly. During the addition the internal temperature was kept between −20 and −10° C. and the reaction was monitored by HPLC. After completion of the reaction the mixture was allowed to warm to 0-5° C. and hydrochloric acid was added (160 ml 2N HCl solution). The mixture was allowed to warm to 20-25° C. and stirred at this temperature for 30 minutes. The solvent was almost removed completely in vacuo to give a brown suspension (191.3 g). This residue was portioned between hydrochloric acid (160 ml 2N HCl solution) and MTBE (450 ml). The organic layer was separated, extracted with hydrochloric acid (30 ml 2N aqueous HCl solution) then twice with water (each 250 ml) and concentrated in vacuo to give a brown oil (79.77 g, ratio VIa/VIb=63.5/36.5). After dissolving of the oil in 2-propanol, a solution of NaOMe in MeOH (64.18 g, concentration: 30%) was added at an internal temperature of 20-25° C. The reaction was monitored by HPLC. After completion of the reaction, the mixture was cooled to 0-5° C. and neutralized by addition of acetic acid (1.9 ml). The suspension was filtered over Celite and the filter cake washed with 2-propanol (25 ml). The filtrate was concentrated in vacuo to give a semiconcentrated turbid brownish solution (115.97 g). This mixture was filtered again and the filter cake washed with 2-propanol (25 ml) to give a clear brown solution which was then slowly added (within 3 h) to a solution of benzylamine (105.2 g, 972 mmol) in 2-propanol (352 ml) at an internal temperature of 33-38° C. The reaction was monitored by HPLC and seeded to initiate the crystallization of the product during the reaction. After completion of the addition, the mixture was stirred for 3.5 h at 25-30° C., then cooled to 0-5° C. and stirred at this temperature for 1.5 h. The suspension was filtered and the filter cake washed with precooled (0-5° C.) 2-propanol (46 ml). The wet product was dried in vacuo at 50-55° C. to give a slightly beige colored solid (42.23 g, ratio VIIIa/VIIIb=92/8). The crude product was dissolved in acetonitrile (294 ml) by heating to reflux. The solution was slowly cooled to 0-5° C. (6-7 h), filtrated and the filter cake washed with acetonitrile (38 ml). The wet product was dried in vacuo at 50-55° C. to give a white solid (overall yield: 38.2 g, ratio VIIIa/VIIIb=98.8/1.2, HPLC-purity of VIIIa: 98.62%).

Example 13

Step 7: Preparation of (±)-2-{Benzyl-[2-(6-fluoro-(2R*)-chroman-2-yl)-(2S*)-hydroxy-ethyl]-amino}-1-(6-fluoro-(2S*)-chroman-2-yl)-ethanone (compound IXa), (±)-4-Benzyl-2-[6-fluoro-(2R*)-chroman-2-yl]-(6S*)-[6-fluoro-(2S*)-chroman-2-yl]-morpholin-2-ol (compound IXa'), (±)-2-{Benzyl-[2-(6-fluoro-(2R*)-chroman-2-yl)-(2S*)-hydroxy-ethyl]-amino}-1-(6-fluoro-(2R*)-chroman-2-yl)-ethanone (compound IXb), and (±)-4-Benzyl-(6S*)-2,6-bis-[6-fluoro-(2R*)-chroman-2-yl]-morpholin-(2S*)-ol (compound IXb') and separation of the diastereomers

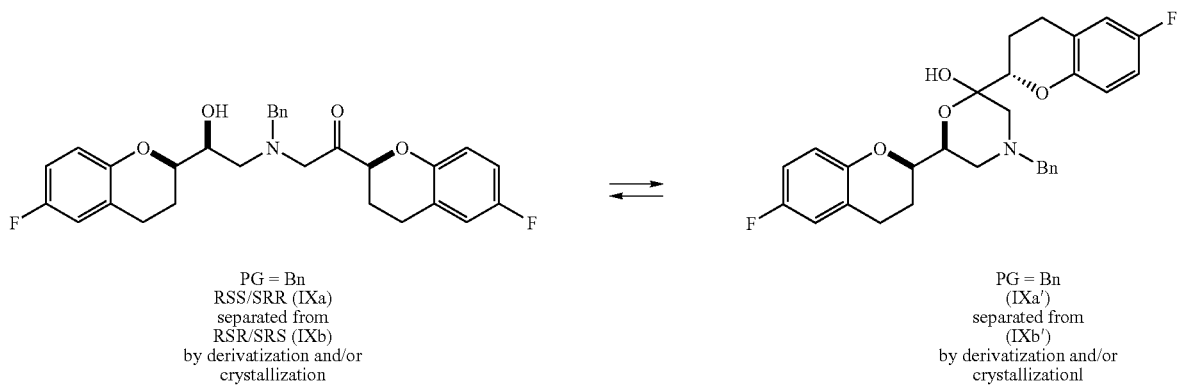

PG = Bn
RSS/SRR (IXa)
separated from
RSR/SRS (IXb)
by derivatization and/or
crystallization PG = Bn
(IXa')
separated from
(IXb')
by derivatization and/or
crystallizationl Compound V (14.62 g) was added at an internal temperature of 40° C. to a suspension of compound VIIIa (17.5 g), NaHCO$_3$ (9.6 g) and NaBr (0.9 g) in DMF (70 ml). When the reaction was completed (within 3-3.5 h, monitored by HPLC), the suspension was cooled to room temperature and diluted with MTBE (400 ml) and water (200 ml). Afterwards, the phases were separated, the organic layer was extracted with water (100 ml), and the combined water layers were reextracted with MTBE (100 ml). After evaporation of the combined organic layers, the remaining amber colored oil (35.0 g) was taken up in diisopropyl ether (400 ml) and seeded. The suspension was initially stirred at room temperature for 1.5 h and then at 0-5° C. for 0.5 h. After filtration, the wet product was dried in vacuo to give a light yellow solid (yield: 23.95 g, HPLC-purity 97.5%, ratio of IXa/IXa' to IXb/IXb'=52/48).

The mother liquor was concentrated to an amount of 56 g, then cooled to 0-5° C. and seeded. A second crop was obtained after filtration and drying (yield: 2.62 g, HPLC-purity 92.6%, ratio of IXa/IXa' to IXb/IXb'=43/57

Separation of the diastereomers was conducted by fractional crystallization from acetonitrile.

The diastereomeric mixture of compounds IXa/IXa' and IXb/IXb' (ratio: 55/45,2.31 g) was dissolved in acetonitrile at an internal temperature of 70° C. The light yellow solution was seeded, cooled to room temperature (within 2-3 h) and stirred at this temperature for 1.5-2 h. Filtration of the suspension and drying of the wet product gave a first crop (yield: 0.26 g, ratio of IXa/IXa' to IXb/IXb'=95/5).

The mother liquor was concentrated to an amount of 30 g and stirred at room temperature after seeding. Filtration of the suspension gave a wet product (1.12 g), which was recrystallized from acetonitrile (11.2 g). Drying of the wet product in vacuo gave a second crop (0.50 g, ratio of IXa/IXa' to IXb/IXb'=62/38). This crop was recrystallized from acetonitrile (10 ml) to give a wet product (0.57 g), which was dissolved again in acetonitrile (8 ml) by heating. The solution was cooled to room temperature and seeded. After filtration of the suspension and drying of the wet product gave a third crop (yield: 0.16 g, ratio of IXa/IXa' to IXb/IXb'=98/2).

Separation of the diastereomers was also conducted by selective silylation and fractional crystallization.

Procedure A:

Imidazole (0.417 g) was added at 0-5° C. to a suspension of compounds IX (2.0 g, prepared according to the above described procedure, ratio of IXa/IXa' to IXb/IXb'=52/48) in a mixture of acetonitrile (13.5 ml) and THF (1.5 ml). Afterwards, TMSCl (0.228 mg) was slowly added at this temperature within 3.5-4 h and under monitoring by HPLC. After the addition was complete, the mixture was concentrated in vacuo to an amount of 8-10 ml, and then acetonitrile (5 ml) was added. Stirring the suspension at 0-5° C. for 1-1.5 h followed by filtration gave a white wet product (1.31 g), which was dried in vacuo (yield: 0.82 g, ratio of IXa/IXa' to IXb/IXb'>98/2).

Procedure B:

Imidazole (0.21 g) was added at 0-5° C. to a suspension of compounds IX (1.0 g, prepared according to the above described procedure, ratio of IXa/IXa' to IXa/IXb'=52/48) in MTBE (10 ml). Afterwards, TMSCl (0.115 mg) was slowly added at this temperature within 3.5-4 h and under monitoring by HPLC. The reaction was completed by addition of 4 drops of TMSCl. Afterwards, the suspension was filtrated, and the wet product (0.87 g) was dried in vacuo to give a white crude product (0.51 g, ratio of IXa/IXa' to IXb/IXb'=98/2, the product contains imidazole hydrochloride). To remove the imidazole hydrochloride, the crude product was slurried at room temperature in a mixture of acetonitrile and water (3.0 ml, 4/1 by volume) for 2.5-3 h. Filtration of the suspension and drying the wet product (0.65 g) in vacuo gave a white solid (yield: 0.31 g, ratio of IXa/IXa' to IXb/IXb'=98/2).

Example 14

Step 7: Preparation of (±)-2-{Benzyl-[2-(6-fluoro-(2R*)-chroman-2-yl)-(2S*)-hydroxy-ethyl]-amino}-1-(6-fluoro-(2S*)-chroman-2-yl)-ethanone (compound IXa), (±)-4-Benzyl-2-[6-fluoro-(2R*)-chroman-2-yl]-(6S*)-[6-fluoro-(2S*)-chroman-2-yl]-morpholin-2-ol (compound IXa'), (±)-2-{Benzyl-[2-(6-fluoro-(2R*)-chroman-2-yl)-(2S*)-hydroxy-ethyl]-amino}-1-(6-fluoro-(2R*)-chroman-2-yl)-ethanone (compound IXb), and (±)-4-Benzyl-(6S*)-2,6-bis-[6-fluoro-(2R*)-chroman-2-yl]-morpholin-(2S*)-ol (compound IXb') and separation of the diastereomers

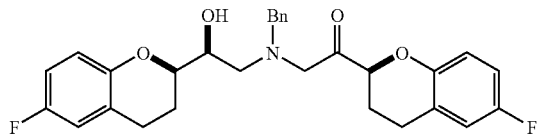

PG = Bn
RSS/SRR (IXa)
separated from
RSR/SRS (IXb)
by derivatization and/or
crystallization

⇌

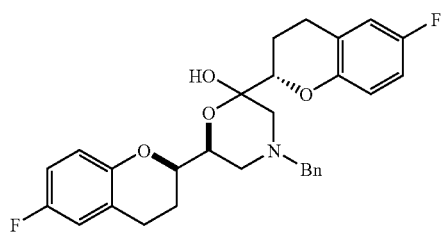

PG = Bn
(IXa')
separated from
(IXb')
by derivatization and/or
crystallizationl

A mixture of compound VIIIa (49.0 g, 162.6 mmol, prepared according to example 12), compound Vb (42.5 g, 178.9 mmol, prepared according to example 8), NaBr (1.68 g, 16.3 mmol) and NaHCO₃ (20.5 g, 243.9 mmol) in DMF (200 ml) was heated to an internal temperature of 60-65° C. until an in process HPLC analysis showed an almost complete conversion (approx. 1 h). Afterwards the suspension was filtered and the filter cake washed with DMF (70 ml). To the filtrate was added at 50° C. water (15 ml) and seeding crystals to initiate the crystallization. Then the product was careful precipitated by slow addition of water (within 4 h) at 50° C. Finally the precipitation was completed by addition of water (25 ml) at 50° C. The suspension was cooled to 20-25° C. and filtrated. The wet product was washed with 2-propanol (100 ml) and dried in vacuo at 50° C. to give a white solid (yield: 70.15 g, HPLC-purity: 99.1%, ratio of IXa/IXa' to IXb/IXb'=52/48). To a suspension of this solid (70.0 g) and imidazole (14.6 g, 214 mmol) in acetonitrile (385 ml) was added slowly (1.75 ml/h) TMSCl (7.56 g, 68.2 mmol) at an internal temperature of −10 to −15° C. After that the suspension was stirred for 2 h at −5 to 0° C. under monitoring by HPLC. The reaction was completed by addition of TMSCl (1.34 g, 12.3 mmol). The suspension was filtered and the wet product dried in vacuo at 40° C. to give a white solid (66.45 g, ratio of IXa/IXa' to IXb/IXb'=92/8). This product was slurried in a mixture of cyclohexane (285 ml) and MTBE (95 ml) at an internal temperature of 60° C. for 10 minutes. After the suspension was cooled to 25° C. and filtrated, the wet product was washed with cyclohexane (50 ml) and suspended again in cyclohexane (350 ml). The suspension was stirred at 60-65° C. for 20 minutes, then cooled to 25° C. and filtered. The wet product was washed with cyclohexane (50 ml) and dried in vacuo at 40° C. to give a white solid (overall yield: 28.83 g, , ratio of IXa/IXa' to IXb/IXb'=98.6/1.4).

Example 15

Step 8: Preparation of (±)-[2R*[R*[R*(S*)]]]-α,α'-[[(phenylmethyl)imino]bis-(methylene)]bis[6-fluoro-chroman-2-methanol] (compound Xa) and (±)-[2R*[S*[R*(S*)]]]-α,α'-[[(phenylmethyl)imino]bis(methylene)]bis[6-fluoro-chroman-2-methanol] (compound Xb)

(X)

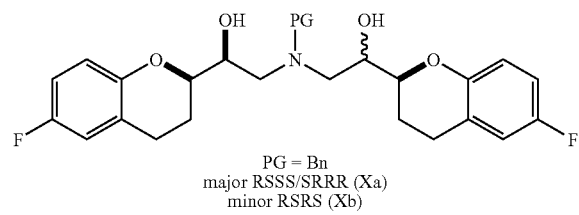

PG = Bn
major RSSS/SRRR (Xa)
minor RSRS (Xb)

A solution of compound IXa/IXa' (0.40 g, containing 2% of compound IXb) in THF (8.0 ml) was cooled to an internal temperature of −10 to −15° C. To this solution, Ti(OiPr)₄ (0.485 mg) was added followed by LiBH₄ (18 mg). After stirring at −10 to −15° C. for 1 h and at 0-5° C. for 1.5-2 h, the reaction mixture was poured into a mixture of methylene chloride (10 ml) and saturated NaHCO₃ solution (10 ml). The suspension was filtered over Celite, and the phases were separated. After drying over MgSO₄, the organic layer was concentrated to give a colorless foam (418 mg, ratio of Xa/Xb=78/22): The crude product was used for the next step without any further purification.

Example 16

Step 8: Preparation of (±)-[2R*[R*[R*(S*)]]]-α,α'-[[(phenylmethyl)imino]bis-(methylene)]bis[6-fluoro-chroman-2-methanol] (compound Xa)

(X)

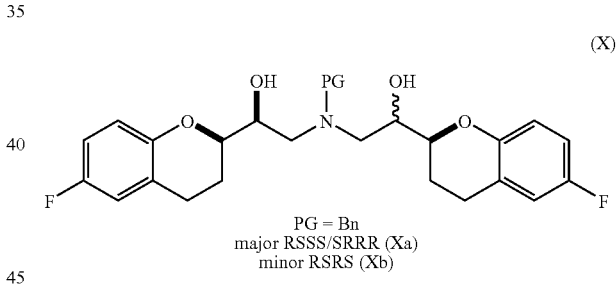

PG = Bn
major RSSS/SRRR (Xa)
minor RSRS (Xb)

KBH₄ (3.15 g, 56.73 mmol) was added to a solution of compound IXa/IXa' (28.0 g, prepared according to example 14) and Ti(OiPr)₄ (32.9 g, 113.5 mmol) in DME (280 ml) at an internal temperature of 0° C. After stirring at this temperature for 21 h (monitored by HPLC), the mixture was allowed to warm to room temperature and hydrochloric acid (280 ml, 10% aqueous solution) was added slowly. The suspension was stirred for 2.5 h. The suspension was filtered and the wet product washed first with a mixture of DME (25 ml) and hydrochloric acid (25 ml, 2N aqueous solution), then with hydrochloric acid (50 ml, 2N aqueous solution) and twice with water (each 50 ml). The wet product was suspended in ethanol (120 ml) and heated to 50° C. Afterwards, an aqueous solution of NaOH (8.3 g, 30%) was added to give initially a clear solution and the mixture was heated to 60° C. After the crystallization started, water was added (33 ml) and the suspension was cooled to room temperature. The suspension was filtered and the wet product washed with a mixture of EtOH/water (20 ml, v/v=3/1). Next, the wet product was dissolved in EtOH (160 ml) by heating to 70-75° C. and then cooled to 65° C. Water (40 ml) and seeding crystals were added and the mixture was cooled to room temperature and stirred at this temperature over night. After filtration, the wet product was washed with a mixture of EtOH/water (30 ml, v/v=3/1) and dried in vacuo at 50° C. to give a white solid (yield: 21.66 g, HPLC-purity: 99.85%).

Example 17

Step 9: Preparation of (±)-[2R*[R*[R*(S*)]]]-α,α'-[iminobis(methylene)]bis[6-fluoro-chroman-2-methanol] hydrochloride. (compound I) and separation from the byproduct (±)-[2R*[S*[R*(S*)]]]-α,α'-[iminobis-(methylene)]bis[6-fluoro-chroman-2-methanol] hydrochloride

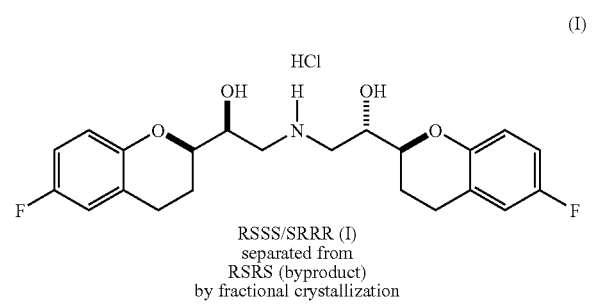

RSSS/SRRR (I)
separated from
RSRS (byproduct)
by fractional crystallization

The compounds Xa and Xb (418 mg, ratio of Xa/Xb=78/22, prepared according to Example 11) were dissolved in a mixture of EtOH containing 14% HCL (0.665 g) and MeOH (10 ml). This mixture was hydrogenated at normal pressure and at room temperature with palladium-on-charcoal catalyst 5% (100 mg). After completion of the reaction (within 3 h), the mixture was diluted with MeOH (25 ml), heated to 40° C. and then filtrated over Celite. The filter cake was washed with hot MeOH (40° C., 30 ml), and the combined filtrates were concentrated in vacuo to an amount of 7-8 g. The resulting suspension was filtrated to give a colorless solid after drying of the wet product (yield: 0.17 g, ratio of compound I/byproduct=95.5/4.5). The mother liquor was concentrated, and the residue taken up in 2.0 ml MeOH. The suspension was stirred at room temperature for 0.5 h and then filtrated to give an additional crop (yield: 28 mg) after drying the wet product in vacuo. Both crops were recrystallized from MeOH (2.0 ml) to give a colorless solid (yield: 0.161 g, ratio of compound I/byproduct=98/2) after drying.

Example 18

Step 9: Preparation of (±)-[2R*[R*[R*(S*)]]]-α,α'-[iminobis(methylene)]bis[6-fluoro-chroman-2-methanol] hydrochloride (compound I)

A mixture of compound Xa (21.0 g, 42.3 mmol, prepared according to example 16) and palladium-on-charcoal catalyst 5% (1.35 g) in acetic acid (150 ml) was hydrogenated at normal pressure and at an internal temperature of 40° C. After an in process HPLC analysis showed complete deprotection, the suspension was filtered over Celite. The filtrate was cooled to 20° C. and concentrated aqueous hydrochloric acid was added (4.59 g, 46.5 mmol). After filtration, the wet product was washed first with acetic acid (10 ml) then with ethanol (20 ml) and dried in vacuo to give a white solid (yield: 18.05 g, HPLC-purity: 99.7%).

While the invention has been described in detail and with reference to specific examples thereof, it will be apparent to one skilled in the art that various changes and modifications can be made therein without departing from the spirit and scope thereof.

What is claimed is:

1. A process for preparing racemic [2S*[R*[R*[R*]]]] and [2R*[S*[S*[S*]]]]-(+)α,α'-[iminobis(methylene)]bis[6-fluoro-3,4-dihydro-2H-1-benzopyran-2-methanol]and pharmaceutically acceptable salts thereof, the process comprising:

(a) providing a compound of formula (VIII)

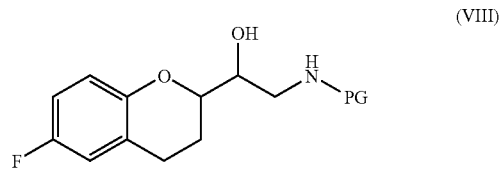

as a diastereomerically pure compound comprising at least 95% of RS/SR configuration or RR/SS configuration, wherein PG is hydrogen or an amine protecting group, wherein the amine protecting group is at least one of an allyl group or an aryl-$C_1$ alkyl group;

(b) providing a racemic compound of formula (V)

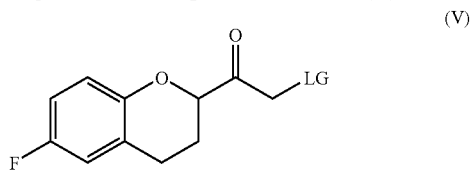

wherein LG is a member selected from the group consisting of chloro, bromo, iodo, alkylsulfonyloxy and arylsufonyloxy;

(c) N-alkylating the compound of formula (VIII) with the compound of formula (V), wherein said N-alkylating is carried out in an inert organic solvent in a presence of a base and optionally in the presence of a catalyst to give a compound of formula (IX)

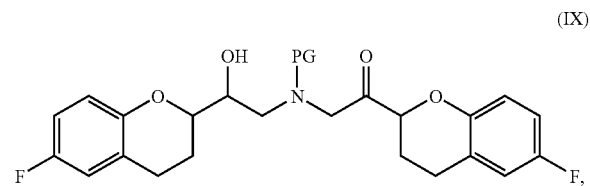

a compound of formula (IX') which is a cyclic semi-ketal form of the compound of formula (IX)

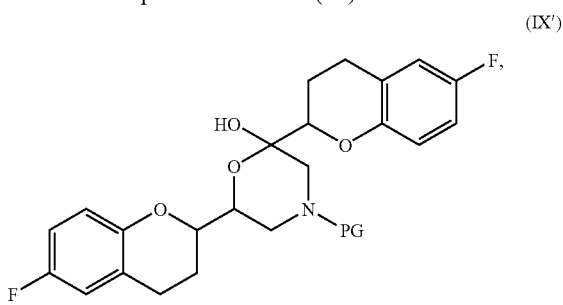

or a mixture thereof, wherein the compound of formula (IX) and the compound of formula (IX') are mixtures of diastereomers;

(d) separating diastereomers of the compound of formula (IX) or the compound of formula (IX') by fractional crystallization to obtain substantially pure diastereomers of formula (IX) or formula (IX') having at least 50% of a RSS/SRR or RRS/SSR configuration;

(e) reducing substantially pure diastereomers of formula (IX) or formula (IX') having a RSS/SRR or RRS/SSR configuration to give a compound of formula (X)

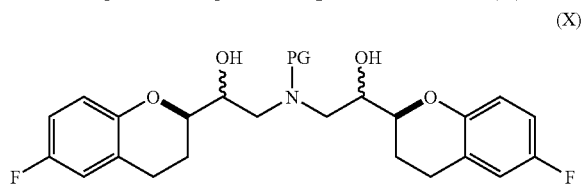

(X)

as a RSSS/SRRR diastereomeric mixture having a ratio of a RSSS/SRRR diastereomeric configuration to a SRSR or RRSS diastereomeric configuration, wherein said ratio is at least 1;

(f) deprotecting the compound of formula (X), provided that PG is not H and if PG is H then omitting said deprotecting, to obtain a compound of formula (I)

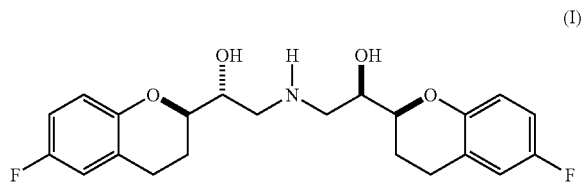

(I)

or pharmaceutically acceptable salts thereof; and (g) removing a RSRS or RRSS diastereomeric configuration of the compound of formula (I) or pharmaceutically acceptable salts thereof if present by recrystallization or by a slurry to give racemic [2S*[R*[R*[R*]]]] and [2R*[S*[S*[S*]]]]-(±).α,α'-[iminobis(methylene)]bis[6-fluoro-3,4-dihydro-2H-1-benzopyran-2-methanol]or pharmaceutically acceptable salts thereof.

2. The process according to claim 1, wherein the protecting group is a benzyl group.

3. The process according to claim 1, wherein the leaving group is chloro or bromo.

4. The process according to claim 1, wherein in step (c) the organic solvent is a polar aprotic solvent selected from the group consisting of dimethylformamide (DMF), dimethylacetamide (DMA) and N-methylpyrrolidone (NMP).

5. The process according to claims 1, wherein in step (c), the base is at least one of tertiary amines, alkali metal carbonate or alkali metal hydrogen carbonate.

6. The process according to claim 5, wherein the base is sodium hydrogen carbonate.

7. The process according to claim 6, wherein about 1.5 to about 2.5 equivalents of the base are used.

8. The process according to claim 1, wherein in step (c) the catalyst is at least one of alkali metal bromides, alkali metal iodides, tetraalkylammonium bromides or tetraalkylammonium iodides.

9. The process according to claim 8, wherein the catalyst is sodium bromide.

10. The process according to claim 9, wherein about 0.1 to about 0.25 equivalents of the catalyst are used.

11. The process according to claim 10, wherein 0.15 equivalents of the catalysts are used.

12. The process according to claim 1, wherein in step (c) said N-alkylation is carried out at a temperature between about room temperature and about 80° C.

13. The process according to claim 1, wherein in step (b) the compound of formula (V) is provided in an amount of about 1.0 to about 1.5 equivalents.

14. The process according to claim 1, wherein in step (d) the fractional crystallization is carried out in a solvent.

15. The process according to claim 14, wherein in step (d) a free amine is used for the fractional crystallization.

16. The process according to claim 14, wherein the solvent is acetonitrile.

17. The process according to claim 1, wherein in step (d), a silylation reagent is used for derivatization prior to the fractional crystallization from the solvent.

18. The process according to claim 17, wherein the silylating reagent is at least one of trimethylsilyl chloride (TMSCl), HMDS(Hexamethyldisilazane) or BSU (N,N'Bis(trimethylsilyl)urea).

19. The process according to claim 17, wherein about 0.4/n to about 0.6/n equivalents of the silylating reagent are used and wherein n is an amount of transferred silyl groups per the silylating reagent.

20. The process according to claim 17, wherein the derivatization is carried out in the presence of about 1.0 to about 2.0 equivalents of a base.

21. The process according to claim 20, wherein the base is imidazole.

22. The process according to claim 17, wherein said separating the diastereomers of the compound of formula (IX) or the compound of formula (IX') is carried out in acetonitrile, MTBE, cyclohexane or mixtures thereof.

23. The process according to claim 1, wherein in step (e) said reducing is carried out in a solvent with alkali borohydride, tetrabutylammonium borohydride, alkali-SELECTRIDE or zinc borohydride, optionally in a presence of a Lewis acid.

24. The process according to claim 23, wherein the Lewis acid is at least one of $Ti(OAlkyl)_4$, $ZnCl_2$ alkali halide or alkaline earth halide.

25. The process according to claim 23, wherein the solvent is at least one of an ether, an alcohol or a halogenated hydrocarbon.

26. The process according to claim 23, wherein said reducing is carried out at temperatures between about −20° C. and about room temperature.

27. The process according to claim 1, wherein in step (f) said deprotecting is carried out by catalytic hydrogenation.

28. The process according to claim 1, wherein in step (g), said purifying the compound of formula (I) is done by a slurry of its hydrochloride salt in a solvent.

29. The process according to claim 28, wherein the slurry is carried out in methanol as the solvent.

30. The process according to claim 1, wherein said providing the compound of formula (VIII) comprises:

(i) reducing the racemic compound of formula (V) in a solvent and optionally in a presence of a Lewis acid, wherein LG is bromine or chlorine to give a mixture of diastereomers of a compound of formula (VI)

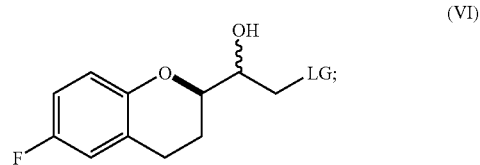

(VI)

(ii) forming a mixture of diastereomers of a compound of formula (VII)

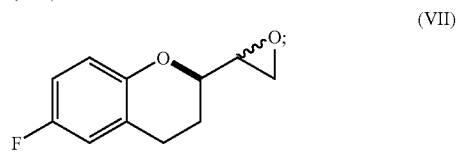

(VII)

(iii) reacting diastereomers of the compound of formula (VII) with NH$_2$PG to give a mixture of diastereomers of the compound of formula (VIII)

(VIII)

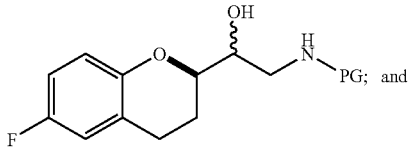

(iv) separating diastereomers of the compound of formula (VIII) from the mixture of diastereomers of the compound of formula (VIII) by the fractional crystallization optionally after formation of a salt.

31. The process according to claim 30, wherein at least one of the diastereomers of the compound of formula VIII having a RR/SS or RS/SR configuration is isolated.

32. the process of claim 31, further comprising recycling the RR/SS configuration of the compound of formula (VIII), wherein said recycling comprises:
    providing the RR/SS configuration of the compound of formula (VIII) with a protective group; and
    inversion of the alcohol configuration to provide the SR/RS configuration of formula VIII.

33. The process according to claim 30, wherein in step i), the reducing agent is selected from alkali borohydride, tetraalkylammonium borohydride, zinc borohydride, alkali triacetoxyborohydride, SUPERHYDRIDE, RED-AL, alkali-SELECTRIDE or coordinated borohydrides.

34. The process according to claim 30, wherein in step i), the reduction is carried out under Meerwein Pondorf Verley conditions.

35. The process according to claim 30, wherein in step i) said reducing is carried out by catalytic hydrogenation.

36. The process according to claim 30, wherein in step i) the Lewis acid is a member selected from the group consisting of alkali or alkaline earth chlorides, zinc chloride, titanium (IV) alkoxide, and aluminium trialkoxide.

37. The process according to claim 30, wherein in step i) said reducing is carried out under conditions which give an RR/SS isomer of the compound of formula (VI) in excess.

38. The process according to claim 30, wherein in step i) said reducing is carried out at a temperature between about −78° C. and about room temperature.

39. The process according to claim 38, wherein said reducing is carried out at the temperature between −20° C. and room temperature.

40. The process according to claim 30, wherein in step i) the solvent is a member selected from the group consisting of alcohols, ethers, halogenated hydrocarbons and aromatic solvents.

41. The process according to claim 30, wherein PG is a benzylic group.

42. The process according to claim 30, wherein in step ii) said forming the mixture of diastereomers of the compound of formula (VII) is carried out in a solvent and in a presence of a base.

43. The process according to claim 42, wherein the solvent is an alcohol and the base an alkali alcoholate.

44. The process according to claim 43, wherein 1.0 to 2.0 equivalents of the base are used.

45. The process according to claim 30, wherein in step ii), said forming of the mixture of diastereomers of the compound of formula (VII) is carried out at temperatures between 0° C. and 40° C.

46. The process according to claim 30, wherein in step iv), the fractional crystallization is carried out in toluene, acetonitrile, a C$_1$-C$_3$-alcohol, an ether or mixtures thereof.

47. The process according to claim 46, wherein the C$_1$-C$_3$-alcohol is 2propanol and the ether is at least one of diisopropylether or MTBE.

48. The process according to claim 1, wherein said providing the racemic compound of formula (V) comprises:
    (1) transforming a compound of formula (II)

(II)

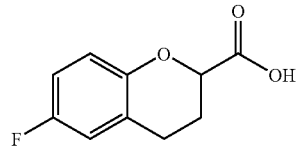

into an activated acid derivative;
    (2) reacting the activated acid derivative with Meidrums acid in a presence of a base to give a compound of formula (III)

(III)

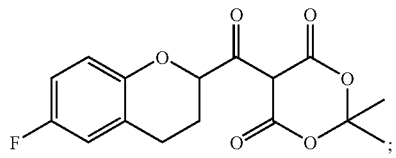

(3) converting the compound of formula (III) into a compound of formula (IV)

(IV)

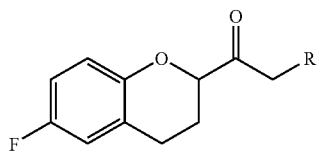

wherein R is hydrogen or COOR' and wherein R' is C$_1$-C$_6$ alkyl or aryl-C$_1$-alkyl; and
    (4) halogenating the compound of formula (IV) and optionally conducting hydrolysis and decarboxylation to give the compound of formula (V)

49. The process according to claim 48, wherein in step (1), the carboxylic acid is transformed into a corresponding acid chloride.

50. The process according to claim 48, wherein in step (2), the base is a tertiary amine.

51. The process according to claim 48, wherein in step (2), 1 to 3 equivalents of Meldrums acids are used.

52. The process according to claim 48, wherein in step (2), the reaction temperature is between about −10° C. and about +30° C.

53. The process according to claim 48, wherein in step (3), the compound of formula (III) is hydrolyzed in a mixture of an organic acid and water to give a compound of formula (IV) wherein R is H.

54. The process according to claim 53, wherein the organic acid is acetic acid and the hydrolysis is carried out at a reflux temperature.

55. The process according to claim 48, wherein in step (3), the compound of formula (IV) having R as COOR' and R' as C$_1$-C$_6$ alkyl or aryl-C$_1$ alkyl is prepared by an alcoholysis of the compound of formula (III)

56. The process according to claim 55, wherein the alcoholysis is carried out with ethanol and tert-butanol.

57. The process according to claim 48, wherein in step (3), the solvent is at least one of alcohol or toluene.

58. The process according to claim 55, where in the alcoholysis is carried out at temperatures between about 70° C. and 80° C.

59. The process according to claim 48, wherein in step (4), before the halogenation is carried out the compound of formula (IV) wherein R is H is transformed to a corresponding silylenol ether having the terminal double bond by silylation.

60. The process according to claim 59, wherein the silylation is done by a kinetically controlled deprotonation using LDA followed by silylation at about −78° C. to about −40° C.

61. The process according to claim 60, wherein the silylation is done at −78° C. to −70° C.

62. The process according to claim 60, wherein trimethylsilyl chloride (TMSCl) is used as a silylating reagent.

63. The process according to claim 48, wherein in step (4), after the transformation to the silylenol ether, the halogenation is carried out by using a brominating reagent.

64. The process according to claim 63, wherein the bromination reagent is N-bromosuccinimide.

65. The process according to claim 48, wherein in step (4), the compound of formula (IV) wherein R is COOR' is first halogenated and then transformed into the compound of formula (V) by ester hydrolysis followed by decarboxylation.

66. The process according to claim 65, wherein the halogenation is done in a presence of a catalyst.

67. The process according to claim 66, wherein about 1.0 to about 1.5 equivalents of NBS, NCS or $SO_2Cl_2$ are used as halogenation reagents.

68. The process according to claim 67, wherein about 0.2 equivalents to 0.4 equivalents of $Mg(ClO_4)_2$ are used as a catalyst.

69. The process according to claim 48, wherein in step (4), said halogenating is carried out at temperatures between 0° C. and about room temperature.

70. The process according to claim 48, wherein in step (4), after said halogenating, the hydrolysis of the ester followed by decarboxylation is carried out in an aqueous organic acid solution.

71. The process according to claim 70, wherein the organic acid is at least one of trifluoro acetic acid, formic acid and acetic acid.

72. The process according to claim 71, wherein the hydrolysis and decarboxylation are carried out at temperatures between about 75° C. and about 90° C.

73. The process of claim 1, further comprising recycling an RSR/SRS or RRR/SSS configuration of the compound of formula (IX) or (IX'), wherein said recycling comprises:
    epimerizing the RSR/SRS or RRR/SSS configuration of the compound of formula (IX) or (IX') to give a mixture of the RSS/SRR configuration containing the RSR/SRS configuration of diastereomers of formula (IX) or formula (IX') or RRS/SSR configuration containing the RRR/SSS configuration of diastereomers of formula (IX) or formula (IX') and
    separating the mixture by fractional crystallization after salt formation or after derivatization to obtain substantially pure diastereomers of formula (IX) or formula (IX') having the RSS/SRR or RRS/SSR configuration.

74. The process of claim 1, further comprising recycling an RSR/SRS or RRR/SSS configuration of the compound of formula (IX) or (IX') wherein said recycling comprises:
    cleaving the RSR/SRS or RRR/SSS configuration of the compound of formula (IX) or (IX') to give a mixture comprising an RS/SR or RR/SS configuration of diastereomers of formula (VIII); and
    separating the RS/SR or RR/SS configuration of diastereomers of formula (VIII)

75. A compound of formula (III)

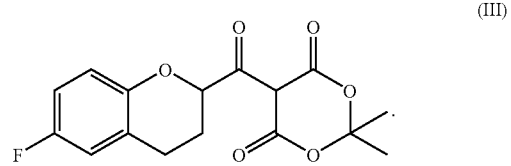

(III)

76. A compound of formula (V)

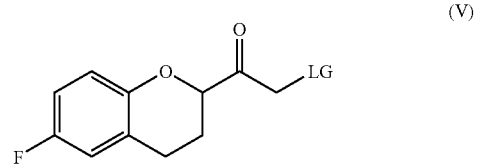

(V)

wherein LG is bromine or chlorine.

77. A compound of formula (VI)

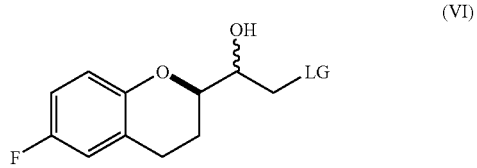

(VI)

wherein LG is bromine or chlorine.

78. A compound of formula (IX)

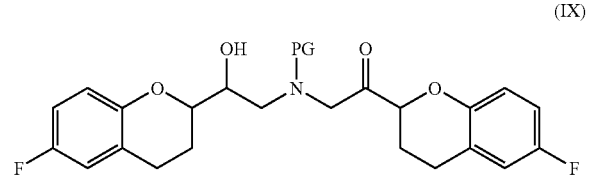

(IX)

or its cyclic semikatal form having the formula (IX')

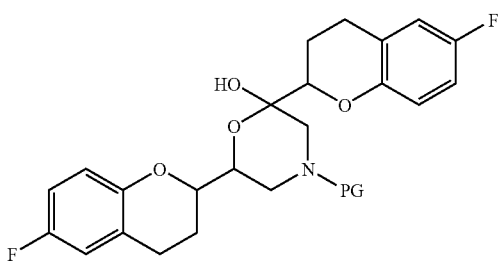

wherein PG is protecting group selected from hydrogen, allyl and aryl-$C_1$ alkyl.

79. A compound of formula (IX) having a RSS/SRR configuration

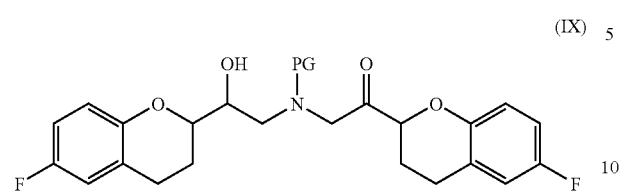

or its corresponding cyclic semi-ketal form (IX')

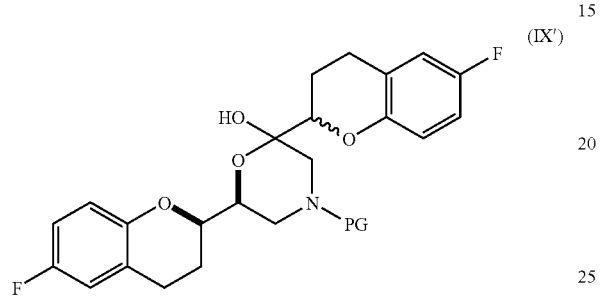

wherein PG is a benzylic group.

80. A racemic ([2S*[R*[R*[R*]]]]- and ([2R*[S*[S* [S*]]]]-(±)-alpha,alpha'[imino-bis(methylene)]bis[6-fluoro-chroman-2-methanol] of the compound of the formula (I)

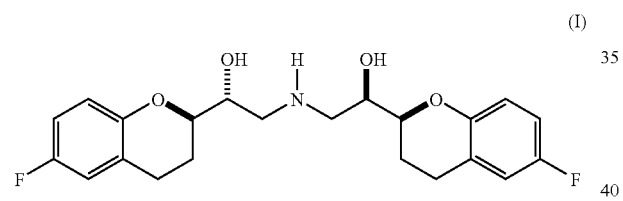

prepared by the process of claim 1.

81. A process for preparing racemic [2S*[R*[R*[R*]]]] and [2R*[S*[S*[S*]]]]-(±).α,α'-[iminobis(methylene)]bis [6-fluoro-3,4-dihydro-2H-1-benzopyran-2-methanol] and pharmaceutically acceptable salts thereof, the process comprising:
providing a compound of formula (IX); and
reducing the compound of formula (IX) to obtain a compound of formula (X) having at most 50% of a stereoisomer with a RSRS configuration.

82. The process of claim 81, further comprising providing a compound of formula (VIII) and a compound of formula (V).

83. A process of preparing a compound of formula (I) and pharmaceutically acceptable salts thereof the process comprising:
(a) resolving a compound of formula (II)

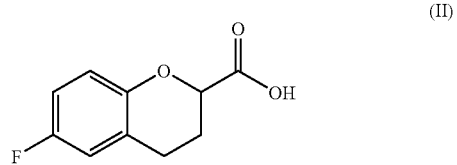

to obtain an S configuration and an R configuration of the compound of formula (II);
(b) converting the S configuration of the compound of formula (II) into an S configuration of a compound of formula (V)

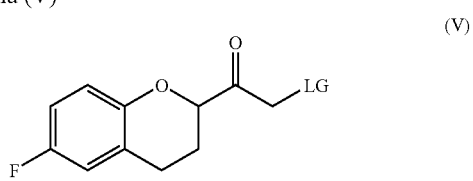

wherein LG is a member selected from the group consisting of chloro, bromo, iodo, alkylsulfonyloxy and arylsufonyloxy, via formation of an S configuration of a compound of formula (III) and an S configuration of a compound of formula (IV);
(c) converting the R configuration of the compound of formula (II) into an R configuration of the compound of formula (V) via formation of an R configuration of the compound of formula (III) and an R configuration of the compound of formula (IV);
(d) providing a compound of formula (VIII)

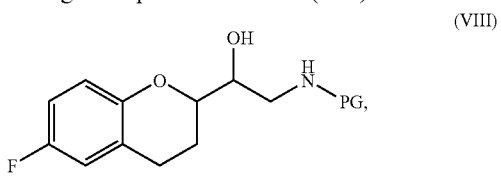

wherein PG is hydrogen or an amine protecting group, wherein the amine protecting group is at least one of an allyl group or an aryl-$C_1$ alkyl group and wherein the compound of formula (VIII) is enantiomeric compound having an RS or SR configuration;
(e) conducting N-alkylation of (i) the RS configuration of compound of formula (VIII) with the S configuration of compound of formula (V) or (ii) the SR configuration of compound of formula (VIII) with the R configuration of compound of formula (V), provided that said N-alkylation is carried out in an inert organic solvent in a presence of a base and optionally in the presence of a catalyst to give a RSS or SRR enantiomeric form of a compound of formula (IX)

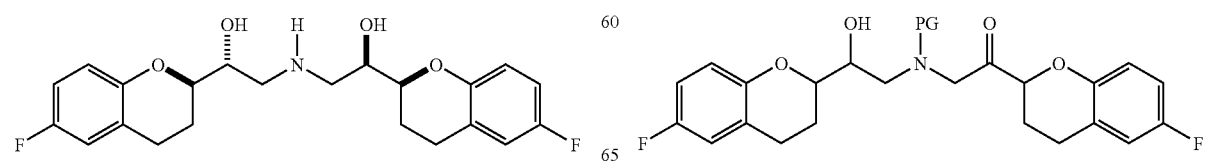

or a RSS or SRR enantiomeric form of a compound of formula (IX') which is a cyclic semiketal form of the compound of formula (IX)

(IX')

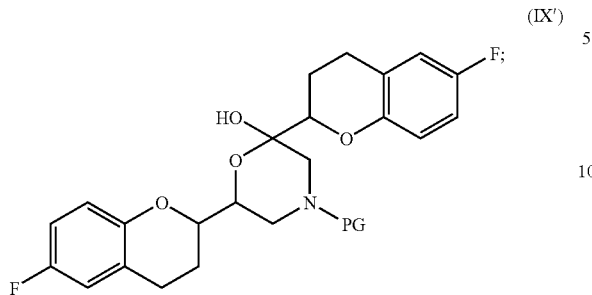

(f) reducing at least one of the RSS or SRR enantiomeric form of the compound of formula (IX) or formula (IX') to give at least one RSSS or SRRR enantomeric form of a compound of formula (X)

(X)

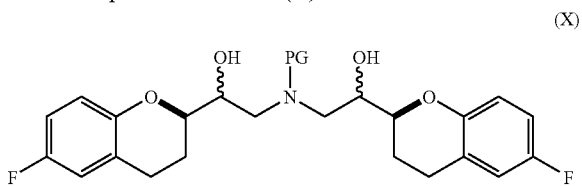

(g) deprotecting the at least one of the RSSS or SRRR enantiomeric form of the compound of formula (X), provided that PG is not H and if PG is H then omitting said deprotecting, to obtain the compound of formula (I) or pharmaceutically acceptable salts thereof; and (h) removing a RSRS diastereomeric configuration of the compound of formula (I) or pharmaceutically acceptable salts thereof if present as a byproduct by recrystallization or by a slurry to give at least one of ([2S*[R*[R*[R*]]]]-and ([2R*[S*[S*[S*]]]]-enantiomer of the compound of the formula (I) and pharmaceutically acceptable salts thereof; and (i) optionally combining ([2S*[R*[R*[R*]]]]-and ([2R*[S*[S*[S*]]]]-enantiomer of the compound of the formula (I) and pharmaceutically acceptable salts thereof to form racemic ([2S*[R*[R*[R*]]]]-and ([2R*[S*[S*[S*]]]]-(±) -alpha, alpha'-[imino-bis(methylene)]bis[6-fluoro-chroman-2-metanol]of the compound of the formula (I) and pharmaceutically acceptable salts thereof.

84. A process for preparing racemic [2S*[R*[R*[R*]]]] and [2R*[S*[S*[S*]]]]-(±).☐.☐'-[iminobis(methylene)]bis [6-fluoro-3,4-dihydro-2H-1-benzopyran-2-methanol] and pharmaceutically acceptable salts thereof, the process comprising:

(a) providing a compound of formula (VIII)

(VIII)

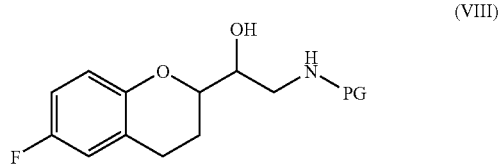

as a diastereomer having RR/SS configuration, wherein PG is hydrogen or an amine protecting group, wherein the amine protecting group is at least one of an allyl group or an aryl-$C_1$ alkyl group;

(b) providing a racemic compound of formula (V)

(V)

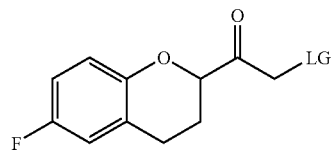

wherein LG is a member selected from the group consisting of chloro, bromo, iodo, alkylsulfonyloxy and arylsufonyloxy;

(c) N-alkylating the compound of formula (VIII) with the compound of formula (V), wherein said N-alkylating is carried out in an inert organic solvent in a presence of a base and optionally in the presence of a catalyst to give a compound of formula (IX)

(IX)

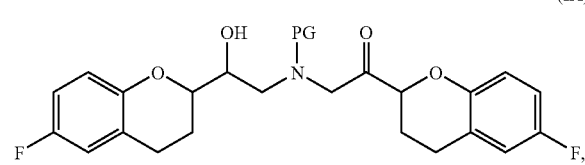

a compound of formula (IX') which is a cyclic semi-ketal form of the compound of formula (IX)

(IX')

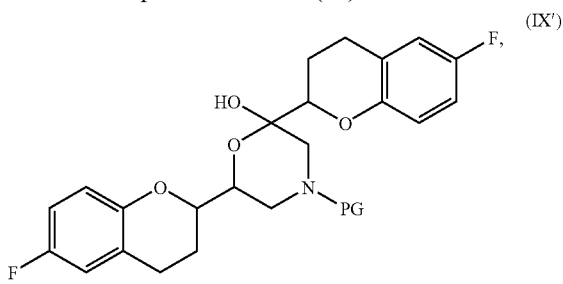

or a mixture thereof, wherein the compound of formula (IX) and the compound of formula (IX') are mixtures of diastereomers having a RRR/SSS and RRS/SSR configuration;

(d) separating diastereomers of the compound of formula (IX) or the compound of formula (IX') by fractional crystallization after salt formation or after derivatization to obtain substantially pure diastereomers of formula (IX) or formula (IX') having at least 50% of the RRR/SSS or RRS/SSR configuration;

(e) reducing the substantially pure diastereomers of formula (IX) or formula (IX') having a RRS/SSR configuration to give a compound of formula (X)

(X)

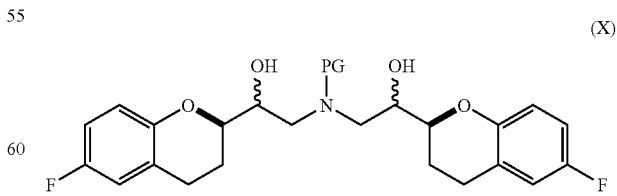

as a RSSS/SRRR diastereomeric mixture having a ratio of a RSSS/SRRR diastereomeric configuration to a SRSR or RRSS diastereomeric configuration, wherein said ratio is at least 1;

(f) deprotecting the compound of formula (X), provided that PG is not H, to obtain a compound of formula (I)

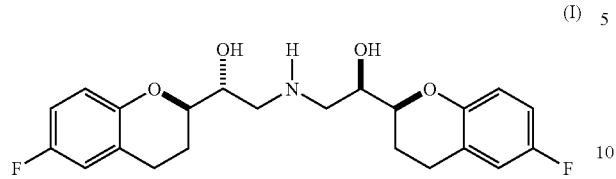

or pharmaceutically acceptable salts thereof; and
(g) removing a RSRS diastereomeric configuration of the compound of formula (I) or pharmaceutically acceptable salts thereof if present by recrystallization or by a slurry to give racemic [2S[2R*[R[R*]]]] and [2R[2S*[S[S*]]]]-(±).☐.☐'-[iminobis(methylene)]bis[6-fluoro-3,4-dihydro-2H-1-benzopyran-2-methanol] or pharmaceutically salts thereof.

85. The process of claim 84, further comprising:
epimerizing the RRR/SSS configuration of the compound of formula (IX) or the compound of formula (IX') to give said mixtures of diastereomers having the RRR/SSS and RRS/SSR configuration of the compound of formula (IX) or the compound of formula (IX').

86. The process of claim 84, further comprising cleaving the RRR/SSS configuration of the compound of formula (IX) or the compound of formula (IX') to give the compound of formula (VIII) as the diastereomer having RR/SS configuration.

87. The process of claim 85, further comprising cleaving the RRR/SSS configuration of the compound of formula (IX) or the compound of formula (IX') to give the compound of formula (VIII) as the diastereomer having RR/SS configuration.

88. A process of making a compound of formula (VIII)

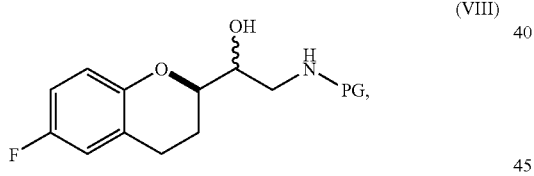

the process comprising:
(i) providing a racemic compound of formula (V)

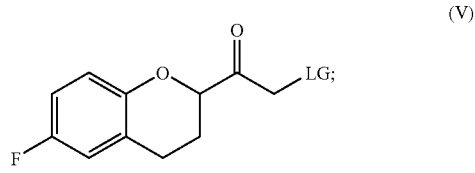

(i) reducing the racemic compound of formula (V) in a solvent and optionally in a presence of a Lewis acid, wherein LG is bromine or chlorine to give a diastereomeric mixture of a compound of formula (VI)

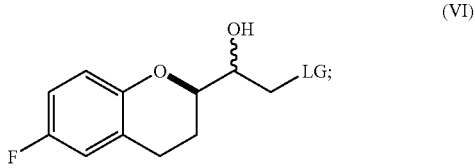

(ii) forming a mixture of diastereomers of a compound of formula (VII)

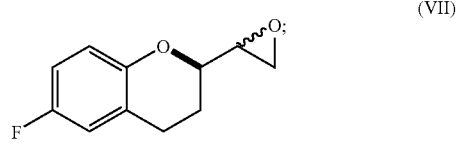

(iii) reacting diastereomers of the compound of formula (VII) with NH₂PG to give the compound of formula (VIII) as a mixture of diastereomers; and
iv) optionally separating diastereomers of the compound of formula (VIII) from the mixture of diastereomers by the fractional crystallization.

89. The process according to claim 14, wherein in step (d) the fractional crystallization is conducted after salt formation or after derivatization of the compound of formula (IX) or the compound of formula (IX').

* * * * *